(12) United States Patent
Kitabayashi et al.

(10) Patent No.: US 7,384,739 B2
(45) Date of Patent: Jun. 10, 2008

(54) COMPOSITIONS FOR ENHANCING DNA SYNTHESIS, DNA POLYMERASE-RELATED FACTORS AND UTILIZATION THEREOF

(75) Inventors: Masao Kitabayashi, Tsuruga (JP); Toshihiro Kuroita, Tsuruga (JP); Yoshikazu Ishida, Tsuruga (JP); Hideyuki Komatsubara, Tsuruga (JP); Yoshiaki Nishiya, Tsuruga (JP); Masanori Oka, Tsuruga (JP); Yoshihisa Kawamura, Tsuruga (JP); Tadayuki Imanaka, Suita (JP)

(73) Assignee: Toyo Boseki Kabushiki Kaisha, Osaka (JP)

( * ) Notice: Subject to any disclaimer, the term of this patent is extended or adjusted under 35 U.S.C. 154(b) by 440 days.

(21) Appl. No.: 10/495,581

(22) PCT Filed: Nov. 14, 2002

(86) PCT No.: PCT/JP02/11884

§ 371 (c)(1),
(2), (4) Date: May 14, 2004

(87) PCT Pub. No.: WO03/042383

PCT Pub. Date: May 22, 2003

(65) Prior Publication Data

US 2005/0069887 A1 Mar. 31, 2005

(30) Foreign Application Priority Data

Nov. 14, 2001 (JP) ............................. 2001-349173
Oct. 25, 2002 (JP) ............................. 2002-311596

(51) Int. Cl.
C12Q 1/68 (2006.01)
C12P 19/34 (2006.01)
C12N 9/00 (2006.01)
C08B 3/00 (2006.01)

(52) U.S. Cl. .................. 435/6; 435/91.1; 435/183; 536/63

(58) Field of Classification Search .............. None
See application file for complete search history.

(56) References Cited

U.S. PATENT DOCUMENTS 5,677,152 A 10/1997 Birch et al.
5,773,258 A 6/1998 Birch et al.
6,114,150 A 9/2000 Weissman et al.
6,468,775 B1 * 10/2002 Ankenbauer et al. ........ 435/194

FOREIGN PATENT DOCUMENTS

| CA | 2 379 165 A1 | 2/2001 |
|---|---|---|
| DE | 44 11 588 C1 | 9/1995 |
| EP | 0 726 310 A1 | 8/1996 |
| EP | 0 745 675 A2 | 12/1996 |
| EP | 0 771 870 A1 | 5/1997 |
| EP | 0 870 832 A1 | 10/1998 |
| EP | 0 997 530 A1 | 5/2000 |
| WO | WO 92/08807 A1 | 5/1992 |
| WO | WO 95/20682 A1 | 8/1995 |
| WO | WO 96/34115 A1 | 10/1996 |
| WO | WO 98/45452 A2 | 10/1998 |
| WO | WO 98/45452 A3 | 10/1998 |
| WO | WO 99/46400 A1 | 9/1999 |
| WO | WO 01/09347 A2 | 2/2001 |
| WO | WO 01/09347 A3 | 2/2001 |
| WO | WO 01/11051 A2 | 2/2001 |
| WO | WO 01/11051 A3 | 2/2001 |

OTHER PUBLICATIONS

Kovarova et al. New specificity and yield enhancer of polymerase chain reactions. Nucleic Acid Res. (2000) 28:e70, pp. i-iv.*
Baskaran et al. Uniform amplification of a mixture of deoxyribonucleic acids with varying GC content. Genome Methods (1996) 6:633-638.*
Henneke et al., *Biochemical and Biophysical Research Communications*, 276(2), pp. 600-606 (2000).
Kitabayashi et al., *Bioscience, Biotechnology, and Biochemistry*, 66(10), pp. 2194-2200 (2002).
Ouhammouch et al., *Proc. Natl. Acad. Sci. USA*, 94(13): 6718-6723 (Jun. 1997).
Podust et al., *The Journal of Biological Chemistry*, 273(48): 31992-31999 (Nov. 27, 1998).
Kohjimoto et al., *Kidney International*, 58(2): 638-646 (Aug. 2000).
Nishioka et al., *Journal of Biotechnology*, 88: 141-149 (Jun. 2001).
Takagi et al., *Applied and Environmental Microbiology*, 63(11): 4504-4510 (Nov. 1997).

* cited by examiner

*Primary Examiner*—Kenneth R. Horlick
*Assistant Examiner*—David C Thomas
(74) *Attorney, Agent, or Firm*—Leydig, Voit & Mayer, Ltd.

(57) ABSTRACT

The invention provides methods, kits, and compositions for enhancing synthesis of DNA involving a carboxylate ion-supplying substance that is effective in promoting DNA synthesis in enzymatic DNA synthesis reactions. The invention further provides a thermostable DNA polymerase-related factor derived from *Thermococcus* species, which has an activity to promote the DNA synthesis activity of DNA polymerase or which binds to DNA polymerase.

42 Claims, 34 Drawing Sheets

EX-Taq 1.0U
 buffer supplied with EX-Taq
human genomic DNA 20ng
Target: myosin heavy chain 8.4kb

(COOK)$_2$ (mM)
0  1  2  3  4  5  10  M

M: λ /HindIII digest

Taq 2.5U
buffer supplied with EX-Taq
human genomic DNA 20ng
Target: $\beta$-globin 3.6kb $(COOK)_2$ (mM)

M: $\lambda$ /HindIIIdigest

Taq 2.5U
buffer supplied with EX-Taq
human genomic DNA 20ng
Target: myelin oligodendrocyte glycoprotein 4.5kb $(COOK)_2$ (mM)

M: λ /HindIIIdigest

Target: myosin heavy chain 8.4kb
KOD-Plus 1.0U
buffer supplied with KOD-plus
human genomic DNA 20ng

M: λ /HindIII digest

Target: myosin heavy chain 8.4kb
KOD-Plus 1.0U
buffer supplied with KOD-plus
human genomic DNA 20ng N : No salts added
A : KCl
B : $CH_3COOK$
C : HCOOK
D : $(COOK)_2$
E : $(COONa)_2$
F : $(CH_3COOK)_2$
G : $K_2SO_4$
M: λ/HindIIIdigest

EX-Taq 1.0U
buffer supplied with EX-Taq
+2mM potassium oxalate
human genomic DNA 20ng
Target: myosin heavy chain 8.4kb 1: Betaine  0mM
2:         0.5mM
3:         1.0mM
4:         1.5mM

M: λ /HindIII digest

Pfu 2.5U
buffer supplied with Pfu
+2mM potassium oxalate
human genomic DNA 20ng
Target: β-globin 3.6kb 1: Betaine   0mM
2:           0.5mM
3:           1.0mM
4:           1.5mM

M: λ /HindIII digest

KOD-Plus 1.0U
buffer supplied with KOD-Plus
+2mM potassium oxalate
human genomic DNA 20ng
Target: myosin heavy chain 8.4kb 1: Betaine    0mM
2:               0.5mM
3:               1.0mM
4:               1.5mM M: λ /HindIII digest

KOD-Plus 1.0U
buffer supplied with KOD-Plus
+2mM potassium oxalate
Target: insulin-like growth factor receptor II  8.8kb

1:DMSO  0%
2:       2%
3:       5%

M: λ /HindIII digest

KOD 2.0U
buffer supplied with KOD-Plus
+2mM potassium oxalate
Target: β-globin 21.5kb 1: Betaine 0.8M
2: 1.0M
3: 1.2M
4: 1.4M
5: 1.6M M: λ /HindIII digest

KOD 2.0U buffer supplied with KOD-Plus
+1.5M betaine

| Target | tPA 22kb | tPA 24kb | |
|---|---|---|---|
| | 1 2 3 4 | 5 6 7 8 | M |

1,5 : K oxalate 1.0mM
2,6 :           1.5mM
3,7 :           2.0mM
4,8 :           2.5mM M: λ /HindIII digest

KOD 2.0U
buffer supplied with KOD-Plus
+2mM potassium oxalate+1.5M betaine antibody(−)   antibody(+)

1 2 3 4 5 6  M  7 8 9 10 11 12

M: λ /HindIII digest

Target
1, 7 : tPA 12kb       4,10 :   22kb
2, 8 :    15kb        5,11 :   24kb
3, 9 :    18kb        6,12 : β-globin 17.5kb

Fig. 21

| Domain | II | III | IV |

Mth : PWVEKYRPQKL PHLLPTGPAGVGKTTA LELNASD
KOD : PWVEKYRPQRL PHLLFAGPPGVGKITTA LELNASD

Intein

| Domain | V | VIb | VII | VIII |

Mth : FRIIFLDEVD NMTKDAQHALRREME SRC GDLRKAINLL
KOD : FKIIFLDEAD ALTQDAQQALRRTME SRC GDLRRAINVL

Mth : *Methanobacterium thermoautotrophicum*

(A)

(B)

(10% SDS-PAGE)

(A)

精製フロー

(B)

RFC : 227.4kD    PCNA : 87.1kD

M: λ /HindIII digest

Template : primed M13 ccDNA
KOD : Template = 1:10

M: λ /HindIII digest

Template : 800fmol primed M13 ssDNA
KOD : 120fmol (0.5U)
PCNA : 3pmol
RFC : 5.6pmol M: λ/HindIIIdigest Target: β-globin 3.6kb
KOD 1U (250fmoles)
buffer supplied with KOD-plus Target: $\beta$-globin 3.6kb
KOD 1U (250fmoles)
buffer supplied with KOD-plus M: $\lambda$/HindIII digest 1 : KOD
2 : KOD:RFC = 1 : 1 (250fmoles)
3 : KOD:RFC = 1 : 3 (750fmoles)
4 : KOD:RFC = 1 : 6 (1500fmoles)

KOD 1U (250fmoles)
target: β-globin 3.6kb

M: λ /HindIII digest

1 : KOD:PCNA       = 1 : 1/25      (PCNA 10fmoles)
2 : KOD:PCNA:RFC = 1 : 1/25 : 1  (RFC 250fmoles)
3 : KOD:PCNA:RFC = 1 : 1/25 : 3  (RFC 750fmoles)
4 : KOD:PCNA:RFC = 1 : 1/25 : 6  (RFC 1500fmoles)

Target: β-globin 3.6kb
KOD Dash 1U (250fmoles)
buffer supplied with KOD-plus

M: λ /HindIII digest

1 : KOD
2 : KOD:PCNA = 1 : 1/3 (80fmoles)
3 : KOD:PCNA:RFC = 1 : 1/3 : 1/3 (80fmoles each)

Description of symbols in Figures

T7p exhibits T7 promoter, RBS exhibits ribosome binding site and T7t exhibits T7 terminator in Figs. 23, 24 and 25.

ns of DNA and a DNA polymerase-related factor that are useful for DNA synthesis and DNA amplification from template nucleic acids, and so on. More specifically, the invention relates to a composition for enhancing synthesis of DNA and a DNA polymerase-related factor that are useful for polymerase chain reactions (PCR), and so on.

BACKGROUND ART

The DNA amplification technique represented by polymerase chain reactions (PCR); Nature, vol. 324 (6093), 1986, pp.13-19) is a well-known technique in the field of molecular biology. Detection, analysis, transcription or amplification of nucleic acids by the PCR technique is one of the most important operations in modern molecular biology and is especially important in gene expression studies, diagnosis of infectious agents or hereditary diseases, cDNA production, analysis of retroviruses, etc.

Since DNA amplification performance depends on the performance of the DNA polymerase used, various DNA polymerases have been searched for in nature or improved. For example, PCR was originally performed using insufficiently thermostable DNA polymerases derived from mesophiles such as *E. coli*. However, since PCR is performed under highly stringent conditions, i.e., themocycling at temperatures in the range of about 23° C. to about 100° C. many times, the success rate (probability with which object DNA is successfully amplified) was low. It is now, however, common practice to utilize highly thermostable thermophile-derived DNA polymerases.

One of the important performances required of DNA polymerases is "elongation rate". A typical method of determining DNA elongation rate comprises performing a DNA synthesis reaction in a buffer using DNA prepared by annealing of M13 single-stranded DNA (1.6 μg) and complementary primer(s) (16 pmole) as a template and using KOD, Pfu, Deep Vent, Taq or like various DNA polymerases (5U) (as an enzyme), followed by calculating the DNA elongation rate from the relationship between the reaction time and the size of DNA synthesized.

For example, the DNA elongation rate of KOD polymerase is 105 to 130 bases/second, that of Pfu polymerase is 24.8 bases/second, that of Deep Vent polymerase is 23.3 bases/second, and that of Taq polymerase is 61.0 bases/second (Takagi, M. et al.: Characterization of DNA polymerase from *Pyrococcus* sp. KOD1 and its application to PCR; Appl. Environ. Microbiol. 63, 4504-45410, (1997)).

"Fidelity" is another important performance required of DNA polymerases. One example of a method for evaluating the DNA synthesis fidelity of DNA polymerase is using a ribosomal protein S12 (rpsL) gene associated with streptomycin resistance. Streptomycin is an antibiotic that inhibits protein synthesis in prokaryote. This antibiotic binds to bacterial 30S ribosomal RNA (rRNA) to inhibit initiation complex for protein synthesis formation reactions and cause the misreading of genetic code. Streptomycin-resistant strains have a mutation at the ribosomal protein S12 locus. This mutation is known to produce pleiotropic effects such as inhibiting suppressor tRNA from reading the stop codon to enhance translation fidelity of the ribosome. Thus, when PCR amplification is carried out using rpsL gene as a template, a mutation is introduced with a certain probability. When the mutation occurs at the amino acid level, the rpsL protein structure is changed so that streptomycin cannot act on 30S ribosomal RNA (rRNA). Therefore, when the amplified plasmid DNA is used to transform *E. coli*, the more mutations introduced, the higher the frequency of streptomycin-resistant strain appearance.

The plasmid pMol 21 (described in *Journal of Molecular Biology* (1999) 289, 835-850) is a plasmid containing rpsL gene and ampicillin resistant gene. A primer set for PCR amplification (one of the primers is biotinylated and has a MluI restriction site introduced therein) is designed on the ampicillin resistant gene of the plasmid pMol 21 to amplify the full-length plasmid by PCR using a thermostable DNA polymerase. The obtained PCR product is purified using streptavidin beads and cut out using the restriction enzyme MluI, followed by ligating the ends using DNA ligase to transform *E. coli*. The transformant is inoculated into two types of plate media, i.e., one containing ampicillin, and the other containing both ampicillin and streptomycin. The ratio of numbers of colonies appearing on the two plate media is calculated to determine the fidelity or correctness of DNA synthesis (Kunkel, Journal of Biological Chemistry, vol. 260, 1985, pp.5787-5796).

When PCR product fidelity of Taq DNA polymerase is determined by the above method of determining DNA synthesis fidelity, the mutation rate was 4% or more. In the case of a DNA polymerase capable of exhibiting 3'-5' exonuclease activity when used alone, the mutation rate was 0.05 to 1%. When using a mixed enzyme of an enzyme not having 3'-5' exonuclease activity such as Taq DNA polymerase and an enzyme having 3'-5' exonuclease activity, the mutation rate was 2 to 4%. The mutation rate achieved by KOD DNA polymerase was 0.1% or less. This DNA polymerase is the most suitable enzyme for obtaining high-fidelity PCR products.

To what length the target DNA can be amplified (hereinafter referred to as "long-PCR performance") is also an important requirement of DNA polymerases.

DNA polymerases, kinds of thermostable (or heat-resistant) DNA polymerases, are roughly classified into Pol I-type enzymes represented by Taq DNA polymerase and Tth DNA polymerase, and α-type enzymes represented by Pfu DNA polymerase. Generally, Pol I-type enzymes achieve high DNA elongation rates but have poor fidelity because of the lack of 3'-5' exonuclease activity. In contrast, α-type enzymes, which possess 3'-5' exonuclease activity, have high fidelity but achieve low DNA elongation rates. Thus, although the two types of DNA polymerases have excellent properties in "elongation rate" and "fidelity", respectively, neither have both.

With the purpose of combining the merits of both types of enzymes, Proc. Natl. Acad. Sci. USA, vol.91, 1994, pp.2216-2220 describes a technique utilizing a mixed type enzyme prepared by mixing two kinds of thermostable enzymes. This enzyme mostly comprises a Pol I-type enzyme, which is considered to mainly perform DNA biosynthesis, while the α-type enzyme merely proofreads base errors.

Japanese Patent Publication No. 3112148 describes KOD DNA polymerase, a single enzyme (α-type enzyme) having both excellent "elongation rate" and "fidelity".

A method using HindIII-digested λDNA labeled with $^3H$ at the 3' end as a substrate and measuring the rate of $^3H$ release under the optimal temperatures for each polymerase is known as a typical method of evaluating 3'-5' exonuclease activity. More specifically, using a HindIII-digested λDNA fragment having [$^3$H] TTP incorporated therein as a substrate, for example, the DNA fragment and a polymerase are left in a buffer solution (20 mM Tris-HCl pH 6.5, 10 mM KCl, 6 mM $(NH_4)_2SO_4$, 2 mM $MgCl_2$, 0.1% Triton X-100, 10 µg/ml BSA) under the optimal conditions for the polymerase and the [$^3$H]TTP release rate is determined. The substrate DNA is prepared by adding 0.2 mM of dATP, dGTP, dCTP and [$^3$H] TTP to 10 µg of HindIII-cleaved λDNA and extending the 3' end with Klenow polymerase, followed by phenol extraction and ethanol precipitation to recover the DNA fragment and further purification by removal of the released mononucleotides using a spun column (product of Clontech).

To improve DNA amplification performance, various studies have been conducted to improve the composition of DNA synthesis reaction solutions. Examples of tested buffers include Tris, Tricine, bis-Tricine, HEPES, MOPS, TES, TAPS, PIPES, CAPS, etc. Examples of tested salts include potassium chloride, potassium acetate, potassium sulfate, ammonium sulfate, ammonium chloride, ammonium acetate, magnesium chloride, magnesium acetate, magnesium sulfate, manganese chloride, manganese acetate, manganese sulfate, sodium chloride, sodium acetate, lithium chloride, lithium acetate, etc. Examples of tested additives include DMSO, glycerol, formamide, betaine, tetramethylammonium chloride, PEG, Tween 20, NP40, ectoine, polyols, E. coli SSB protein, phage T4 gene 32 protein and BSA, etc (Published Japanese Translation of PCT International Publication of Patent Application No. H9(1997)-511133, U.S. Pat. No. 5,545,539, International Publication No. WO 96/12041, U.S. Pat. No. 6,114,150, WIPO Publication No. WO 99/46400, Nucleic Acids Research, vol. 23, 1995, pp.3343-3344, and Nucleic Acids Research, vol. 28, 2000, p.70).

However, the above reagents are not effective for all DNA polymerases. Effectivity depends on the enzyme. Therefore, different reaction solution compositions have been investigated for different enzymes, and optimal reaction buffer solutions for individual enzymes have been recommended. It has been considered impossible to achieve a higher amplification efficiency than commercially co-packaged buffer solutions.

With the recent advances in biotechnology, the required performance levels in DNA amplification, especially PCR, of "elongation rate", "fidelity" and "long-PCR performance" have been raised ever upwards. In particular, DNA amplification fidelity has become more important in that successful elucidation of the entire human genome sequence has shifted the focus of study from mere detection of genes or analysis of their differences to analysis of the functions of genes or proteins encoded by the genes.

Therefore, the establishment of a DNA amplification method achieving these requirements has been desired, but none of the prior art is satisfactory for practical use in all the requirements "elongation rate", "fidelity" and "long-PCR performance".

DISCLOSURE OF THE INVENTION

An object of the invention is to provide a composition for enhancing synthesis of DNA and a DNA polymerase-related factor which enhance "elongation rate", "fidelity" and/or "long-PCR performance" in DNA synthesis, etc.

The present inventors have carried out intensive research to achieve the above object and found the followings:

i) Anionic substances are also important in determining the success or failure of PCR, although research in the prior art has been carried out focusing on cations ($K^+$, $Na^+$, $NH_4^+$, etc.) from the viewpoint of their activity on nucleic acids. More specifically, PCR success rate is enhanced by addition of carboxylate ion-supplying substances, in particular dicarboxylic acid salts or esters, to a PCR solution.

ii) Among bivalent carboxylate ions, oxalate ion, malonate ion and maleate ion are particularly effective. Among dicarboxylic acid salts or esters, dicarboxylic acid inorganic salts are particularly effective.

iii) DNA amplification efficiency is further enhanced by combining such anionic substances with at least one compound selected from the group consisting of dimethylsulfoxide and compounds represented by formula (1) shown below, thus achieving synergetic effects. Among the compounds of formula (1), trimethylglycine is particularly effective.

Successful high GC content PCR target DNA amplification and succeeds in hitherto impossible long chain target DNA amplification, etc. can be mentioned as synergetic DNA amplification improvements. Moreover, enhancement in PCR amplification amount is also one of the synergistic effects of the invention.

iv) The present inventors isolated a DNA polymerase-related factor from the hyperthermophilic archaeon *Thermococcus kodakaraensis* KOD1 and found that this factor can promote the DNA synthesis activity of DNA polymerase and can bind to DNA polymerase. The inventors succeeded in massive expression of the gene encoding the DNA polymerase-related factor, which enables industrial scale production of the factor.

The present invention has been accomplished based on the above findings, and provides the following compositions for enhancing synthesis of DNA, DNA polymerase-related factors, etc.

1. A composition for enhancing synthesis of DNA comprising at least one anion-supplying substance that is effective in promoting DNA synthesis in enzymatic DNA synthesis reactions.

2. A composition for enhancing synthesis of DNA according to item 1 wherein the anion is a carboxylate ion.

3. A composition for enhancing synthesis of DNA according to item 2 wherein the carboxylate ion-supplying substance is a salt of a dicarboxylic acid.

4. A composition for enhancing synthesis of DNA according to item 3 wherein the dicarboxylic acid salt is an inorganic salt.

5. A composition for enhancing synthesis of DNA according to item 4 wherein the inorganic salt of dicarboxylic acid is an alkali metal salt, alkaline earth metal salt or ammonium salt of dicarboxylic acid.

6. A composition for enhancing synthesis of DNA according to item 3 wherein the dicarboxylic acid salt is an oxalic acid salt, a malonic acid salt or a maleic acid salt.

7. A composition for enhancing synthesis of DNA according to item 2 wherein the carboxylate ion-supplying substance is an ester of a dicarboxylic acid.

8. A composition for enhancing synthesis of DNA according to item 7 wherein the dicarboxylic acid ester is an oxalic acid ester, a malonic acid ester or a maleic acid ester.

9. A composition for enhancing synthesis of DNA comprising:

i) at least one anion-supplying substance that is effective in promoting DNA synthesis in enzymatic DNA synthesis reactions; and ii) at least one compound selected from the group consisting of dimethylsulfoxide and compounds represented by the following formula

 (1)

wherein $R^1$ is an alkyl group having 1 to 3 carbon atoms, $R^2$ is a substituent selected from the group consisting of the following (a) and (b):
(a) =O (oxygen) and (b) radicals represented by the formula

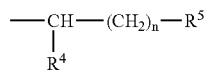

wherein $R^4$ is methyl, hydrogen and forms a pyrrolidine ring when combined with $R^1$, $R^5$ is —$CO_2H$ or —$SO_3H$, and n is an integer from 0 to 2,
x is an integer from 1 to 3 and
y is an integer from 0 to 2, provided that x plus y equals 3.

10. A composition for enhancing synthesis of DNA according to item 9 wherein the anion is a carboxylate ion.

11. A composition for enhancing synthesis of DNA according to item 10 wherein the carboxylate ion-supplying substance is a salt of a dicarboxylic acid.

12. A composition for enhancing synthesis of DNA according to item 11 wherein the dicarboxylic acid salt is an inorganic salt.

13. A composition for enhancing synthesis of DNA according to item 12 wherein the inorganic salt is an alkali metal salt, alkaline earth metal salt or ammonium salt.

14. A composition for enhancing synthesis of DNA according to item 11 wherein the dicarboxylic acid salt is an oxalic acid salt, a malonic acid salt or a maleic acid salt.

15. A composition for enhancing synthesis of DNA according to item 10 wherein the carboxylate ion-supplying substance is an ester of a dicarboxylic acid.

16. A composition for enhancing synthesis of DNA according to item 15 wherein the dicarboxylic acid ester is an oxalic acid ester, a malonic acid ester or a maleic acid ester.

17. A composition for enhancing synthesis of DNA according to item 9 wherein the compound of formula (1) is trimethylglycine.

18. A composition for enhancing synthesis of DNA containing the compound of formula (1) in an amount to achieve a concentration of 0.5 to 2M in DNA synthesis reactions, and/or containing dimethylsulfoxide in an amount to achieve a concentration of 0.1 to 15 wt. % in DNA synthesis reactions.

19. A thermostable DNA polymerase-related factor derived from a *Thermococcus* species, which promotes the DNA synthesis activity of a DNA polymerase.

20. A DNA polymerase-related factor according to item 19 wherein the *Thermococcus* species is a hyperthermophilic archaeon, *Thermococcus kodakaraensis*.

21. A DNA polymerase-related factor according to item 20 wherein the strain of *Thermococcus kodakaraensis* is *Thermococcus kodakaraensis* KOD1.

22. A DNA polymerase-related factor according to item 19 which promotes the DNA synthesis activity of a thermostable DNA polymerase.

23. A DNA polymerase-related factor according to item 19 which promotes the DNA synthesis activity of a DNA polymerase derived from a *Thermococcus* species.

24. A DNA polymerase-related factor according to item 23 wherein the *Thermococcus* species is the hyperthermophilic archaeon *Thermococcus kodakaraensis*.

25. A DNA polymerase-related factor according to item 24 wherein the strain of *Thermococcus kodakaraensis* is *Thermococcus kodakaraensis* KOD1.

26. A thermostable DNA polymerase-related factor derived from a *Thermococcus* species, which has an activity to bind to DNA polymerase.

27. A DNA polymerase-related factor according to item 26 wherein the *Thermococcus* species is the hyperthermophilic archaeon *Thermococcus kodakaraensis*.

28. A thermostable DNA polymerase-related factor according to item 27 wherein the strain of *Thermococcus kodakaraensis* is *Thermococcus kodakaraensis* KOD1.

29. A DNA polymerase-related factor according to item 26 which has an activity to bind to a thermostable DNA polymerase.

30. A DNA polymerase-related factor according to item 26 which promotes the DNA synthesis activity of a DNA polymerase derived from a *Thermococcus* species.

31. A DNA polymerase-related factor according to item 30 wherein the *Thermococcus* species is the hyperthermophilic archaeon *Thermococcus kodakaraensis*.

32. A DNA polymerase-related factor according to item 31 wherein the strain of *Thermococcus kodakaraensis* is *Thermococcus kodakaraensis* KOD1.

33. A DNA polymerase-related factor which is KOD-PCNA (proliferating cell nuclear antigen) derived from *Thermococcus kodakaraensis* KOD1, KOD-RFCS (replication factor C small subunit) derived from *Thermococcus kodakaraensis* KOD1, or KOD-RFCL (replication factor C large subunit) derived from *Thermococcus kodakaraensis* KOD1.

34. Any one of the proteins shown in (e) to (j) below:
(e) a protein comprising the amino acid sequence of SEQ ID NO: 2;
(f) a protein which comprises an amino acid sequence resulting from addition, deletion or substitution of one or more amino acids in the sequence of SEQ ID NO: 2, and has an activity to promote the DNA synthesis activity of a DNA polymerase or an activity to bind to a DNA polymerase;
(g) a protein comprising the amino acid sequence of SEQ ID NO: 4;
(h) a protein which comprises an amino acid sequence resulting from addition, deletion or substitution of one or more amino acids in the sequence of SEQ ID NO: 4, and has an activity to promote the DNA synthesis activity of a DNA polymerase or an activity to bind to a DNA polymerase;
(i) a protein comprising the amino acid sequence of SEQ ID NO: 6;
(j) a protein which comprises an amino acid sequence resulting from addition, deletion or substitution of one or more amino acids in the sequence of SEQ ID NO: 6, and has an activity to promote the DNA synthesis activity of a DNA polymerase or an activity to bind to a DNA polymerase.

35. Any one of the genes shown in (k) to (p) below:
(k) a gene comprising the nucleotide sequence of SEQ ID NO: 3;
(l) a gene which hybridizes with the gene consisting of the nucleotide sequence of SEQ ID NO: 3 under stringent conditions, and has an activity to promote the DNA synthesis activity of a DNA polymerase or an activity to bind to a DNA polymerase;

(m) a gene comprising the nucleotide sequence of SEQ ID NO: 5;
(n) a gene which hybridizes with the gene consisting of the nucleotide sequence of SEQ ID NO: 5 under stringent conditions, and has an activity to promote the DNA synthesis activity of a DNA polymerase or an activity to bind to a DNA polymerase;
(o) a gene comprising the nucleotide sequence of SEQ ID NO: 7;
(p) a gene which hybridizes with the gene consisting of the nucleotide sequence of SEQ ID NO: 7 under stringent conditions, and has an activity to promote the DNA synthesis activity of a DNA polymerase or an activity to bind to a DNA polymerase.

36. A process for preparing a DNA polymerase-related factor, comprising culturing a transformant harboring the DNA of item 35 and recovering a thermostable DNA polymerase-related factor from the culture, the DNA polymerase-related factor having an activity to either promote the DNA synthesis activity of a DNA polymerase or bind to a DNA polymerase, or having both activities.

37. A composition for synthesizing DNA comprising the composition for enhancing synthesis of DNA of any of items 1 to 18 and an enzyme having DNA polymerase activity.

38. A composition for synthesizing DNA according to item 37 which further comprises the DNA polymerase-related factor of any of items 19 to 33 or the protein of item 34.

39. A composition for synthesizing DNA according to item 37 wherein the enzyme having DNA polymerase activity is a DNA-directed DNA polymerase.

40. A composition for synthesizing DNA according to item 39 wherein the DNA-directed DNA polymerase is selected from the group consisting of Taq polymerase, Tth polymerase, Tli polymerase, Pfu polymerase, Pfutubo polymerase, Pyrobest polymerase, Pwo polymerase, KOD polymerase, Bst polymerase, Sac polymerase, Sso polymerase, Poc polymerase, Pab polymerase, Mth polymerase, Pho polymerase, ES4 polymerase, VENT polymerase, DEEPVENT polymerase, EX-Taq polymerase, LA-Taq polymerase, Expand polymerases, Platinum Taq polymerases, Hi-Fi polymerase, Tbr polymerase, Tfl polymerase, Tru polymerase, Tac polymerase, Tne polymerase, Tma polymerase, Tih polymerase, Tfi polymerase, and variants, modified products and derivatives thereof.

41. A composition for synthesizing DNA according to item 39 wherein the DNA-directed DNA polymerase is a thermostable DNA-directed DNA polymerase which synthesizes DNA at a rate of at least 30 bases/second and has 3'-5' exonuclease activity.

42. A composition for synthesizing DNA according to item 39 wherein the DNA-directed DNA polymerase is a thermostable DNA-directed DNA polymerase which synthesizes DNA at a rate of at least 30 bases/second and which exhibits an error rate of 4% or less when performing PCR using mMOl 21 as a template.

43. A composition for synthesizing DNA according to item 37 wherein the enzyme having DNA polymerase activity is a reverse transcriptase.

44. A composition for synthesizing DNA according to item 43 wherein the reverse transcriptase is an enzyme selected from the group consisting of AMV-RT polymerase, M-MLV-RT polymerase, HIV-RT polymerase, EIAV-RT polymerase, RAV2-RT polymerase, *C. hydrogenoformans* DNA polymerase, SuperScript I, SuperScript II, and variants, modified products and derivatives thereof.

45. A composition for synthesizing DNA according to item 43 wherein the reverse transcriptase is an enzyme with substantially reduced RnaseH activity.

46. A composition for synthesizing DNA according to item 37, further comprising at least one member selected from the group consisting of nucleotides, nucleotide derivatives, buffers, salts, template nucleic acids and primers.

47. A composition for synthesizing DNA according to item 46 wherein the nucleotides are deoxyphosphonucleotides and nucleotide derivatives are deoxyphosphonucleotide derivatives.

48. A composition for synthesizing DNA according to item 47 wherein the deoxyphosphonucleotides and derivatives thereof are selected from the group consisting of dATP, dCTP, dGTP, dTTP, dITP, dUTP, α-thio-dNTPs, biotin-dUTP, fluorescein-dUTP and digoxigenin-dUTP.

49. A method for synthesizing DNA comprising the steps of:
(a) mixing a template nucleic acid with the composition of any of claims 8 to 15, a nucleotide and/or a nucleotide derivative, and primers to form a mixture; and
(b) incubating the mixture under such conditions that DNA is synthesized at a rate of at least 30 bases/second and, when performing PCR using pMol 21 as a template, the error rate is 4% or less to prepare a first nucleic acid molecule complementary to the entire or part of the template nucleic acid.

50. A method for synthesizing DNA according to item 49 wherein the template nucleic acid is a purified nucleic acid.

51. A method for synthesizing DNA according to item 50 wherein the template nucleic acid is a nucleic acid purified by a method comprising the following steps:
(i) mixing a nucleic acid-binding magnetic carrier consisting of ferromagnetic metal oxide-containing magnetic silica particles, a nucleic acid-containing material and a nucleic acid extraction solution;
(ii) separating the nucleic acid-bound magnetic carrier from the residual mixture using a magnetic field; and
(iii) eluting the nucleic acid from the magnetic carrier.

52. A method for synthesizing DNA according to item 49 further comprising the step of (c) incubating a mixture containing the first nucleic acid molecule under such conditions that DNA is synthesized at a rate of at least 30 bases/second and, when performing PCR using pMol 21 as a template, the error rate is 4% or less to prepare a second nucleic acid molecule complementary to the entire or part of the first nucleic acid molecule.

53. A method for synthesizing DNA according to item 49 further comprising the step of (d) purifying the synthesized DNA.

54. A method for synthesizing DNA according to item 53 wherein the DNA purification step (d) comprises the following steps:
(iv) mixing a nucleic acid-binding magnetic carrier consisting of ferromagnetic metal oxide-containing magnetic silica particles, a material comprising the synthesized DNA, and a nucleic acid extraction solution;
(v) separating the DNA-bound magnetic carrier from the residual mixture using a magnetic field; and
(vi) eluting the nucleic acid from the magnetic carrier.

55. A method for synthesizing DNA according to any of items 49 to 54 using hot start PCR.

56. A nucleic acid molecule obtained by the method of item 49.

57. A DNA amplification method comprising the steps of:
(a) mixing a template nucleic acid with the composition of any of items 37 to 45, nucleotide and/or nucleotide derivatives and primers to form a mixture; and
(b) incubating the mixture under such conditions that DNA is synthesized at a rate of at least 30 bases/second and, when performing PCR using pMol 21 as a template, the error rate is 4% or less to amplify a nucleic acid molecule complementary to the entire or part of the template nucleic acid.

58. A DNA amplification method according to item 57 wherein the template nucleic acid is a purified nucleic acid.

59. A DNA amplification method according to item 58 wherein the template nucleic acid is a nucleic acid purified by a method comprising the following steps:
(i) mixing a nucleic acid-binding magnetic carrier consisting of magnetic silica particles containing ferromagnetic metal oxide, a nucleic acid-containing material, and a nucleic acid extraction solution;
(ii) separating the nucleic acid-bound magnetic carrier from the residual mixture using a magnetic field; and
(iii) eluting the nucleic acid from the magnetic carrier.

60. A DNA amplification method according to item 57 further comprising the step of (c) incubating a mixture containing the first nucleic acid molecule under such conditions that DNA is synthesized at a rate of at least 30 bases/second and, when performing PCR using pMol 21 as a template, the error rate is 4% or less to prepare a second nucleic acid molecule complementary to the entire or part of the first nucleic acid.

61. A DNA amplification method according to item 57 further comprising the step of (d) purifying the synthesized DNA.

62. A DNA amplification method according to item 61 wherein the DNA purification step (d) comprises the following steps:
(iv) mixing a nucleic acid-binding magnetic carrier consisting of ferromagnetic metal oxide-containing magnetic silica particles, a material comprising the synthesized DNA, and a nucleic acid extraction solution;
(v) separating the DNA-bound magnetic carrier from the residual mixture using a magnetic field; and
(vi) eluting the nucleic acid from the magnetic carrier.

63. A DNA amplification method according to any of items 57 to 62 using hot start PCR.

64. A method for nucleotide sequencing comprising the steps of:
(a) mixing a target nucleic acid with the composition of any of items 37 to 45, nucleotide and/or nucleotide derivatives, primers and a release factor to form a mixture;
(b) incubating the mixture under such conditions that DNA is synthesized at a rate of at least 30 bases/second and, when performing PCR using pMol 21 as a template, the error rate is 4% or less to amplify a nucleic acid molecule complementary to the entire or part of the target nucleic acid; and
(e) separating the amplified nucleic acid molecule to determine the entire or partial nucleotide sequence.

65. A method for nucleotide sequencing according to item 64 wherein the target nucleic acid is a purified nucleic acid.

66. A method for nucleotide sequencing according to item 65 wherein the target nucleic acid is a nucleic acid purified by a method comprising the following steps:
(i) mixing a nucleic acid-binding magnetic carrier consisting of ferromagnetic metal oxide-containing magnetic silica particles, a nucleic acid-containing material and a nucleic acid extraction solution;
(ii) separating the nucleic acid-bound magnetic carrier from the residual mixture using a magnetic field; and
(iii) eluting the nucleic acid from the magnetic carrier.

67. A method for nucleotide sequencing according to item 64 further comprising, between steps (b) and (e) (or between steps (b) and (d) when the process further comprises step (d)), the step of (c) incubating a mixture containing a first nucleic acid molecule under such conditions that DNA is synthesized at a rate of at least 30 bases/second and, when performing PCR using pMol 21 as a template, the error rate is 4% or less to prepare a second nucleic acid molecule complementary to the entire or part of the first nucleic acid molecule.

68. A method for nucleotide sequencing according to item 64 further comprising, between steps (b) and (e) (or between steps (c) and (e) when the process further comprises step (c)), the step of (d) purifying the synthesized DNA.

69. A method for nucleotide sequencing according to item 68 wherein the DNA purification step (d) comprises the following steps:
(iv) mixing a nucleic acid-binding magnetic carrier consisting of ferromagnetic metal oxide-containing magnetic silica particles, a material comprising the synthesized DNA, and a nucleic acid extraction solution;
(v) separating the DNA-bound magnetic carrier from the residual mixture using a magnetic field; and
(vi) eluting the nucleic acid from the magnetic carrier.

70. A method for nucleotide sequencing according to any of items 64 to 69 using hot start PCR.

71. A kit for synthesizing DNA molecule comprising the DNA synthesizing composition of any of items 37 to 48.

72. A kit for synthesizing DNA molecule according to item 71 wherein the components are entirely contained in one part or separately contained in two or more parts.

73. A method for synthesizing DNA comprising reacting a DNA polymerase with a template nucleic acid in the presence of the DNA polymerase-related factor of any of items 19 to 33 or the protein of item 34.

74. A method for synthesizing DNA according to item 73 using at least two members selected from the group consisting of the DNA polymerase-related factors of items 19 to 33 and proteins of item 34.

75. A DNA synthesis method according to item 73 wherein the DNA polymerase is a thermostable DNA polymerase.

76. A DNA synthesis method according to item 73 which is a PCR method.

77. A kit for synthesizing DNA comprising a DNA polymerase and the DNA polymerase-related factor of any of items 19 to 33 or the protein of item 34.

78. A kit for synthesizing DNA according to item 77 wherein the DNA polymerase is a thermostable DNA polymerase.

According to the invention, hitherto impossible target nucleic acid DNA syntheses become possible by utilizing an anion-supplying substance effective in promoting DNA synthesis. The invention enables not only simple DNA synthesis but also PCR to be performed on a target nucleic acid whose PCR was conventionally impossible, thus enhancing the PCR success rate. These effects are obtainable with all kinds of DNA polymerases.

According to the invention, the success rate of DNA synthesis, particularly the PCR success rate, is further enhanced by using the compound of formula (1) and/or DMSO in combination with the anion effective in promoting DNA synthesis, thus achieving synergetic effects. These synergetic effects are confirmed with several DNA polymerases and are effective for not only simple DNA synthesis reactions but also PCR methods. In particular, long PCR becomes possible even with α-type DNA polymerases which are considered to be unsuitable for long PCR. Further, by using hot start PCR, stable effectiveness for long PCR can be achieved.

Moreover, the invention enables mass production of DNA polymerase-related factor that enhances DNA synthesis activity of DNA polymerases. The DNA synthesis activity-promoting effect of the DNA polymerase-related factor is effective for not only simple DNA synthesis reactions but also PCR methods, thus making conventionally impossible PCR possible beyond the prior limitations, with each DNA polymerase, on the probability of PCR success, amplification amount enhancement and fidelity enhancement.

DETAILED DESCRIPTION OF THE INVENTION

The present invention is described below in detail.

(I) First Enhancing Composition for DNA Synthesis

The first enhancing composition for DNA synthesis of the invention is a composition for enhancing synthesis of DNA comprising at least one anion-supplying substance that is effective in promoting DNA synthesis in enzymatic DNA synthesis reactions.

Anion-Supplying Substance

The anion-supplying substance (anionic substance) that is effective in promoting DNA synthesis is not particularly limited and includes substances that have carboxyl groups and supply carboxylate ions. Salts and esters of dicarboxylic acids are preferable, and salts of dicarboxylic acids are particularly preferable. Inorganic salts of dicarboxylic acid salts are preferable, and alkali metal salts, alkaline earth metal salts and ammonium salts are particularly preferable. Among these, alkali metal salts are especially preferable and potassium salts or sodium salts are particularly preferable.

Usable dicarboxylic acids are not particularly limited and preferable examples include oxalic acid, malonic acid and maleic acid. Oxalic acid is particularly preferable.

Examples of dicarboxylic acid salts or esters include zinc oxalate, ammonium oxalate, potassium oxalate, calcium oxalate, diethyl oxalate, N,N'-disuccinimidyl oxalate, dimethyl oxalate, tin oxalate, cerium oxalate, iron oxalate, copper oxalate, sodium oxalate, nickel oxalate, bis oxalate, 2,4-dinitrophenyl oxalate, 2,4,6-trichlorophenyl oxalate, manganese oxalate, methyl oxalate, lanthanum oxalate, lithium oxalate, isopropylidene malonate, ethyl malonate, diethyl malonate, dibenzyl malonate, dimethyl malonate, thallium malonate, disodium malonate, monosodium maleate, diethyl maleate, chlorpheniramine maleate, di-n-butyl maleate, mono-n-butyl maleate; and the like. All these compounds are commercially available.

Preferably, the composition for enhancing synthesis of DNA contains such an anion-supplying substance in an amount to achieve a concentration in the DNA synthesis reaction solution of usually about 0.1 to 20 mM, preferably about 0.1 to 10 mM, and more preferably about 1 to 10 mM.

(II) Second Enhancing Composition for DNA Synthesis

The second enhancing composition for DNA synthesis of the invention is a composition for enhancing synthesis of DNA comprising:

i) at least one anion-supplying substance that is effective in promoting DNA synthesis in enzymatic DNA synthesis reactions; and
ii) at least one compound selected from the group consisting of dimethylsulfoxide and compounds represented by the following formula (1):

$$R^2-CH_2-NR^1{}_xH_y \qquad (1)$$

wherein $R^1$ is an alkyl group having 1 to 3 carbon atoms, $R^2$ is a substituent selected from the group consisting of the following (a) and (b):
(a) oxygen (=O) and (b) radicals represented by the formula $$-CH-(CH_2)_n-R^5$$
$$\phantom{-CH}|$$
$$\phantom{-CH}R^4$$

wherein $R^4$ is methyl or hydrogen, and forms a pyrrolidine ring when combined with $R^1$, $R^5$ is $-CO_2H$ or $-SO_3H$, and n is an integer from 0 to 2, x is an integer from 1 to 3 and y is an integer from 0 to 2, provided that x plus y equals 3.

Compound of Formula (1)

In the compound of formula (1), $R^1$ includes methyl, ethyl, n-propyl, isopropyl and the like. Methyl is particularly preferable. $R^2$ is preferably carboxyl. Especially preferable are trialkylglycines wherein x is 3 and y is 0. Particularly preferable is trimethylglycine (betaine). Commercially available trimethylglycines can be used.

The effective concentration of the compound of formula (1) in the DNA synthesis reaction solution is usually about 0.5 to 2M. Therefore, the composition for enhancing synthesis of DNA preferably contains the compound in an amount to achieve a concentration in the DNA synthesis reaction solution of about 0.5 to 2M, preferably about 0.5 to 1.5M, and more preferably 1 to 1.5M.

DMSO

Commercially available DMSO, etc. can be used. The effective concentration of DMSO in the DNA synthesis reaction system is usually about 0.1 to 15 volume %. Therefore, the composition for enhancing synthesis of DNA preferably contains DMSO in an amount to achieve a concentration in the DNA synthesis reaction of about 0.1 to 15 wt. %, preferably about 2 to 10 wt. %, and more preferably about 5 to 10 wt. %.

Combination

The second enhancing composition for DNA synthesis of the invention comprises the compound of formula (1) and/or DMSO, in addition to the anionic substance, thus achieving further enhanced DNA synthesis promoting effects. The second composition for enhancing synthesis of DNA is not specifically limited but preferably comprises the above three components, i.e., the anionic substance, the compound of formula (1) and DMSO.

Preferable combinations of the components of the second enhancing composition for DNA synthesis are, for example, a combination of an oxalic acid salt or ester (particularly a salt) and trimethylglycine, a combination of a malonic acid salt or ester (particularly a salt) and trimethylglycine, a combination of a maleic acid salt or ester (particularly a salt) and trimethylglycine, a combination of an oxalic acid salt or ester (particularly a salt) and DMSO, a combination of a malonic acid salt or ester (particularly a salt) and DMSO, a combination of a maleic acid salt or ester (particularly a salt) and DMSO, a combination of an oxalic acid salt or ester (particularly a salt), trimethylglycine and DMSO, a combination of a malonic acid salt or ester (particularly a salt), trimethylglycine and DMSO, a combination of a maleic acid salt or ester (particularly a salt), trimethylglycine and DMSO, and the like. The combination of an oxalic acid salt or ester (particularly a salt) and trimethylglycine is particularly preferable.

For determining the combination of types of components and most suitable concentrations, the type of target DNA, size of the DNA fragment to be amplified, composition of DNA synthesis reaction buffer solution, and the like may need to be considered.

(III) Composition for DNA Synthesis

The DNA synthesizing composition of the invention is a composition comprising an enzyme having DNA polymerase activity and the first composition for enhancing synthesis of DNA or second composition for enhancing synthesis of DNA of the invention described above.

The enzyme having DNA polymerase activity (DNA polymerase) is not particularly limited and examples include DNA-directed DNA polymerases and reverse transcriptases. The DNA polymerase is preferably thermostable. Commercially available enzymes can be used. The reaction solution composition of the invention may contain a plurality of enzyme types having different DNA polymerase activities.

DNA-Directed DNA Polymerase

DNA-directed DNA polymerases are roughly classified into Pol I-type DNA polymerases, α-type DNA polymerases and mixed-type polymerases. It is generally thought that Pol I-type enzymes achieve high DNA elongation rates but have poor fidelity because of the lack of 3'-5' exonuclease activity, whereas α-type enzymes have high fidelity owing to their 3'-5' exonuclease activity but achieve low DNA elongation rates. It is possible to form mixed-type enzymes by mixing a α-type DNA polymerase and a Pol I-type DNA polymerase.

Representative examples of Pol I-type enzymes are Taq DNA polymerase and Tth DNA polymerase. Pol I-type enzymes also include Platinum Taq DNA polymerase series. Examples of α-type enzymes include Tli polymerase, Pfu polymerase, Pfutubo polymerase, Pyrobest polymerase, Pwo polymerase, KOD polymerase, Bst polymerase, Sac polymerase, Sso polymerase, Poc polymerase, Pab polymerase, Mth polymerase, Pho polymerase, ES4 polymerase, VENT polymerase, DEEPVENT polymerase and the like. The mixed-type enzymes include EX-Taq polymerase, LA-Taq polymerase, Expand polymerase series, Hi-Fi polymerase and the like. Unclassified types of enzymes include, for example, Tbr polymerase, Tfl polymerase, Tru polymerase, Tac polymerase, Tne polymerase, Tma polymerase, Tih polymerase, Tfi polymerase and the like. Variants, modified products and derivatives thereof are also usable.

Of these enzymes, Taq, Platinum Taq, Tth, Tli, Pfu, Pfutubo, Pyrobest, Pwo and KOD, VENT, DEEPVENT, EX-Taq, LA-Taq, the Expand series and Platinum Taq Hi-Fi are all commercially available. The other enzymes can be readily isolated from specific bacteria by those of ordinary skill in the art.

The DNA-directed DNA polymerase contained in the DNA synthesizing composition of the invention is preferably a thermostable DNA-directed DNA polymerase which synthesizes DNA at a rate of at least 30 bases/second and has 3'-5' exonuclease activity. The DNA elongation rate can be measured, for example, by the above-mentioned method.

Also preferably, the polymerase is a thermostable DNA-directed DNA polymerase which synthesizes DNA at a rate of at least 30 bases/second and which exhibits an error rate of 4% or less when performing PCR using pMol 21 as a template.

Enzymes that exhibit an error rate of not higher than 1% in PCR using pMol 21 as a template are especially preferable as DNA-directed DNA polymerases. Enzymes that are capable of amplifying at least 20 kb of the template DNA fragment are especially preferable. The method of determining the error rate in PCR using pMol 21 as a template is as mentioned above.

The DNA-directed DNA polymerase can be suitably selected in view of the properties such as "elongation rate", "fidelity", "long-PCR performance" and "heat resistance". A combination of enzymes can also be used.

Since DNA synthesis fidelity depends mainly on the presence or absence of 3'-5' exonuclease activity, enzymes with 3'-5' exonuclease activity (e.g., α-type enzymes) are preferable from the viewpoint of fidelity.

Among them, *Thermococcus kodakaraensis* KOD1-derived KOD polymerase is particularly preferable because it also has excellent properties other than just fidelity. KOD polymerase is a thermostable DNA polymerase that synthesizes DNA at a rate of at least 30 bases/second, has 3'-5' exonuclease activity and exhibits an error rate of not higher than 1% when performing PCR using pMol as a template. KOD polymerase is also capable of amplifying 20 kb or more of target DNA. As KOD polymerase amino acid sequence, the amino acid sequence of SEQ ID NO: 1 is known. KOD polymerases which may be contained in the DNA synthesizing composition of the invention include not only protein consisting of the amino acid sequence of SEQ ID NO: 1 but also modified products thereof substantially maintaining the above properties. More specifically, the DNA polymerases include modified proteins that consist of an amino acid sequence resulting from addition, deletion or substitution of one or more amino acids in the sequence of SEQ ID NO: 1, and substantially possess the above-mentioned properties.

Reverse Transcriptase

The enzyme having DNA polymerase activity may be a reverse transcriptase. Examples of reverse transcriptases include AMV-RT polymerase, M-MLV-RT polymerase, HIV-RT polymerase, EIAV-RT polymerase, RAV2-RT polymerase, *C. hydrogenoformans* DNA polymerase, SuperScript I, SuperScript II, and variants, modified products and derivatives thereof. The RNaseH activity of reverse transcriptase may be substantially suppressed by modification, etc. Enzymes with substantially suppressed Rnase activity include, for example, those in which the Rnase activity is reduced to 90% or less, and preferably those in which the Rnase activity is reduced to 10% or less.

Other Components

The DNA synthesizing composition of the invention may further contain, in addition to the DNA synthesis promotor and enzyme(s) having DNA polymerase activity, at least one member selected from the group consisting of template nucleic acids, one or more types of oligonucleotide primers, one or more types of nucleotides, nucleotide derivatives, buffers, salts, and additives useful for DNA synthesis.

The template nucleic acid may be DNA, RNA, mixtures thereof, etc. Usable oligonucleotide primers include forward primers and backward primers having a nucleotide sequence complementary to a part of the target nucleic acid.

The nucleotides or derivatives thereof are not particularly limited. For example, deoxyphosphonucleotides or derivatives thereof can be used. Specific examples include dATP, dCTP, dGTP, dTTP, dITP, dUTP, α-thio-dNTPs, biotin-dUTP, fluorescein-dUTP and digoxigenin-dUTP.

The salts contained in the reaction solution composition of the invention are not particularly limited. Examples thereof include substances selected from the group consisting of potassium chloride, potassium acetate, potassium sulfate, ammonium sulfate, ammonium chloride, ammonium acetate, magnesium chloride, magnesium acetate, magnesium sulfate, manganese chloride, manganese acetate, manganese sulfate, sodium chloride, sodium acetate, lithium chloride and lithium acetate.

Usually the DNA synthesizing composition contains salts capable of supplying magnesium ions such as magnesium chloride, magnesium acetate or magnesium sulfate. These salts are commercially available. Preferably, magnesium ions are contained in the DNA synthesizing composition in such a concentration that their concentration in the DNA synthesis reaction solution becomes about 0.5 to 10 mM, and more preferably about 1 to 3 mM.

Salts can enhance the solubility of DNA or proteins by increasing the ionic strength of the reaction solution. In addition, salts can also enhance the annealing efficiency of oligonucleotides to nucleic acids.

Buffers are not particularly limited. Examples of usable buffers include TRIS, TRICINE, bis-Tricine, HEPES, MOPS, TES, TAPS, PIPES and CAPS.

Preferably, the buffer is contained in the DNA synthesizing composition in such an amount that its concentration in the DNA synthesis reaction solution becomes about 10 to 200 mM, and more preferably about 20 to 100 mM.

Examples of additives useful for DNA synthesis include formamide, tetramethylammonium chloride, glycerol, PEG, Tween-20, NP40, ectoine, polyols, *Escherichia coli* SSB protein, phage T4 gene 32 protein, BSA and the like. Tetramethylammonium chloride is considered to promote the specificity of primers. BSA is considered to improve the stability of enzymes.

One example of a DNA synthesizing composition of the invention is a composition comprising 20 mM Tris-HCl (pH 6.5 at 75° C.), 10 mM KCl, 6 mM $(NH_4)_2SO_4$, 1 to 3 mM $MgCl_2$, 0.1% Triton X-100, 10 µg/ml BSA, 20 to 200 µM dNTPs, 0.1 pM to 1 µM primer, and 0.1 to 250 ng template DNA.

The DNA synthesizing composition of the invention may contain labeled nucleic acid probes, color reagents, luminescence reagents and the like. These additives may be added after DNA amplification. Such nucleic acid probes, color reagents, luminescence reagents, etc. will be described later.

The DNA synthesizing composition of the invention may further contain antibodies against the DNA polymerase, antibodies for hot start, known enhancers and the like. Antibodies against DNA polymerases are used to suppress the production of byproducts such as primer dimers by completely suppressing the enzyme activity at room temperature. Antibodies for hot start are used for methods (i.e., hot start PCR methods) enhancing the PCR success rate by protecting the primer from digestion.

DNA Polymerase-Related Factor

The DNA synthesizing composition of the invention may contain DNA polymerase-related factors as described later.

(IV) First DNA Synthesis Method

The first DNA synthesis method of the invention comprises the steps of:
(a) mixing a template nucleic acid, the above DNA synthesizing composition of the invention (DNA synthesizing composition comprising the composition for enhancing synthesis of DNA of the invention and an enzyme having DNA polymerase activity), nucleotides or nucleotide derivatives and primers to form a mixture; and
(b) incubating the mixture under such conditions that DNA is synthesized at a rate of at least 30 bases/second and, when performing PCR using pMol 21 as a template, the error rate is 4% or less to prepare a first nucleic acid molecule complementary to the entire or part of the template nucleic acid.

The present invention includes nucleic acid molecules prepared by the above method.

In the first DNA synthesis method of the invention, when DNA is used as a template nucleic acid as in standard PCR, the target DNA molecule is obtained as the first nucleic acid molecule. When RNA is used as a template nucleic acid as in RT-PCR, cDNA is obtained as the first nucleic acid molecule. When RNA is used as a template nucleic acid, the target DNA molecule can be synthesized as a second nucleic acid molecule after obtaining cDNA as the first nucleic acid molecule, by the method described later.

In step (b) of the above method, it is preferable to use conditions such that the error rate during PCR using pMol 21 as a template is 1% or less. In addition, it is preferable to use conditions such that target 20 kb or more DNA in template nucleic acid can be amplified.

In step (a), the mixture may further contain buffers, salts and other additives useful for DNA synthesis.

In the first DNA synthesis method of the invention, purified or unpurified template nucleic acids may be used but a purified one is preferable. In particular, when the supply source of nucleic acid is cells from tissues; cells from body fluids such as blood, lymph, milk, urine, sperm and the like; feces; cultured cells; cells in agarose or polyacrylamide, it is preferable to purify the nucleic acid because contaminants that interfere with the treatment or analysis in the nucleic acid synthesis or amplification step and/or subsequent steps are likely to be present in substantial amounts.

Examples of such contaminants include substances that interfere with or suppress chemical reactions (such as nucleic acid or protein hybridization, enzymatic catalytic reactions, etc.); substances that catalyze the degradation, digestion or polymerization of the target nucleic acid or other biological substances; and substances that give a false positive background in target substance-quantification samples in cases where no nucleic acid is actually present in the sample.

Specific examples of contaminants include high polymers, or high molecular materials from in vivo or in vitro media from which the target nucleic acid is isolated, enzymes and like high molecular weight materials, other types of proteins, polysaccharides, polynucleotides, lipids and like low molecular weight materials, low molecular weight enzyme inhibitors, oligonucleotides and the like. Contaminants may be introduced into the target biological substance from chemicals or substances used to isolate the target nucleic acid. Trace of metals, dyes and organic solvents are examples of such contaminants.

From another viewpoint, when 10 kb or more, and preferably 20 kb or more of the target DNA is intended to be synthesized by long PCR, it is preferable to purify the template nucleic acid to reduce the possibility of reaction stoppage due to the effects of contaminants. Because RNA needs to be isolated in RT-PCR, a purified template nucleic acid is preferably used. In standard PCR or similar reactions other than those mentioned above, it is also preferable to purify the template nucleic acid to prevent the presence of substantial levels of contaminants that interfere with polymerase reactions.

The purification method is not particularly limited. However, the template nucleic acid is preferably purified by a method comprising the following steps (i) to (iii) because of its convenience, high safety, economy, high yields, relatively mild treatment conditions, etc., as compared with known nucleic acid purification methods such as phenol/chloroform extraction/ethanol precipitation methods.

Step (i): mixing a nucleic acid-binding magnetic carrier consisting of ferromagnetic metal oxide-containing magnetic silica particles, a nucleic acid-containing material and a nucleic acid extraction solution;

Step (ii): separating the nucleic acid-bound magnetic carrier from the residual mixture using a magnetic field; and Step (iii): eluting the nucleic acid from the magnetic carrier.

The DNA synthesis method of the invention may further contain the step (c) of incubating a mixture containing the first nucleic acid molecule under such conditions that DNA is synthesized at a rate of at least 30 bases/second, and when performing PCR using pMol 21 as a template, the error rate is 4% or less to prepare a second nucleic acid molecule complementary to the entire or part of the first nucleic acid molecule.

When DNA is used as the template nucleic acid, step (c) is a process of synthesizing DNA as a second nucleic acid molecule by using the DNA obtained as a first nucleic acid molecule in steps (a) and (b) as a template. When RNA is used as the template nucleic acid, step (c) is a process of synthesizing DNA as a second nucleic acid molecule by using cDNA obtained as a first nucleic acid molecule in steps (a) and (b) as a template.

In step (c), it is also preferable to use conditions such that the error rate during PCR using pMol 21 as a template is 1% or less. In addition, it is preferable to use conditions such that 20 kb or more of first nucleic acid target DNA can be amplified.

The DNA synthesis method of the invention may further contain the step (d) of purifying the obtained first nucleic acid molecule. The purification step (d) may comprise, for example, the following steps (iv) to (vi):

(iv) mixing a nucleic acid-binding magnetic carrier consisting of ferromagnetic metal oxide-containing magnetic silica particles, a material comprising the synthesized DNA, and a nucleic acid extraction solution;

(v) separating the DNA-bound magnetic carrier from the residual liquid using a magnetic field; and (vi) eluting the nucleic acid from the magnetic carrier.

Since the above purification method is carried out using mild treatment conditions, it is rare that nucleic acid is mechanically sheared, thus being preferable, particularly when the template nucleic acid is subjected to long-PCR. After performing DNA synthesis, it is sometimes necessary to isolate the target substance from the other components in the solution. In this case also, the use of nucleic acid isolation or purification methods similar to the above is effective.

In the first DNA synthesis method of the invention, hot start PCR methods can be used.

Hot start PCR is used to avoid the occurrence of problems such as non-specific formation of double-stranded hybrid from a primer and a template DNA, formation of double-stranded hybrids from primers to cause an extra band or primer dimer to form, and reduction of the specificity of primers by digestion of the primers with enzymes having 3'-5' exonuclease activity when such enzymes are used; and these problems occurring upon raising the temperature in the initial denaturation heating step to convert double stranded DNA into a single-stranded DNA prior to the temperature cycling in the PCR process.

The hot start PCR method is not particularly limited. Methods comprising adding an enzyme after the temperature rise and methods using wax to separate the enzyme from the reaction solution are convenient. However, the former has cross-contamination and operative problems due to the opening and closing of the tubes, whereas the latter has a problem in that immediately after melting of the wax, the enzyme does not uniformly exist in the reaction medium. Another method comprises hydrolysing the enzyme using a reagent but it takes a long time, i.e., about 10 to 20 minutes to inactivate the reagent.

Currently, a method comprising blocking the enzymatic activity using an antibody against DNA polymerase is preferably used a convenient and reproducible method. According to this method, the antibody binds to the enzyme in a preprepared reaction solution to inactivate the enzyme, and when the temperature exceeds a certain level during heating in the initial denaturation step, the antibody is denatured so that the enzyme is activated and PCR starts.

In the case of using RNA as a template nucleic acid, i.e., RT-PCR, in order to allow hot start PCR to proceed in the step of synthesizing DNA as a second nucleic acid molecule using cDNA obtained as a first nucleic acid in steps (a) and (b) as a template, whether the antibody is added at the beginning of the reverse-transcription reaction or after cDNA synthesis can be suitably decided in consideration of the reverse-transcription reaction temperature and whether all the steps are sequentially performed as a single continuous step or divided into two steps, i.e., a cDNA synthesis step and the subsequent steps.

(V) DNA Amplification Method

The DNA amplification method of the invention comprises the steps of:

(a) mixing a template nucleic acid with the DNA synthesizing composition of the invention (DNA synthesizing composition comprising the composition for enhancing synthesis of DNA of the invention and an enzyme having DNA polymerase activity), nucleotides or nucleotide derivatives and primers to form a mixture; and (b) incubating the mixture under such conditions that DNA is synthesized at a rate of at least 30 bases/second and, when performing PCR using pMol 21 as a template, the error rate is 4% or less, to amplify a nucleic acid molecule complementary to the entire or part of the template nucleic acid.

In step (b), it is preferable to use conditions such that the error rate in PCR using pMol 21 as a template is 1% or less. In addition, it is preferable to use conditions such that target 20 kb or more DNA in template nucleic acid can be amplified.

In the above DNA synthesis method, a purified nucleic acid is preferably used as a template. The purification method of the template nucleic acid is as described above in the DNA synthesis method of the invention.

The DNA amplification method of the invention may further comprise the step of (c) incubating a mixture containing the first nucleic acid molecule under such conditions that DNA is synthesized at a rate of at least 30 bases/second, and when performing PCR using pMol 21 as a template the error rate is 4% or less to prepare a second nucleic acid molecule complementary to the entire or part of the first nucleic acid.

The DNA amplification method of the invention may further comprise the step of (d) purifying the amplified nucleic acid molecule. The purification step is also as described above in the DNA synthesis method of the invention.

Hot start PCR can also be used in the DNA amplification method of the invention.

PCR

Examples of the enzymatic reaction for DNA synthesis used in the DNA amplification method of the invention include DNA-directed DNA polymerase reactions and reverse transcriptase reactions. Among these, DNA-directed DNA polymerase reactions, in particular gene amplification methods using PCR are especially effective.

Gene amplification methods using PCR are methods which comprise repeating a 3-step cycle consisting of denaturation, annealing and elongation in the presence of a template nucleic acid, the 4 types of deoxyribonucleoside triphosphates, a pair of primers and a DNA polymerase to exponentially amplify the target DNA region flanked by the pair of primers (*Nature*, 324 (6093), 13-19 (1986)). More specifically, a nucleic acid sample is denatured in the denaturation step; in the subsequent annealing step, each primer is hybridized to its complementary region on the single-stranded template nucleic acid; and in the subsequent elongation step, new DNA chains complementary to the single-stranded target nucleic acid region are elongated from each primer by the action of DNA polymerase to form double-stranded DNA. One double-stranded DNA fragment is amplified to two double-stranded DNA fragments per cycle. Therefore, if this cycle is repeated n times, the sample DNA region between the pair of primers is theoretically amplified $2^n$ times.

The reaction conditions preferable for amplification are such that thermocycling conditions, i.e., the temperature of the reaction mixture is changed to perform each step of the PCR cycle. Thermocycling is usually performed at a temperature in the range of about 23° C. to about 100° C., and preferably about 37° C. to about 95° C. Nucleic acid denaturation is usually performed at a temperature in the range from about 90° C. to about 100° C., and preferably about 94° C. Annealing is usually performed at a temperature in the range from about 37° C. to about 75° C., and preferably about 60° C. DNA elongation is usually performed at a temperature in the range from about 55° C. to about 80° C., and preferably about 68° C. to about 72° C.

The number of cycles varies greatly depending on desired amount of the DNA product. The number of PCR cycles is preferably in the range from about 5 to about 99 cycles, especially preferably about 20 cycles or more, and particularly preferably about 25 to about 40 cycles.

Detection of Amplified Product

In the invention, the target nucleic acid can be detected by, for example, using a labeled probe to detect the amplified product obtained by the above amplification reaction. The labeled probe is an oligonucleotide which has a nucleotide sequence complementary to the labeled nucleic acid and to which is attached a marker or marker-bound substance.

Examples of usable markers include alkaline phosphatase, peroxidase, galactosidase and like enzymes, fluorescent or radioactive substances and the like. Examples of usable marker-binding substances include biotin, digoxigenin and the like. Markers may be bound via biotin, digoxigenin, avidin, etc. One example of a method of introducing these markers into probes is synthesis of oligonucleotide using, as one component of dNTP, dNTP to which are attached such markers or marker-bound substances. When enzymes are used as marker substances, color reagents, i.e., substrates that exhibit color upon digestion with enzymes (e.g., tetramethylbenzidine (TMB) or ortho-phenylenediamine (OPD)), or luminescent reagents, i.e., substrates emitting light (e.g., CDP-Star, PPD)) are usable.

The detection of labeled probe-bound nucleic acids can be performed by known methods, such as Southern hybridization or Northern hybridization methods. These methods utilize hybrid formation when single-stranded DNAs or RNAs are complementary to each other. These methods comprise the steps of: separating unknown nucleic acid fragments according to size by, for example, agarose electrophoresis; converting the nucleic acid fragments in the gel to single strands by, for example, alkali treatment; transferring the single strands to a filter to be immobilized; and hybridizing the immobilized single-stranded nucleic acid to the labeled probe.

In the case of using, for example, alkaline phosphatase as a marker, when a chemiluminescent substrate, e.g., a 1,2-dioxycetane compound (PPD) is reacted with nucleic acids in contact with a labeled probe in a filter to detect the marker, only the hybridized nucleic acids emit light. By exposing X-ray films to this light, the size and electrophoresis position of the target nucleic acid can be confirmed.

(VI) Nucleotide Sequencing Method for Nucleic Acid Molecules

The nucleotide sequencing method of the invention for nucleic acid molecules comprises the steps of:
(a) mixing a template nucleic acid, the DNA synthesizing composition of the invention. (DNA synthesizing composition comprising the composition for enhancing synthesis of DNA of the invention and an enzyme having DNA polymerase activity), nucleotides or nucleotide derivatives, primers and a release factor, to form a mixture;
(b) incubating the mixture under such conditions that DNA is synthesized at a rate of at least 30 bases/second and the error rate in PCR when using pMol 21 as a template is 4% or less, to amplify a nucleic acid molecule complementary to the entire or part of the target nucleic acid to be sequenced; and
(e) separating the amplified nucleic acid molecule to determine the entire or partial nucleotide sequence.

In step (b) of the above method, it is preferable to use conditions such that the error rate in PCR when using pMol 21 as a template is 1% or less. In addition, it is preferable to use conditions such that 20 kb or more of target DNA in the template nucleic acid is amplified.

In the above sequencing method, the nucleic acid to be sequenced is preferably a purified one. The nucleic acid purification method is as described above in the DNA synthesis method of the invention.

The DNA amplification method of the invention may further comprise, between steps (b) and (e), (or between steps (b) and (d) when the method further comprises step (d)), the step of (c) incubating a mixture containing a first nucleic acid molecule under such conditions that DNA is synthesized at a rate of at least 30 bases/second and the error rate in PCR when using pMol 21 as a template is 4% or less, to prepare a second nucleic acid molecule complementary to the entire or part of the first nucleic acid molecule.

The DNA amplification method of the invention may further comprise, between steps (b) and (e) (or between steps (c) and (e) when the method further comprises step (c)), the step of (d) purifying the amplified nucleic acid molecule. The purification method is also as described above in the DNA synthesis method of the invention.

In the sequencing method of the invention, the DNA synthesizing composition of the invention may be added according to a hot start PCR method.

The Maxam-Gilbert method (Maxam, A. M. and Gilbert, W., Proc. Natl. Acad. Sci. USA 74: 560-564, 1997) and the Sanger method (Sanger, F. and Coulson, A. R., J. Mol. Biol. 94: 444-448, 1975) are widely known nucleotide sequencing methods for nucleic acids.

In the Maxam-Gilbert method, the target DNA is radio-labeled and divided into 4 samples. Specific nucleotide bases in DNA are selectively destroyed and the samples are treated with chemical reagents that cleave the molecule at the lesion site. The obtained fragments are separated into different bands by gel electrophoresis and an x-ray film is exposed to the gel so that the sequence of the original DNA molecule can be read off the film.

In contrast, the Sanger method utilizes the DNA synthesis activity of a DNA polymerase. In this method, the nucleic acid to be sequenced and DNA polymerase are mixed with a mixture of a reaction terminator dideoxynucleotide triphosphate (Sanger, F. et al., Proc. Natl. Acad. Sci. USA 74: 5463-5467, 1977) and a short primer (either of which can be labeled in a detectable manner) to synthesize a series of new DNA fragments that are specifically terminated at one of the four dideoxy bases. Subsequently, these fragments are analyzed by gel electrophoresis to determine their sequences. By performing four different reactions (one for each ddNTP), considerably complicated DNA molecule sequences can be quickly determined (Sanger, F. et al., Nature 265: 678-695, 1977; Barnes, W., Meth. Enzymol. 152: 538-556, 1987).

(VII) DNA Molecule Synthesis Kit

The DNA molecule synthesis kit of the invention comprises one or more kinds of constituent compounds or components of the DNA synthesizing composition of the invention.

The kit may be composed of two or more separate parts or all the constituent components may be entirely contained in one part. When the kit is composed of two or more parts, the constituent compounds or components may be separately contained in any of the parts.

The kit of the invention may contain, in addition to a DNA polymerase, various components that can be contained in the above reaction composition.

(VIII) DNA Polymerase-Related Factor

The first DNA polymerase-related factor of the invention is a *Thermococcus* species-derived thermostable DNA polymerase-related factor capable of promoting the DNA synthesis activity of DNA polymerase.

The second DNA polymerase-related factor of the invention is a *Thermococcus* species-derived thermostable DNA polymerase-related factor capable of binding to DNA polymerase.

Definition

In the specification, "DNA polymerase-related factor" refers to a factor that affects the functions of DNA polymerase when used with a DNA polymerase. Specific examples include factors capable of promoting the DNA synthesis activity of DNA polymerase, factors capable of binding to polymerase, and factors having both functions or activities.

The method for determining the activity of promoting the DNA synthesis activity of DNA polymerase is not particularly limited and may be any method typically used for determining the DNA synthesis activity of DNA polymerase. More specifically, "promotion of the DNA synthesis activity of DNA polymerase" means an action of enhancing any of processability, DNA elongation rate and dNTP incorporation activity (preferably an increase of 50% or more, particularly 100% or more)

Processability

Processability refers to the number of nucleotides synthesized during the period from the binding of DNA polymerase to the substrate DNA to its release.

One example of a processability determination method is shown below. A reaction solution containing DNA polymerase (120 mM Tris-HCl buffer solution (pH 8.0), 1 mM magnesium chloride, 10 mM KCl, 6 mM $(NH_4)_2SO_4$, 0.1% TritonX-100, 10 µg/ml BSA, 0.2 mM dNTP) is reacted with substrate DNA consisting of single-stranded M13mp18 DNA to which has been annealed primers labeled with $^{32}P$ at the 5'-end at 75° C. under such conditions that the substrate is present in a several-fold molar excess relative to the DNA polymerase. By using such conditions under which the turnover of DNA polymerase is unlikely to happen, the number of nucleotides synthesized without release of DNA polymerase from the substrate DNA can be determined. After a certain reaction time, the reaction is terminated by adding a reaction terminating solution (50 mM sodium hydroxide, 10 mM EDTA, 5% Ficoll, 0.05% Bromophenol Blue) in a volume equal to the reaction mixture.

The DNAs synthesized by the above reaction are fractionated by electrophoresis on an alkaline agarose gel, and the gel is dried and subjected to autoradiography. Labeled λ/HindIII is used as a DNA size marker. Processability is determined by measuring the number of synthesized nucleotides with reference to the marker band.

DNA Elongation Rate

"DNA elongation rate" refers to the number of DNA molecules synthesized per unit time. The DNA elongation rate can be determined in the following manner. A reaction solution containing DNA polymerase (120 mM Tris-HCl buffer solution (pH 8.0), 1 mM magnesium chloride, 10 mM KCl, 6 mM $(NH_4)_2SO_4$, 0.1% TritonX-100, 10 µg/ml BSA, 0.2 mM dNTP, 0.2 µCi [$\alpha$-$^{32}$P]dCTP) is reacted at 75° C. with single-stranded M13 mp18 DNA to which primers has been annealed. After a certain reaction time, the reaction is terminated by adding an equal volume of a reaction terminating solution (50 mM sodium hydroxide, 10 mM EDTA, 5% Ficoll, 0.05% Bromophenol Blue).

The DNA synthesized by the above reaction is fractionated by electrophoresis on an alkaline agarose gel, and the gel is dried and subjected to autoradiography. Labeled λ/HindIII is used as a DNA size marker. The DNA elongation rate is determined by measuring the synthesized DNA size using the marker band as an index.

dNTP Incorporation Activity

"dNTP incorporation activity" refers to a catalytic activity to introduce deoxyribonucleotide-5'-monophosphate, according to a template, into deoxyribonucleic acid by covalently binding α-phosphate of deoxyribonucleotide-5'-triphosphate to the 3'-hydroxyl group of an oligonucleotide or polynucleotide annealed to the template DNA.

If the enzymatic activity of a sample is high, activity measurement shall be carried out after the sample is diluted with a stock buffer (for example, 50 mM Tris-HCl (pH8.0), 50 mM KCl, 1 mM dithiothreitol, 0.1% Tween 20, 0.1% Nonidet P40, 50% glycerin).

According to the invention, 25 μl of Solution A, 5 μl of Solution B and 5 μl of Solution C shown below, 10 μl of sterilized water and 5 μl of an enzyme solution are pipetted into a microtube and reacted at 75° C. for 10 minutes. The reaction solution is then ice-cooled, and 50 μl of Solution E and 100 μl of Solution D are added and stirred, followed by ice-cooling for 10 minutes. The solution is filtered through a glass filter (Wattman GF/C Filter), and the filter is well washed with Solution D and ethanol, and the radioactivity of the filter is counted in a liquid scintillation counter (Packard) to determine the incorporation of the nucleotide into the template DNA. 1 unit of enzyme activity is defined as the amount of enzyme that catalyzes the incorporation of 10 nmol of nucleotides into an acid-insoluble fraction (i.e., DNA fraction which becomes insoluble when Solution D is added) per 30 minutes under the above conditions.

Solution A: 40 mM Tris-HCl buffer (pH 7.5)
16 mM magnesium chloride
15 mM dithiothreitol
100 μg/ml BSA Solution B: 2 μg/μl activated calf thymus DNA Solution C: 1.5 mM dNTP (250 cpm/pmol [$^3$H]dTTP)

Solution D: 20% trichloroacetic acid (2 mM sodium pyrophosphate)

Solution E: 1 mg/ml salmon sperm DNA

Properties

The DNA polymerase-related factor of the invention is a thermostable protein. Therefore, the factor can be used in DNA synthesis reactions performed under conditions of high temperature using a thermostable DNA polymerase.

In this specification, "thermostable" means retaining a capability to promote DNA synthesis activity even after heat treatment. More specifically, it means that when 2 nM or more of the DNA polymerase-related factor of the invention is contained with 6 nM of a DNA polymerase in a 20 mM Tris-HCL (pH 7.5 at 75° C.) buffer solution, at least 50%, preferably 75% or more, and particularly preferably 90% or more of its capability to promote DNA synthesis activity is retained after heat treatment at 80° C. for 15 minutes, as compared to the untreated case.

DNA Polymerase-Related Factor Promoting the DNA Synthesis Activity of DNA Polymerase (First DNA Polymerase-Related Factor of the Invention)

Examples of DNA polymerase-related factors promoting the DNA synthesis activity of DNA polymerase include thermostable DNA polymerase-related factors derived from *Thermococcus* species. In particular, DNA polymerases from the hyperthermophilic archaeon *Thermococcus kodakaraensis* (KOD DNA polymerase) are preferable and DNA polymerase-related factors from the *Thermococcus kodakaraensis* KOD1 are particularly preferable.

Such DNA polymerases whose activities are promoted by the DNA polymerase-related factor of the invention are not particularly limited and examples include DNA polymerases such as pol I derived from *E. coli*, and thermostable DNA polymerases such as Tth DNA polymerase derived from *Thermus thermophilus*, Taq DNA polymerase derived from *Thermus aquaticus*, Pfu DNA polymerase derived from *Pyrococcus furiosus*, and DNA polymerase derived from *Thermococcus kodakaraensis* (KOD DNA polymerase). Thermostable DNA polymerases, in particular, DNA polymerases derived from hyperthermophilic archaeon are preferable. Specific examples include DNA polymerases from the hyperthermophilic archaeon *Thermococcus* kodakaraensis (KOD DNA polymerase).

One example of a KOD DNA polymerase is an enzyme comprising a DNA polymerase-constituent protein having the amino acid sequence of SEQ ID NO: 1.

The DNA polymerase-related factor of the invention may be capable of promoting the activity of merely a specific DNA polymerase but preferably is capable of promoting the activities of several kinds of DNA polymerases derived from various sources.

Furthermore, the combined use of two or more DNA polymerase-related factors of the invention enables coexisting DNA polymerases to exhibit further enhanced DNA polymerase activity as compared with a single use.

DNA Polymerase-Related Factor Capable of Binding to DNA Polymerase (Second DNA Polymerase-Related Factor of the Invention)

Examples of DNA polymerase-related factors capable of binding to DNA polymerase include thermostable DNA polymerase-related factors derived from *Thermococcus* species. In particular, DNA polymerases derived from the hyperthermophilic archaeon *Thermococcus kodakaraensis* (KOD DNA polymerase) are preferable and DNA polymerase-related factors from the *Thermococcus kodakaraensis* KOD1 are particularly preferable.

In this specification, the DNA polymerase-related factors capable of binding to DNA polymerase includes not only those that can directly bind to DNA polymerase but also those that can bind to DNA polymerase indirectly via other substances such as other DNA polymerase-related factors.

The DNA polymerase to which the DNA polymerase-related factor of the invention is bound is not particularly limited and examples include DNA polymerases such as pol I derived from *E. coli*, and thermostable DNA polymerases such as Tth DNA polymerase derived from *Thermus thermophilus*, Taq DNA polymerase derived from *Thermus aquaticus*, Pfu DNA polymerase derived from *Pyrococcus furiosus*, and DNA polymerase derived from *Thermococcus kodakaraensis* (KOD DNA polymerase). Thermostable DNA polymerases, in particular, DNA polymerases derived from hyperthermophilic archaea are preferable. Specific examples include DNA polymerases from the hyperthermophilic archaeon *Thermococcus* kodakaraensis (KOD DNA polymerase).

The DNA polymerase-related factor of the invention may be capable of binding to a specific DNA polymerase or capable of binding to several kinds of DNA polymerases derived from various sources. The latter is preferable.

Methods usable for measuring the binding of the DNA polymerase-related factor to DNA polymerase include, for example, a method comprising mixing the DNA polymerase-related factor and DNA polymerase, followed by nondenatured gel electrophoresis and gel filtration to ascertain the change in molecular weight, a method of determining the adsorption of the DNA polymerase-related factor to a DNA polymerase-immobilized carrier, etc.

Amino Acid Sequence and DNA Sequence

Examples of DNA polymerase-related factors of the invention include those comprising any one of the proteins (e) to (j) below:

(e) a protein comprising the amino acid sequence of SEQ ID NO: 2;
(f) a protein which comprises an amino acid sequence resulting from addition, deletion or substitution of one or more amino acids in the sequence of SEQ ID NO: 2, and which can promote the DNA synthesis activity of a DNA polymerase or bind to a DNA polymerase;
(g) a protein comprising the amino acid sequence of SEQ ID NO: 4;
(h) a protein which comprises an amino acid sequence resulting from addition, deletion or substitution of one or more amino acids in the sequence of SEQ ID NO: 4, and which can promote the DNA synthesis activity of a DNA polymerase or bind to a DNA polymerase;
(i) a protein comprising the amino acid sequence of SEQ ID NO: 6;
(j) a protein which comprises an amino acid sequence resulting from addition, deletion or substitution of one or more amino acids in the sequence of SEQ ID NO: 6, and which can promote the DNA synthesis activity of a DNA polymerase or bind to a DNA polymerase.

Proteins (f), (h) and (j) are functional equivalents to proteins (e), (g), and (i) respectively. The term "functional equivalents" refers to those which are substantially equivalent in their functions and activities even though they are structurally different. The functional equivalents are included in the scope of the DNA polymerase-related factors of the invention.

Proteins comprising a part of the amino acid sequence of SEQ ID NO: 2, 4 or 6 are also included in the scope of the DNA polymerase-related factors of the invention.

The term "proteins comprising" as used herein refers to the proteins described below, which are also included in the present invention. That is, when a protein is produced by genetic engineering techniques, it is often expressed as a fusion protein. For instance, in order to increase the target protein expression level, an N-terminal peptide chain derived from other proteins may be added to the N-terminus; or, with the purpose of facilitating the purification of the target protein, the protein may be expressed by adding an appropriate peptide chain at the N-terminus or C-terminus of the target protein, and a carrier having affinity with the peptide chain may be used. Such fusion proteins are also included in the DNA polymerase-related factors of the invention.

Among the proteins (e), the protein consisting of the amino acid sequence of SEQ ID NO: 2 is preferable. Among the proteins (f), preferable are those consisting of an amino acid sequence resulting from addition, deletion or substitution of one or more amino acids in the sequence of SEQ ID NO: 2, and are capable of promoting the DNA synthesis activity of a DNA polymerase or binding to a DNA polymerase. Among the proteins (g), the protein consisting of the amino acid sequence of SEQ ID NO: 4 is preferable. Among the proteins (h), preferable are those consisting of an amino acid sequence resulting from addition, deletion or substitution of one or more amino acids in the sequence of SEQ ID NO: 4, and are capable of promoting the DNA synthesis activity of a DNA polymerase or binding to a DNA polymerase. Among the proteins (i), the protein consisting of the amino acid sequence of SEQ ID NO: 6 is preferable. Among the proteins (j), preferable are those consisting of an amino acid sequence resulting from addition, deletion or substitution of one or more amino acids in the sequence of SEQ ID NO: 6, and are capable of promoting the DNA synthesis activity of a DNA polymerase or binding to a DNA polymerase.

Proteins consisting of the amino acid sequence of SEQ ID NO: 2 is KOD-PCNA (proliferating cell nuclear antigen) derived from the *Thermococcus kodakaraensis* KOD1. Proteins consisting of the amino acid sequence of SEQ ID NO: 4 is KOD-RFCS (replication factor C small subunit) derived from the *Thermococcus kodakaraensis* KOD1. Proteins consisting of the amino acid sequence of SEQ ID NO: 6 is KOD-RFCL (replication factor C large subunit) derived from the *Thermococcus kodakaraensis* KOD1.

Genes Encoding the DNA Polymerase-Related Factors of the Invention

The genes encoding the DNA polymerase-related factors of the invention are those encoding the above proteins (e) to (j). Examples of such genes include the following genes (k) to (p):

(k) a gene comprising the nucleotide sequence of SEQ ID NO: 3;
(l) a gene which hybridizes with the gene comprising the nucleotide sequence of SEQ ID NO: 3 under stringent conditions, and which can promote the DNA synthesis activity of a DNA polymerase or bind to a DNA polymerase;
(m) a gene comprising the nucleotide sequence of SEQ ID NO: 5;
(n) a gene which hybridizes with the gene comprising the nucleotide sequence of SEQ ID NO: 5 under stringent conditions, and which can promote the DNA synthesis activity of a DNA polymerase or bind to a DNA polymerase;
(o) a gene comprising the nucleotide sequence of SEQ ID NO: 7;
(p) a gene which hybridizes with the gene comprising the nucleotide sequence of SEQ ID NO: 7 under stringent conditions, and which can promote the DNA synthesis activity of a DNA polymerase or bind to a DNA polymerase.

The term "gene" used herein includes DNA and RNA. DNAs or RNAs having a sequence complementary to the nucleotide sequences described herein are also included in the scope of the gene of the invention. Furthermore, double-stranded nucleic acids are also included in the scope of the gene of the invention.

A "gene that hybridizes to a specific gene" used herein has a nucleotide sequence similar to that of the specific gene. There is a high possibility that the amino acid sequence and functions of the protein encoded by such a gene are also similar to those of the protein encoded by the specific gene.

The homology of the nucleotide sequence of the genes can be determined by checking whether or not the DNAs or RNAs of the two genes or partial strands thereof can hybridize to each other under stringent conditions. By using this method, genes that encode proteins having functions similar to those of the protein encoded by a specific gene can be obtained.

Herein, "stringent conditions" refers to conditions in which nonspecific hybridization does not occur. More specifically, for example, the following conditions can be mentioned. A DNA-immobilized membrane is reacted with a labeled DNA probe at 50 for 12 to 20 hours in 6×SSC (1×SSC: 0.15 M NaCl, 0.015 M sodium citrate, pH 7.0) containing 0.5% SDS, 0.1% bovine serum albumin (BSA), 0.1% polyvinyl pyrrolidone, 0.1% Ficol 400, and 0.01% denatured salmon sperm DNA. After completion of the reaction, the membrane is washed at a temperature of 3° C. to 50° C. in 2× to 0.1×SSC containing 0.5% SDS, until the immobilized labeled DNA probe signal can be distinguished from the background. Such conditions are referred to as stringent conditions herein and any gene that hybridizes with a gene comprising the nucleotide sequence of SEQ ID NO: 3, 5 or 7 under such conditions and is capable of promoting the DNA synthesis polymerase activity of DNA polymerase or binding to DNA polymerase is included in the scope of the invention.

Among the genes (k), the gene consisting of the nucleotide sequence of SEQ ID NO: 3 is preferable. Among the genes (l), preferable are those that hybridize with the gene consisting of the nucleotide sequence of SEQ ID NO: 3 under stringent conditions and that are capable of promoting the DNA synthesis activity of a DNA polymerase or binding to a DNA polymerase. Among the genes (m), the gene consisting of the nucleotide sequence of SEQ ID NO: 5 is preferable. Among the genes (n), preferable are those that hybridize with the gene consisting of the nucleotide sequence of SEQ ID NO: 5 under stringent conditions and that are capable of promoting the DNA synthesis activity of a DNA polymerase or binding to a DNA polymerase. Among the genes (o), the gene consisting of the nucleotide sequence of SEQ ID NO: 7 is preferable. Among the genes (p), preferable are those that hybridize with the gene consisting of the nucleotide sequence of SEQ ID NO: 7 under stringent conditions and that are capable of promoting the DNA synthesis activity of a DNA polymerase or binding to a DNA polymerase.

Cloning of the Gene Encoding the DNA Polymerase-Related Factor of the Invention

The gene encoding the DNA polymerase-related factor of the invention can be obtained, for example, by the following method:

It has been reported that PCNA (proliferating cell nuclear antigen; hereinafter referred to as "PCNA") forms a complex with RFC (replication factor C; hereinafter referred to as "RFC") and plays a role in DNA replication [Seikagaku (Biochemistry), volume 8, (1996), 1542-1548]. Therefore, it was expected that in *Thermococcus kodakaraensis* also, proteins corresponding to PCNA and RFC are expressed and play a role in DNA synthesis reactions. The genes encoding PCNA and RFC homologues of *Thermococcus kodakaraensis* were obtained by the steps described below.

The entire nucleotide sequences of chromosomal DNAs of the archaea *Methanococcus jannaschii* and *Pyrococcus horikoshii* have been already elucidated, and the nucleotide sequences were presumed to contain genes that encode proteins deduced to be homologues of PCNA and the RFC small and large subunits. Genes encoding the homologues of PCNA, RFC small subunit (hereinafter also referred to as "RFCS") and large subunit (hereinafter also referred to as "RFCL") of these species and the corresponding known genes were compared to each other to search for highly homologous nucleotide sequences. By reference to the search results, pairs of primers used to obtain gene fragments encoding PCNA, RFC small subunit (RFCS) and large subunit (RFCL) were designed.

By using each pair of primers to obtain PCNA, RFC small subunit (RFCS) and large subunit (RFCL), PCR was performed on template chromosomal DNA of the hyperthermophilic archaeon *Thermococcus kodakaraensis* KOD1 with a KOD-derived DNA polymerase, "KOD-Plus" (product of Toyobo Co., Ltd.) to amplify DNA fragments. The DNA sequences of the amplified fragments were determined and the acquisition of the target genes (KOD-PCNA, KOD-RFCL and KOD-RFCS genes) was confirmed by homology comparison with known genes.

Subsequently, using these fragments as probes, a phage DNA library containing the chromosomal DNA of KOD1 prepared by a partial restriction enzyme digestion was subjected to plaque hybridization to give phage clones PCNA/λ, RFCS/λ and RFCL/λ.

It was found that the cloned KOD-PCNA gene (SEQ ID NO: 3) consists of 750 bases, encoding 249 amino acids; the KOD-RFCL gene (SEQ ID NO: 5) consists of 1500 bases, encoding 499 amino acids; and the KOD-RFCS gene (SEQ ID NO: 7) consists of 2601 bases, encoding 866 amino acids.

It was found that the KOD-RFCS gene is cleaved in the RFCS-conserved region III and an intervening sequence (intein) consisting of 1620 bases (539 amino acids) is present in this portion. Therefore, the intervening sequence was deleted by the PCR fusion method, thus giving a mature KOD-RFCS gene comprising 981 bases (326 amino acids).

(IX) Process for Preparing a DNA Polymerase-Related Factor

The process for preparing a DNA polymerase-related factor of the invention comprises the step of culturing a transformant harboring the gene of the invention and the step of recovering from the culture a thermostable DNA polymerase-related factor which can promote the DNA synthesis activity of a DNA polymerase, or bind to DNA polymerase, or have both functions or activities.

In the culture recovery step, the DNA polymerase may be simply recovered or can be further subjected to purification. Any generally employed method for protein purification can be used as the purification method.

For example, a DNA encoding the DNA polymerase-related factor of the invention (more specifically, for example, a KOD-PCNA, KOD-RFCL or KOD-RFCS gene obtained by the above method) is ligated to an expression vector, so that the gene can be overexpressed under the control by an expression vector promoter. In addition, the DNA polymerase-related factor of the invention can be easily recovered from a transformant harboring the gene of the invention by ligating a DNA encoding the DNA polymerase-related factor of the invention to a DNA encoding a histidine tag so as to be expressed as a fusion protein. This is because the fusion protein can be easily isolated by using a usually used nickel column.

(X) DNA Synthesis Method Using the DNA Polymerase-Associated Factor of the Invention The second DNA synthesis method of the invention is a method of synthesizing DNA using a DNA polymerase in the presence of the DNA polymerase-related factor of the present invention (comprising one or more of the proteins (e) to (j)). When a polymerase chain reaction (PCR) is performed by the second DNA synthesis method of the invention, PCR sensitivity can be increased by at least several-fold to several tens-fold by synthesizing DNA in the presence of the DNA polymerase of the invention, as compared to the case of its absence.

In the second DNA synthesis method of the invention, a single DNA polymerase-related factor or a mixture of two or more may be used. The mixed use of two or more is preferable.

Examples of DNA polymerase-related factors usable in the second DNA synthesis reaction of the invention include KOD-PCNA, KOD-RFCS and KOD-RFCL. For example, when using KOD-PCNA, the DNA elongation rate can be increased several fold, compared to a reaction with single use of KOD DNA polymerase. The above three types of DNA polymerases can be used singly or as a KOD-RFC complex comprising KOD-RFCS and KOD-RFCL (heteropentamer of RFCS:RFCL=1:4) or a PCNA-RFC complex comprising KOD-PCNA and KOD-RFC.

Examples of DNA polymerases usable in the second DNA synthesis method of the invention include DNA polymerases such as pol I derived from *E. coli*; and thermostable DNA polymerases such as Tth DNA polymerase derived from *Thermus thermophilus*, Taq DNA polymerase derived from *Thermus aquaticus*, Pfu DNA polymerase derived from *Pyrococcus furiosus*, and DNA polymerase derived from *Thermococcus kodakaraensis* (KOD DNA polymerase). Thermostable DNA polymerases are preferable. In particular, DNA polymerases derived from hyperthermophilic archaea, more specifically DNA polymerases from the hyperthermophilic archaeon *Thermococcus kodakaraensis* (KOD DNA polymerase) are preferable. When *Thermococcus kodakaraensis* polymerase and the DNA polymerase-related factor of the invention are used in combination, the origin of the DNA polymerase and the DNA polymerase-related factor is the same so that not only a high DNA elongation rate and excellent processability but also high DNA synthesis fidelity, which is a characteristic of KOD DNA polymerase, can be obtained, so that particularly excellent effects can be expected. In the DNA synthesis method of the invention, single DNA polymerases or a mixture of two or more can be used.

DNA can be synthesized by PCR methods using the second DNA synthesis method of the invention. For example, a method of performing PCR has been reported using a DNA polymerase composition prepared by mixing Pfu polymerase having 3'-5' exonuclease activity, Tli polymerase and these variant enzymes as a method for amplifying long chain nucleic acids (Barns, W. M. Proc. Natl. Acad. Sci. USA, 91, (1994) 2216-2220). A method of performing PCR using a DNA polymerase composition prepared by mixing Tth polymerase not having 3'-5' exonuclease activity, Pfu polymerase having 3'-5' exonuclease activity or Tli polymerase, and *Thermotaga maritima*-derived thermostable DNA polymerase has also been reported (Japanese Unexamined Patent Publication No. H8 (1996)-38198).

However, although these compositions provide improved amplification efficiency as compared to the use of one type of DNA polymerase, sufficient amplification efficiency can not achieved because they comprise two types of DNA polymerases that differ in thermostability and DNA elongation rate.

Therefore, the present inventors carried out extensive research and developed a novel mixed type thermostable DNA polymerase (KOD Dash DNA polymerase) prepared by mixing a 3'-5' exonuclease activity-deleted KOD (exo-) DNA polymerase and a KOD DNA polymerase (Japanese Unexamined Patent Publication No. H10 (1998)-42874). This KOD Dash DNA polymerase appeared to be the optimal form of a mixed type enzyme and further improvement seemed impossible.

However, even in the case of this enzyme, further enhanced PCR performance was achieved by adding a DNA polymerase-related factor of the invention derived from the same origin as the enzyme (see Example 15). Mixed enzymes using two types of DNA polymerases also achieve improved effects with the addition of the DNA polymerase-related factor. When a mixed DNA polymerase derived from the same origin as the DNA polymerase-related factor (here KOD dash), further improved effects are obtained.

In the second DNA synthesis method of the invention, the amount of the DNA polymerase-related factor to be used is not particularly limited. The DNA polymerase-related factor may be used in an amount sufficient to promote the synthesis activity of a DNA polymerase.

(XI) DNA Synthesis Kit Comprising a DNA Polymerase-Related Factor (Second DNA Synthesis Kit)

The DNA synthesis kit comprising the DNA polymerase-related factor of the invention is a kit comprising the DNA polymerase-related factor (comprising one or more of the proteins (e) to (j)) of the invention and a DNA polymerase. The kit may comprise one or more other components as necessary for DNA synthesis. Examples of other components necessary for DNA synthesis include 4 types of nucleotides or nucleotide derivatives such as dNTP, buffers, salts such as $MgCl_2$, and additives useful for DNA synthesis, primers, and the like. These are described above. Such components may be entirely contained in one part of the kit or separately contained in two or more parts.

This kit may be used for various reactions in which a DNA polymerase is used. Thus it may be a kit for performing in vitro DNA synthesis reactions, a kit for performing DNA base sequencing, for instance, by the dideoxy method, a DNA labeling kit or a PCR kit.

DNA polymerase-related factors preferably contained in the kit of the invention are, for example, KOD-PCNA, KOD-RFCS and KOD-RFCL. In the kit of the invention, the three types of DNA polymerase-related factors may be mixed singly with KOD polymerase or used as a KOD-RFC complex comprising KOD-RFCS and KOD-RFCL (heteropentamer of RFCS:RFCL=1:4) or a PCNA-RFC complex comprising KOD-PCNA and KOD-RFC.

Examples of DNA polymerases contained in the kit of the invention include DNA polymerases such as pol I derived from *E. coli*; and thermostable DNA polymerases such as Tth DNA polymerase derived from *Thermus thermophilus*, Taq DNA polymerase derived from *Thermus aquaticus*, Pfu DNA polymerase derived from *Pyrococcus furiosus*, and DNA polymerase derived from *Thermococcus* kodakaraensis (KOD DNA polymerase). In the kit of the invention, thermostable DNA polymerases are preferable. Especially preferable are DNA polymerases derived from hyperthermophilic archaea. Specific examples thereof include DNA polymerases from *Thermococcus kodakaraensis* (KOD DNA polymerase).

By performing the above DNA synthesis method using the kit of the invention, DNA can be synthesized more quickly in a more convenient and highly sensitive manner.

EXAMPLES

The present invention is described in more detail in the Examples below. However, it should be understood that the present invention is not limited to these Examples.

Example 1-1

Investigation of the Effect of Oxalate Ion Addition to Mixed Type Enzyme (EX-Taq) (FIG. 1)

The effect produced by the addition of oxalate ions was investigated in the PCR using EX-Taq DNA polymerase. A PCR buffer supplied with EX-Taq (TAKARA) and 0.3 µM of a pair of primers of SEQ ID Nos:8 and 9 and 0.2 mM dNTPs were used. PCR was performed by using 1.0 U EX-Taq DNA polymerase and 20 ng of genomic DNA derived from human cell line K562 as a template, with the influence on the PCR result caused by varying the concentration of added oxalate ion being investigated. The PCR conditions were as follows: 1 preliminary reaction of 94° C. for 2 minutes, and then 35 cycles of 94° C. for 15 seconds, 60° C. for 30 seconds and 68° C. for 8.5 minutes. This PCR amplification was performed by using GeneAmp2400 (PE Applied Biosystems).

FIG. 1 shows the electrophoresis pattern of the PCR product. It was found that the target DNA was not amplified in the absence of oxalate ion, but the DNA was amplified when 1 mM oxalate ion was added, and the amount of amplification was the highest when 2-3 mM oxalate ion was added. The amplification of the target DNA was confirmed with the addition of oxalate ion in an amount ranging from 1-4 mM.

These results demonstrate the effect produced by the addition of oxalate ion to the mixed type enzyme. The concentration range of oxalate ion within which the effect of the addition is found is up to 4 mM, but it is expected that the optimal concentration varies depending on the kind and amplification length of the target DNA, PCR buffer composition, etc.

Example 1-2

Investigation of the Type of Salt which is Effective for PCR Using Mixed Type Enzyme (EX-Taq)(FIG. 2)

Salts (potassium chloride, potassium acetate, potassium oxalate, sodium oxalate, potassium sulfate) were investigated for their effectiveness in PCR using EX-Taq DNA polymerase under the same conditions as Example 1. Each salts was used in an amount of 4 to 6 mM of ion equivalent FIG. 2 shows the electrophoresis patterns of the PCR products. Amplification was observed only when potassium oxalate or sodium oxalate was added as a salt. Amplification was not observed when other presently widely used potassium salts were added. These results suggest that the oxalate anions are effective for PCR.

Example 1-3

Investigation of the Type of Carboxylate Salt Effective for PCR Using Mixed Type Enzyme (EX-Taq)(FIG. 3)

The type of carboxylate salts (potassium oxalate, sodium oxalate, potassium succinate, potassium formate) that is effective for PCR using EX-Taq DNA polymerase was investigated under the same conditions as Example 2.

FIG. 3 shows the electrophoresis patterns of the PCR products. As in Example 2, amplification of the target DNA was observed only when potassium oxalate or sodium oxalate was added as a salt. A similar effect to that produced by oxalate salts was not observed with formate having a monovalent carboxyl group, or succinate having a divalent carboxyl group. However, compared to oxalates, potassium formate and potassium succinate may have a different concentration range that is effective for PCR amplification. Therefore, the effectiveness of these salts cannot be completely ruled out. It is assumed that in certain concentration ranges, other carboxylate salts might possibly be effective for PCR.

Example 1-4

Investigation of the Effect of *Oxalate Ions* Addition to PolI Type Enzyme (Tag)

The effect produced by the addition of oxalate ions was investigated in PCR using Taq DNA polymerase. A PCR buffer (10 mM Tris-HCl (pH 8.3), 50 mM KCl, 1.5 mM $MgCl_2$) attached to Taq (TOYOBO CO., LTD.), 0.2 mM dNTPs and 0.3 µM of a primer pair were used. A pair of primers of SEQ ID Nos:10 and 11 was used for the PCR amplification of a 3.6-kb DNA of β-globin cluster (the electrophoresis pattern of its PCR product is shown in FIG. 4), while a pair of primers of SEQ ID Nos:12 and 13 was used for the PCR amplification of a 4.5-kb DNA of myelin oligodendrocyte glycoprotein (the electrophoresis pattern of its PCR product is shown in FIG. 5). The influence of varying the concentration of oxalate ions added on the PCR results was investigated using 2.5 U Taq DNA polymerase and 20 ng of Genomic DNA derived from cultured human cell K562 as a template. The PCR conditions were as follows: 94° C. for 2 minutes as 1 preliminary reaction, and then 30 cycles of 94° C. for 15 seconds, 60° C. for 30 seconds and 68° C. for 8 minutes. The PCR amplification was performed by using GeneAmp 2400 (PE Applied Biosystems).

When no oxalate ions were added, the electrophoresis patterns of all the target sequences showed only a smear. However, in the PCR amplification of 3.6-kb DNA of β-globin, when 2 mM oxalate ion was added, amplification of the target sequence was observed together with a smear, and when 4 mM oxalate ion was added, no smear was observed. With the addition of 4-5 mM oxalate ion, a discrete amplification band was observed. In the PCR amplification of 4.5-kb DNA of myelin oligodendrocyte glycoprotein electrophoresis patterns, amplification of the target DNA was observed together with a smear when 1 mM oxalate ion was added, and when 2 mM oxalate ion was added, no smear was observed. A discrete amplification band of the target DNA was confirmed with the addition of 2-5 mM oxalate ion.

These results demonstrate the effect produced by the addition of oxalate ion to the Pol I enzyme. The concentration range within which the effect of the addition of oxalate ion is found was up to 5 mM, but it is expected that the optimal concentration varies depending on the kind and amplification length of the target DNA, PCR buffer composition, etc.

Example 1-5

Investigation of the Effect of Oxalate Ion Addition to α-Type Enzyme (Native Pfu)(FIG. 6)

The effect produced by the addition of oxalate ion in PCR was investigated using nPfu polymerase. A PCR buffer (20 mM Tris-HCl (pH 8.75), 10 mM KCl, 10 mM $(NH_4)_2SO_4$, 2 mM MgSO$_4$, 0.1% Triton X-100, 100 μg/ml BSA) attached to nPfu (STRATAGENE), 0.2 mM of dNTPs, and 0.3 μM of a pair of primers of SEQ ID NOs:12, and 13 were used. PCR was performed by using 2.5 U nPfu DNA polymerase and 20 ng of genomic DNA derived from human cell line K562 as a template, with the influence on the PCR result caused by varying the concentration of oxalate ion being investigated. PCR was performed by using Gene-Amp2400 (PE Applied Biosystems) with the following conditions: 1 preliminary reaction of 94° C. for 2 minutes, and then 35 cycles of 94° C. for 15 seconds, 60° C. for 30 seconds and 68° C. for 8 minutes.

The electrophoresis patterns of the PCR products are shown in FIG. 6. When no oxalate ions were added, only a smear was shown. However, when 2-5 mM oxalate ion was added, amplification of the target DNA was observed. These results demonstrate the effect produced by the addition of oxalate ion on the α-type enzyme. The concentration range within which the effect of the addition of oxalate ion is found is approximately up to 5 mM, but it is expected that the optimal concentration varies depending on the kind and size of amplified portion of the target DNA, PCR buffer composition, etc.

Example 1-6

Investigation of the Type of Salt which is Effective for PCR Using α-Type Enzyme (Native Pfu)(FIG. 7)

Salts (potassium chloride, potassium acetate, potassium oxalate, potassium sulfate) were tested for their effectiveness in PCR using nPfu DNA polymerase under the same conditions as Example 1-5. The amount of each salt used was 4-6 mM of ion equivalent, as was the most effective in Example 1-5.

The electrophoresis patterns of the PCR products are shown in FIG. 7. When potassium salts (potassium chloride, potassium acetate, potassium oxalate, potassium sulfate), which are widely used today, were added, amplification of the target DNA was not observed, and only when potassium oxalate was added, was amplification of the target DNA observed. These results demonstrate that oxalate anions are effective for PCR.

Example 1-7

Investigation of the Effect Produced by the Addition of Oxalate Ion to Hot Start Enzyme (KOD-plus)(FIG. 8)

The effect produced by the addition of oxalate ion to a hot start enzyme was investigated using a hot start enzyme KOD-plus DNA polymerase containing KOD α-type enzyme) and two kinds of KOD antibodies. The PCR buffer supplied with KOD-plus (manufactured by Toyobo), 0.2 mM dNTPs and 0.3 μM of a primer pair of SEQ ID Nos:8 and 9 were used. PCR was performed using 2.5 U KOD-plus DNA polymerase and 20 ng of Genomic DNA derived from human cell line K562 as a template to investigate the influence of varying the concentration of oxalate ion added on the PCR results. The PCR conditions were as follows: 1 preliminary reaction of 94° C. for 2 minutes, and then 35 cycles of 94° C. for 15 seconds, 60° C. for 30 seconds and 68° C. for 8.5 minutes. The PCR was performed using GeneAmp2400 (PE Applied Biosystems).

The electrophoresis patterns of the PCR products are shown in FIG. 8. In the absence of oxalate ion, many extra bands were observed, but in the presence of potassium oxalate, no extra bands were observed and only the target DNA was amplified. The optimal concentration of potassium oxalate was about 3 mM. When 5 mM of potassium oxalate was added, a decrease in the amount of the target DNA amplified was found.

These results demonstrate the effect produced by the addition of oxalate ion to the hot start enzyme. The concentration range within which the effect of the addition of oxalate ion is found is approximately up to 5 mM, but it is expected that the optimal concentration varies depending on the kind and size of amplified portion of the target DNA, PCR buffer composition, etc.

Example 1-8

Investigation of the Type of Salt which is Effective for PCR Using Hot Start Enzyme (KOD-plus)(FIG. 9)

Salts (potassium chloride, potassium acetate, potassium formate, potassium oxalate, sodium oxalate, potassium succinate, potassium sulfate) were tested for their effectiveness in PCR using KOD-plus DNA polymerase under the same conditions as Example 1-7. The amount of each salt used was 6 mM of ion equivalent, as was the most effective in Example 1-7.

The electrophoresis patterns of the PCR products are shown in FIG. 9. Amplification of the target DNA was not observed when other presently widely used potassium salts (potassium chloride, potassium acetate, potassium oxalate, potassium sulfate) were added. Amplification was observed only when potassium oxalate or sodium oxalate was added.

Potassium formate and potassium succinate, whose chemical formulas are relatively similar to that of oxalate, were also investigated, but similar effects to those of oxalate were not found. However, compared to oxalate, potassium formate and potassium succinate may have a different concentration range that is effective for PCR amplification. Therefore, the effectiveness of these salts cannot be completely ruled out. It may be assumed that in certain concentration ranges, other carboxylate salts might be effective for PCR.

These results demonstrate the effect produced by the addition of oxalate anions to the hot start enzyme.

Example 1-9

Investigation of the Effect Produced by the Addition of Malonic Acid Ion and Maleic Acid Ion to Hot Start Enzyme (KOD-plus)(FIG. 10)

The type of salts other than oxalates (sodium malonate, sodium maleate) were tested for their effectiveness in PCR under the same conditions as Example 1-7.

The electrophoresis patterns of the PCR products are shown in FIG. 10. When 2 mM of sodium malonate was added, the extra bands tended to decrease, and when 6 mM was added, most of the extra bands disappeared, indicating amplification of only the target DNA was observed.

Similarly, when 4 mM of sodium maleate was added, extra bands tended to decrease, and when 10 mM was added, most of the extra bands disappeared, indicating amplification of only the target DNA.

These results demonstrate the effect produced by the addition of malonate and maleate, which are both dicarboxylates. The concentration ranges of these salts within which the effects of the addition are found were higher than that of oxalate. It is expected that the optimal concentration of each of the dicarboxylic acids varies depending on the kind and amplification length of the target DNA, PCR buffer composition, etc.

Example 2-1

Investigation of Synergistic Effects Produced by the Addition of Oxalate Ion and Betaine to Mixed-Type Enzyme (EX-Taq)(FIG. 11)

Oxalate ion and betaine were investigated for their synergistic effectiveness in amplification of a target DNA which cannot be usually amplified by PCR using EX-Taq DNA polymerase (TAKARA). Potassium oxalate was added to the PCR buffer attached to EX-Taq DNA polymerase to attain a final concentration of 2 mM. Also used were 0.2 mM dNTPs, 0.3 µM of a pair of primers consisting of the sequences of ID NOs:14 and 15 respectively, and 1.0 U EX-Taq DNA polymerase. 20 ng of genomic DNA derived from human cell line K562 was used as a template. This reaction mixture was subjected to PCR by using Gene-Amp2400 (PE Applied Biosystems) to investigate the influence of varying the concentration of betaine added on the PCR results. The PCR conditions were as follows: 1 preliminary reaction of 94° C. for 2 minutes, and then 35 cycles of 94° C. for 15 seconds, 60° C. for 30 seconds and 68° C. for 8.5 minutes.

The electrophoresis patterns of the PCR products are shown in FIG. 11. In the absence of betaine, amplification of the target DNA was barely noticeable. In the presence of 0.5 M betaine, an increase in amplification amount was observed. These results demonstrate a synergistic effect produced by the addition of oxalate ion and betaine to the mixed-type enzyme.

Example 2-2

Investigation of Synergistic Effects Produced by the Addition of Oxalate Ion and Betaine to α-Type Enzyme (Native Pfu)(FIG. 12)

Oxalate ion and betaine were investigated for their synergistic effectiveness in amplification of a target DNA which cannot be usually amplified by PCR using nPfu polymerase. Potassium oxalate was added to the PCR buffer (20 mM Tris-HCl(pH: 8.75), 10 mM KCl, 10 mM $(NH_4)_2SO_4$, 2 mM $MgSO_{4,}$ 0.1% Triton X-100, 100 µg/ml BSA) supplied with nPfu (STRATAGENE) to attain a final concentration of 2 mM. Also used were 0.2 mM dNTPs, 0.3 µM of a pair of primers of SEQ ID Nos:16 and 17, and 2.5 U nPfu DNA polymerase. 20 ng of genomic DNA derived from human cell line K562 was used as a template. This reaction mixture was subjected to PCR by using GeneAmp2400 (PE Applied Biosystems) to investigate the influence of varying the concentration of betaine added on the PCR results. The PCR conditions were as follows: 1 preliminary cycle of 94° C. for 2 minutes, and then 35 cycles of 94° C. for 15 seconds, 60° C. for 30 seconds and 68° C. for 8.5 minutes.

The electrophoresis patterns of the PCR products are shown in FIG. 12. When no betaine was added, the electrophoresis patterns of the target DNA showed only a smear. However, when 0.5 mM of betaine was added, amplification of the target DNA was observed. These results demonstrate a synergistic effect produced by the addition of oxalate ion and betaine to α-type enzyme.

Example 2-3

Investigation of Synergistic Effects Produced by the Addition of Oxalate Ion and Betaine to Hot Start Enzyme (KOD-plus)(FIG. 13)

Oxalate ion and betaine were investigated for their synergistic effectiveness in amplification of a target DNA which cannot be amplified by normal PCR, using KOD-plus DNA polymerase, i.e. a hot start enzyme which is a mixture of KOD (α-type enzyme) and two kinds of KOD antibodies. Potassium oxalate was added to the PCR buffer supplied with KOD-plus (TOYOBO CO., LTD.) to attain a final concentration of 2 mM. Also used were 0.2 mM dNTPs and 0.3 µM of a pair of primers of SEQ ID NOs: 14 and 15. 20 ng of genomic DNA derived from human cell line K562 was used as a template. This reaction mixture was subjected to PCR by using GeneAmp2400 (PE Applied Biosystems) to investigate the influence of varying the concentration of betaine on the PCR results. The PCR conditions were as follows: 1 preliminary reaction of 94° C. for 2 minutes, and then 35 cycles of 94° C. for 15 seconds, 60° C. for 30 seconds and 68° C. for 8.5 minutes.

The electrophoresis patterns of the PCR products are shown in FIG. 13. When no betaines were added, amplification of the target DNA was barely noticeable. However, when 0.5-1.5 M of betaine was added, an increased amount of amplification of the target DNA was observed. The amount of amplification was greatest when 1.5 M of betaine was added.

These results demonstrate a synergistic effect produced by the addition of oxalate ion and betaine to the hot start enzyme.

Example 2-4

Investigation of Synergistic Effects of Oxalate Ion and DMSO with Hot Start Enzyme (KOD-plus)(FIG. 14)

Oxalate ion and DMSO were investigated for their synergistic effectiveness for hot start enzyme in amplification of a target DNA which is difficult to amplify by usual PCR, using a KOD-plus DNA polymerase, i.e., hot start enzyme. Potassium oxalate was added to the PCR buffer supplied with KOD-plus (TOYOBO CO., LTD.) to attain a final concentration of 2 mM. Also used were 0.2 mM dNTPs and 0.3 mM of a pair of primers of SEQ ID Nos:18 and 19, and 1.0 U KOD-plus DNA polymerase. 0.5 µL of cDNA obtained by reverse transcription of 500 ng of total RNA derived from human cell line K562 with ThermoScript (Invitrogen) was used as a template. This reaction mixture was subjected to PCR by using GeneAmp2400 (PE Applied Biosystems) to investigate the influence on the PCR results of varying the concentration of DMSO. The PCR conditions were as follows: 1 preliminary reaction of 94° C. for 2 minutes, and then 40 cycles of 94° C. for 15 seconds, 60° C. for 30 seconds and 68° C. for 9 minutes.

The electrophoresis patterns of the PCR products are shown in FIG. 14. In the absence of DMSO, amplification of the target DNA was barely noticeable. In the presence of DMSO, an increase in amplification amount was observed.

In the presence of 5% DMSO, sufficient amplification was observed. These results demonstrate a synergistic effect produced by the addition of oxalate ions and DMSO to the hot start enzyme.

Example 2-5

Investigation of Synergistic Effects Produced by the Addition of Potassium Oxalate and Betaine on Long PCR Using α-Type Enzyme (KOD)(FIG. 15)

Oxalate ion and betaine were investigated for their synergistic effectiveness in long PCR amplification of a target DNA of more than 20 kb derived from the human genome using KOD DNA polymerase, successful amplification of which using α-type enzyme alone has not been reported. Potassium oxalate was added to the PCR buffer supplied with KOD-plus (TOYOBO CO.,LTD.) to attain a final concentration of 2 mM. Also used were 0.4 mM dNTPs, 0.3 µM of a pair of primers of SEQ ID Nos:20 and 21, and 2.0 U KOD DNA polymerase. 200 ng of genomic DNA derived from human cell line K562 was used as a template. This reaction mixture was subjected to PCR by using Gene-Amp2400 (PE Applied Biosystems) to investigate the influence on the PCR results of varying the concentration of betaine. The PCR conditions were as follows: 1 preliminary reaction of 94° C. for 2 minutes; 5 cycles of 98° C. for 10 seconds and 74° C. for 18 minutes; 5 cycles of 98° C. for 10 seconds and 72° C. for 18 minutes; 5 cycles of 98° C. for 10 seconds and 70° C. for 18 minutes; 25 cycles of 98° C. for 10 second and 68° C. for 18 minutes; and 1 additional reaction of 68° C. for 7 minutes.

The electrophoresis patterns of the PCR products are shown in FIG. 15. When the betaine concentration was 1.2 M or less, amplification of the target DNA was not observed, while sufficient amplification was found when 1.4 M or 1.6 M betaine was used. The amount of betaine used is not limited to the above concentration however, since the optimal concentration of betaine varies depending on the kind of enzyme used.

Example 2-6

Investigation of Synergistic Effects Produced by the Addition of Betaine and Potassium Oxalate in Long PCR Using α-Type Enzyme (KOD)(FIG. 16)

Oxalate ion and betaine were investigated for their synergistic effectiveness in long PCR amplification of a target DNA of more than 20 kb derived from the human genome using KOD DNA polymerase, successful amplification of which using α-type enzyme alone has not been reported. Betaine was added to the PCR buffer supplied with KOD-plus (TOYOBO CO., LTD.) to attain a final concentration of 1.5 M. Also used were 2.0 U KOD DNA polymerase, 0.4 mM dNTPs and 0.3 µM of a pair of primers of SEQ ID Nos:22 and 23 respectively for the PCR amplification of 22 kb DNA in tPA gene, and SEQ ID Nos:22 and 24 respectively for the PCR amplification of tPA 24 kb DNA. 200 ng of genomic DNA derived from human cell line K562 was used as a template. This reaction mixture was subjected to PCR by using GeneAmp2400 (PE Applied Biosystems) to investigate the influence on the PCR results of varying the concentration of potassium oxalate. The PCR conditions were as follows: 1 preliminary reaction of 94° C. for 2 minutes; 5 cycles of 98° C. for 10 seconds and 74° C. for 18 minutes; 5 cycles of 98° C. for 10 seconds and 72° C. for 18 minutes; 5 cycles of 98° C. for 10 seconds and 70° C. for 18 minutes; 25 cycles of 98° C. for 10 seconds and 68° C. of 18 minutes; and 1 additional reaction of 68° C. for 7 minutes.

The electrophoresis patterns of the PCR products are shown in FIG. 16. When tPA 22 kb DNA was the target, its amplification was confirmed only when 2 mM potassium oxalate was added. When tPA 24 kb DNA was the target, slight amplification was observed, when 1.5 mM or 2.0 mM potassium oxalate was added. The amount of potassium oxalate used is not limited to the above concentration however, since the optimal concentration of potassium oxalate varies depending on the kind of enzyme used.

Example 2-7

Investigation of the Effect Produced by Hot Start PCR in Long PCR (FIG. 17)

Under the aforementioned conditions in which oxalate ions and betaine are present, the effect of hot start PCR using antibodies in long PCR using KOD DNA polymerase was investigated. Potassium oxalate and betaine were added to the PCR buffer supplied with KOD-plus (TOYOBO CO.LTD.) to attain a final oxalate concentration of 2 mM and a final betaine concentration of 1.5 M. Also used were 2.0 U KOD DNA polymerase, 0.4 mM dNTPs and 0.3 µM of a pair of primers of SEQ ID Nos:22 and 25 for PCR amplification of tPA 12 kb DNA; SEQ ID Nos:22 and 26 for PCR amplification of tPA 15 kb DNA; SEQ ID Nos:22 and 27 for PCR amplification of tPA 18 kb DNA; SEQ ID Nos:22 and 23 for PCR amplification of tPA 22 kb DNA; SEQ ID Nos:22 and 24 for PCR amplification of tPA 24 kb DNA; and SEQ ID Nos:28 and 29 for PCR amplification of β-globin 17.5 kb DNA. 200 ng of genomic DNA derived from human cell line K562 was used as a template. This reaction mixture was subjected to PCR by using Gene-Amp24000 (PE Applied Biosystems) to investigate the effect of hot start PCR in the presence or absence of antibodies. The PCR conditions were as follows: 1 preliminary reaction of 94° C. for 2 minutes; 5 cycles of 98° C. for 10 seconds and 74° C. for 18 minutes; 5 cycles of 98° C. for 10 seconds and 72° C. for 18 minutes; 5 cycles of 98° C. for 10 seconds and 70° C. for 18 minutes; 25 cycles of 98° C. for 10 seconds and 68° C. for 18 minutes; and 1 additional reaction of 68° C. for 7 minutes.

The electrophoresis patterns of the PCR products are shown in FIG. 17. Evaluation of the patterns of 6 type target DNAs revealed that the use of antibodies decreased smearing and increased their amplification amounts in general. In particular, in the amplification of tPA 22 kb target DNA, amplification of the target DNA was not observed when no antibodies were used, but amplification was confirmed when antibodies were present. Although it was expected that hot start PCR would also be effective for long PCR, there has been no example which demonstrates this to date. Therefore, this is supposed to be the first such report of amplification of human genomic target DNA of 20 kb or more.

Example 2-8

Investigation of the Effects of a Reagent Which is Effective for PCR of a GC Rich Target DNA for Long PCR (FIG. 18)

The reagent "PCRx" (Invitrogen), which is considered to be effective for target DNAs with a high GC content, and betaine were investigated to see whether they are similarly effective for long PCR. Potassium oxalate was added to the buffer supplied with KOD-plus (TOYOBO CO.,LTD.) to attain a final concentration of 2 mM. Also used were 1.0 U KOD DNA polymerase, 0.4 mM dNTPs and 0.3 µM of a pair of primers of SEQ ID Nos:30 and 31 was used for PCR amplification of tPA 9 kb DNA, and a pair of primers SEQ ID Nos:22 and 23 was used for PCR amplification of tPA 12 kb DNA. 200 ng of genomic DNA derived from human cell line K562 was used as a template. This reaction mixture was subjected to PCR by using GeneAmp2400 (PE Applied Biosystems) to compare the effects produced by the addition of betaine and PCRx. The PCR conditions were as follows: a preliminary cycle of 94° C. for 2 minutes; 5 cycles of 98° C. for 10 seconds and 74° C. for 12 minutes; 5 cycles of 98° C. for 10 seconds and 72° C. for 12 minutes; 5 cycles of 98° C. for 10 seconds and 70° C. for 12 minutes; 25 cycles of 98° C. for 10 seconds and 68° C. for 12 minutes; and finally an additional reaction of 68° C. for 7 minutes.

The electrophoresis patterns of the PCR products are shown in FIG. 18. When no additives were used, amplification of both the tPA 9 kb and 12 kb target DNAs was barely observed. However, sufficient amplification of both target DNAs was observed when 1 M or 1.5 M betaine was added. In contrast, when PCRx was used in a 1×, 2× or 3× concentration according to the instruction manual, no amplification was observed. These results demonstrate that the reagent, which is effective for GC rich targets, is not always effective for long PCR and that the effectiveness for long PCR is a property specific to betaine. The effects of betaine for long PCR have been confirmed not only with α-type DNA polymerase also with all the heat-resistant DNA polymerases.

Example 3-1

Cloning of the Gene Coding for DNA Polymerase-Related Factor Derived from Hyperthermophilic Archaeon KOD1

Hyperthermophilic archaeon KOD1, isolated from Kodakara Island, Kagoshima, Japan, was cultured at 95° C. and cells were collected. Chromosomal DNA of hyperthermophilic archaeon KOD1 was prepared from the obtained cells in the standard manner. Primer pairs were synthesized based on the amino acid sequences of conserved regions of PCNA (proliferating-cell-nuclear-antigen), RFCS (replication C small subunit) and RFCL (replication C large subunit), which are known as DNA polymerase-related factors. The primer pair of PCNA-f1 (SEQ ID NO:32) and PCNA-r1 (SEQ ID NO: 33) was used for PCR amplification of the KOD-PCNA gene. The primer pair of RFCS-f1 (SEQ ID NO:34) and RFCS-r1 (SEQ ID NO:35) was used for PCR amplification of the KOD-RFCS gene. The primer pair of RFCL-f1 (SEQ ID NO:36) and RFCL-r1 (SEQ ID NO:37) was used for PCR amplification of the KOD-RFCL gene. PCR was performed by using these primer pairs and the prepared chromosomal DNA as a template. All the PCR operations hereinafter were carried out by using KOD-Plus (TOYOBO CO.,LTD.) according to the usage examples supplied with the enzyme. The nucleotide sequences of DNA fragments amplified by PCR were determined by the dideoxy chain termination method, whereby each DNA fragment was found to have its own conserved sequence (SEQ ID Nos:38, 39 and 40 respectively).

By the in vitro packaging method using DNA fragments obtained by digesting chromosomal DNA of hyperthermophilic archaeon KOD1 by EcoRI and Gigapack Gold (Stratagene), a cosmid having chromosomal DNA of hyperthermophilic archaeon KOD1 was packed in λ phage particles, constructing a phage DNA library.

Plaque hybridization was performed by using a DNA fragment containing KOD-PCNA as a probe to obtain from the above-mentioned library phage clone PCNA/λ, which is considered to contain a PCNA gene derived from KOD1. Phage clone RFCS/λ and RFCL/λ, which are considered to contain RFCS and RFCL genes, respectively, were obtained in a similar manner.

Cloning method of the polymerase-related factor genes derived from hyperthermophilic archaeon KOD1 and the expression vector construction method are shown in FIG. 19.

Example 3-2

Determination of Nucleotide Sequences of Clone Fragments

Phage direct PCR was performed using the primer pair of PCNA-f1 and PCNA-r1 and phage clone PCNA/λ as a template, obtaining amplified DNA fragments. Direct sequencing of the obtained amplification fragments was carried out to determine the nucleotide sequences of the gene. With regard to the 5' end and 3' end of the gene, primer λ L1 (SEQ ID NO:41) was synthesized from the nucleotide sequence in the left arm of the λ vector, and λ R1 (SEQ ID NO:42) was synthesized from the nucleotide sequence in the right arm of the λ vector. These primers were used with the primers PCNA-f2 (SEQ ID NO:43) and PCNA-r2 (SEQ ID NO:44), which were newly synthesized inside the gene. Phage direct PCRs were performed using a primer pair of λL1 or λR1 and PCNA-f2 or PCNA r2 respectively, and phage clone PCNA/λ as a template, obtaining amplified DNA fragments including the 5' end and 3' end respectively. Similarly, direct sequencing of the amplified fragments including the 5' end and 3' end respectively was carried out to determine the nucleotide sequences of the 5' end region and the 3' end region of the gene.

Similar operations to those described above were performed using each of the genes RFCS and RFCL. In detail, either the primer λ L1 (SEQ ID NO:41) or λ R1 (SEQ ID NO:42), and one of the newly synthesized primers RFCS-f2 (SEQ ID NO:45), RFCS-r2 (SEQ ID NO:46), RFCL-f2 (SEQ ID NO:47) and RFCL-r2 (SEQ ID NO:48) were synthesized and phage direct PCR was performed. Thus, DNA fragments including the 5' end region and DNA fragments including the 3' end region were obtained, and entire nucleotide sequences were determined by direct sequencing.

The KOD-PCNA gene (SEQ ID NO:3) consists of 750 bases, and codes for 249 amino acids (SEQ ID NO:2). The KOD-RFCL gene (SEQ ID NO: 5) consists of 1500 bases, and codes for 499 amino acids (SEQ ID NO: 4). The KOD-RFCS gene (SEQ ID NO: 7) consists of 2601 bases, and codes for 866 amino acids (SEQ ID NO: 6).

The homology comparison results of nucleotide sequence and protein amino acid sequence between KOD-PCNA and PCNA derived from Archaea are shown in Table 1 below.

The homology comparison results of nucleotide sequence and protein amino acid sequence between KOD-RFCS and RFCS derived from Archaea are shown in Table 2 below. The homology comparison results of nucleotide sequence and protein amino acid sequence between KOD-RFCL and RFCL derived from Archaea are shown in Table 3 below.

TABLE 1

Comparison with PCNA derived from *Archaea*
PCNA derived from *Thermococcus kodakaraensis* KOD1
ORF: 750 bp, 249 aa
Estimated molecular weight of monomer: 28.2 kD

| Origin | DNA length | | A.A. length | |
|---|---|---|---|---|
| Pfu | 71.1% | 750 b | 84.3% | 249 aa |
| Pho | 69.7% | 750 b | 83.5% | 249 aa |
| Tfu | 83.1% | 750 b | 91.2% | 249 aa |

Pfu: *P. furiosus*, Pho: *P. horikoshii*, Tfu: *T. fumicolans*

TABLE 2

Comparison with RFCS gene derived from *Archaea*
RFCS derived from *Thermococcus kodakaraensis* KOD1
ORF: 981 bp, 326 aa
Estimated molecular weight: 37.2 kD

| Origin | DNA length | | A.A. length | |
|---|---|---|---|---|
| Afu | 61.9% | 960 b | 58.7% | 319 aa |
| Mth | 63.9% | 966 b | 60.7% | 321 aa |

Afu: *A. fulgidus*, Mth: *M. thermoautotrophicum*

TABLE 3

Comparison with RFCL derived from *Archaea*
RFCL derived from *Thermococcus kodakaraensis* KOD1
ORF: 1500 bp, 499 aa
Estimated molecular weight: 57.2 kD

| Origin | DNA length | | A.A. length | |
|---|---|---|---|---|
| Pfu | 67.5% | 1440 b | 71.5% | 479 aa |
| Pho | 67.8% | 1412 b | 74.6% | 469 aa |

Pfu: *P. furiosus*, Pho: *P. horikoshii*

Example 3-3

Construction of Mature KOD-RFCS Gene

KOD-RFCS takes a in which the conserved region III of RFCS is divided, and an intervening sequence (KOD-RFCS Intein), which consists of 1620 bases (539 amino acids), is inserted into this portion. The structures of the RFCS and RFCL genes are shown in FIG. 20, and a comparison of the amino acid sequence of RFCS is shown in FIG. 21. This intervening sequence was compared with that derived from Archaea which also have an intervening sequence in RFCS and found a high degree of homology, 60-75% homology at the DNA level and 58-71% homology at the amino acid level. The results are shown in Table 4 below.

TABLE 4

Homology comparison of RFCS Intein
RFCS derived from *Thermococcus kodakaraensis* KOD1
ORF: 1620 bp, 539 aa
Estimated molecular weight: 52.5 kD

| Origin | DNA Identities | | A.A. Identities | |
|---|---|---|---|---|
| Pho | 75% | 626/840 | 71% | 383/539 |
| Pab | 65% | 331/509 | 56% | 302/539 |
| Mja | 60% | 510/857 | 58% | 322/548 |

Pho: *P. horikoshii* probable replication factor C subunit
Pba: *P. abbysi* replication factor C, small chain
Mja: *M. jannaschii* replication factor C homolog This sequence was deleted by the In-Fusion PCR cloning method.

Two fragments from which the intervening sequence had been deleted were amplified by the In-Fusion PCR cloning method using a phage clone as a template and each of 2 pairs of primers: NdeI-mRFCS and ΔRFCS-r; and ΔRFCS-f and mRFCS-XbaI (SEQ ID Nos:49 and 50, and 51 and 52, respectively). The primers used for PCR were designed so that the sequence identical to the fragment to be bound was located on the end bound to the fragment. The primers which include the positions corresponding to the 5' end and 3' end of the RFCS gene were designed to have additional sites of NdeI recognition site and XbaI recognition site, respectively. The two amplified DNA fragments were mixed and subjected to PCR again, obtaining the mature KOD-RFCS (KOD-mRFCS) gene from which the intervening sequence had been deleted and which had an XbaI recognition site at the 5' end and an NdeI recognition site at the 3' end. The construction procedure of the mature RFCS expression vector is shown in FIG. 22.

Example 3-4

Construction of Recombinant Expression Vectors for PCNA, RFCS and RFCL

Primers NdeI-PCNA and PCNA-XbaI (SEQ ID Nos:53 and 54) were designed to have additional sites of an NdeI recognition site and an XbaI recognition site at the 5' end and 3' end, respectively, of KOD-PCNA gene whose nucleotide sequence had been determined. Similarly, primers NdeI-RFCL and RFCL-XbaI (SEQ ID Nos:55 and 56) were designed to have additional sites of an NdeI recognition site and an XbaI recognition site at the 5' end and 3' end, respectively, of the KOD-RFCL gene. PCR was performed by using these primer pairs and a phage clone including the full length of each of these as a template, obtaining a KOD-PCNA gene and KOD-RFCL gene, both of which have an NdeI recognition site at the 5' end and an XbaI recognition site at the 3' end.

NdeI/NheI recognition sites of pET and the restriction enzyme recognition sites of these DNA fragments were used for subcloning, obtaining recombinant expression vectors (pET-PCNA, pET-mRFCS, pET-RFCL). The XbaI and NheI cut ends have compatible sites, enabling their ligation Subsequently, the nucleotide sequences of the inserted DNA fragments in plasmids pET-PCNA, pET-mRFCS and pET-RFCL were determined by the dideoxy chain termination method to confirm that there was no mutation resulting from PCR. The structure of the PCNA expression vector is shown in FIG. 23, and the structure of the mRFCS and RFCL expression vectors are shown in FIG. 24.

Example 3-5

Construction of mRFCS-RFCL Recombinant Coexpression Vector

PCR was performed by using pET-RFCL as a template and phosphorylated primers pET-f (SEQ ID NO:57) and RFCL-SpeI (SEQ ID NO:58). The obtained DNA fragments were cut with restriction enzyme SpeI, obtaining RFCL gene fragments having a T7 promoter/ribosome binding site upstream of the gene. PCR was performed by using pET-mRFCS as a template, NdeI-mRFCS (SEQ ID NO:49) and a phosphorylated primer mRFCS-XbaI (SEQ ID NO:52). The obtained DNA fragments were cut with the restriction enzyme NdeI, obtaining RFCS gene fragments. The NdeI/NheI recognition site of pET and the two gene fragments obtained was simultaneously ligated, obtaining a coexpression vector (pET-mRFCS-RFCL). SpeI and NheI cut ends have compatible sites, enabling their ligation.

Subsequently, the nucleotide sequences of the inserted DNA fragments in plasmid pET-mRFCS-RFCL were determined by the dideoxy chain termination method to confirm that there was no mutation resulting from PCR. The structure of the mRFCS-RFCL coexpression vector is shown in FIG. 25.

Example 3-6

Expression and Purification of KOD-PCNA

E. coli BL21 (DE3) was transformed with the recombinant expression vector pET-PCNA obtained in Example 3-4. The obtained transformant was cultured in LB medium (Molecular Cloning, p.A. 2,1989). The induction of the T7 promoter was carried out by adding isopropyl-β-D-thiogalactopyranoside 2 hours before the harvest. Cells were harvested from the culture medium by centrifugation. The cells were resuspended in a buffer solution, and then pressure-disrupted, obtaining a cell extract. The extract of cell disruption was heated at 80° C. for 30 minutes to insolubilize unpurified proteins derived from the host cell. After the insoluble fraction was removed by centrifugation, the supernatant was applied to two columns of HiTrapQ Cr. and Superdex 200 Cr., obtaining a purified PCAN sample derived from KOD1. The PCNA purification procedure is shown in FIG. 26(A), and the SDS-PAGE patterns of KOD and PCNA are shown in FIG. 26(B).

After the obtained purified sample was subjected to SDS-PAGE and transferred to a PVDF film, desired sites were cut out from the film and the N end sequences of the samples were determined by a protein sequencer. The result of sequencing was P-F-E-V-V, showing consistency with M-P-F-E-V-V which was presumed from the nucleotide sequence of the gene. Results are shown in Table 5 below.

TABLE 5

Determination of N end sequence of KOD accessory protein

| | Presumption from DNA | Peptide sequence |
|---|---|---|
| PCNA | M-P-F-E-V-V | P-F-E-V-V |
| RFCL | M-T-E-V-P-W | M-T-E-V-P |
| RFCS | M-S-E-E-V-K | S-E-E-V-K |

Example 3-7

Expression of KOD-mRFCS and KOD-RFCL

E. coli BL21 (DE3) was transformed with the recombinant expression vectors pET-mRFCS and pET-RFCL obtained in Example 3-4. The obtained transformant was cultured in LB medium. The induction of the T7 promoter was carried out by adding isopropyl-β-D-thiogalactopyranoside 2 hours before the harvest. Cells were harvested from the culture medium by centrifugation. The cells were resuspended in a buffer solution, and then ultrasonically disrupted, obtaining a cell extract. The extract of cell disruption was heated at 80° C. for 30 minutes to insolubilize unpurified proteins derived from the host cell. The insoluble fraction was removed by centrifugation, obtaining crudely purified samples of RFCL and RFCS.

Example 3-8

Expression and Purification of KOD-RFC Complex (mRFCS-RFCL)

E. coli BL21 (DE3) was transformed with using the recombinant expression vector pET-mRFCS-RFCL obtained in Example 3-5. The obtained transformant was cultured in LB medium. The induction of the T7 promoter was carried out by adding isopropyl-β-D-thiogalactopyranoside 2 hours before the harvest. Cells were harvested from the culture medium by centrifugation. The cells were resuspended in a buffer solution, and then pressure-disrupted, obtaining a cell extract. The extract of cell disruption was heated at 80° C. for 30 minutes to insolubilize unpurified proteins derived from the host cell. The solution was then centrifuged and the supernatant of disrupted cell was collected. In addition, nucleic acids were removed with polyethyleneimine and the insoluble fraction was removed by centrifugation. The supernatant was applied to two columns (Hydroxyapatite Cr., HiTrapQ Cr.), obtaining a purified sample of RFC complex (mRFCS-RFCL) derived from KOD1. The purification procedure of the RFC complex is shown in FIG. 27(A), and the SDS-PAGE pattern of the RFC complex is shown in FIG. 27(B).

The obtained purified samples were subjected to SDS-PAGE and transferred to a PVDF film, and the desired sites of mRFCS and RFCL were cut out from the film. The N terminal sequences of the samples were determined by a protein sequencer. Sequencing results were as follows: mRFCS: S-E-E-V-K, and RFCL: M-T-E-V-P. These showed consistency with the sequences presumed from the nucleotide sequence of the gene, i.e., mRFCS: M-S-E-E-V-K, and RFCL: M-T-E-V-P-W. The results are shown in Table 5 above.

Example 3-9

Association Ratios of KOD-PCNA Complex and the KOD-RFC Complex

The association ratio of KOD-PCNA complex was presumed from its molecular weight per monomer presumed from KOD-PCNA gene and from the previously reported association ratio of Pfu-PCNA derived from hyperthermophilic bacteria Pyrococcus furiosus, the presumed value being 84.6 kD The association ratio of KOD-RFC complex was presumed from its molecular weight per monomer presumed from KOD-mRFCS and KOD-RFCL, and from the previously reported association ratio of Pfu-RFC complex derived from hyperthermophilic bacteria *Pyrococcus furiosus*, the presumed values being 206 kD.

A purified PCNA sample and a purified RFC sample were mixed, and the mixture was analyzed with TSKgel G3000SW (TOSOH CORPORATION), giving a chart shown in FIG. 28. Their molecular weights determined by comparison with standard samples were as follows: PCNA: 87.1 kD, RFC complex: 227.4 kD. These values are both similar to the values estimated from the genes. It is thus deduced that PCNA has a homotrimer structure; the RFC complex has a heteropentamer structure; and mRFCS and RFCL are associated at a ratio of 1:4 in the RFC complex. The results are shown Table 6 below.

TABLE 6

Association conditions deduced from the molecular weights of PCNA and RFC

|  |  | Monomer molecular weight deduced from gene | Number of associations in *P. furiosus* | Presumed value (kDa) | Measured value (kDa) |
| --- | --- | --- | --- | --- | --- |
| PCNA |  | 28.2 | 3 | 84.6 | 87.1 |
| RFC | L | 57.2 | 1 | 206 | 227.4 |
|  | S | 37.2 | 4 |  |  |

Example 3-10

Effect of KOD-PCNA Protein for DNA Polymerase 150 fmol of KOD DNA polymerase was reacted with 1.5 pmol of DNA obtained by annealing an M13 P7 primer (SEQ ID NO:59) to M13 mp18 DNA (circular single-stranded DNA) to determine processivity. 450 fmol, 1.5 pmol, 4.5 pmol and 15 pmol samples of KOD-PCNA obtained in Example 3-6 were added to reaction buffer solutions [20 mM Tris-HCl (pH 7.5 at 75° C.), 10 mM KCl, 6 mM $(NH_4)_2SO_4$, 2 mM $MgCl_2$, 0.1% Triton X-100, 10 μg/ml BSA]. The mixtures were reacted at 75° C. for varying times: 30 seconds, 60 seconds and 120 seconds, to investigate their degrees of elongation. In the course of the elongation reaction DNA samples were withdrawn at the above reaction times and added to the same quantity of a stop solution (60 mM EDTA, 60 μM NaOH, 0.1% BPB, 30% glycerol). The obtained DNA samples were separated by 1% alkaline agarose electrophoresis and analyzed to determine the sizes of the synthesized DNA. The electrophoresis patterns of the synthesized DNA are shown in FIG. 29.

The patterns of the samples with no PCNA added showed 1.2 kb elongation with a reaction time of 30 seconds, 2.5 kb elongation with a reaction time of 60 seconds, and 5 kb elongation with a reaction time of 120 seconds. The pattern showed no point at which the DNA polymerase and the substrate specifically dissociated. The processivity of KOD DNA polymerase is supposed to be 5 kb or more. In the state of the substrate being in excess, i.e., 1.5 pmol of the substrate DNA relative to 150 fmol of DNA polymerase, the elongation rate by KOD DNA polymerase was about 40 bases per second.

It was found that the addition of PCNA tended to increase the DNA elongation rate. The DNA elongation rate was highest, i.e., 120 bases per second, when PCNA was added in 30 times the molar amount of DNA polymerase. This value is about 3 times as high as that of the sample with no PCNA added.

It is thought that a signal was observed in the vicinity of 0.5-2 kb because part of the KOD DNA polymerase molecule was bound to PCNA and thus were unable to contribute to promoting DNA synthesis activation. It is thought that an excess PCNA, as much as several ten times the amount of KOD DNA polymerase, was necessary because PCNA is in annular form and thus is difficult to act on annular single stranded DNA. Accordingly, RFC, which is thought to participate in opening and closing of PCNA, was further added to the PCNA to conduct a similar investigation and confirm whether this low molecular weight signal would disappear.

Example 3-11

Effect for DNA Polymerase of the Copresence of KOD-PCNA Protein and KOD-RFC Complex KOD DNA polymerase reactions were conducted in a similar manner to Example 3-10 either in the presence of KOD-PCNA or in the copresence of KOD-PCNA and KOD-RFC by using an circular single stranded DNA, which was annealed with a primer, as a substrate. The results are shown in FIG. 30. As with the results of Example 3-10, when only PCNA was added, an increase in the DNA elongation rate was observed, and a signal was observed in the vicinity of 0.5-2 kb. In contrast, when RFC and PCNA together were added, the signal at about 0.5-2 kb was diminished. This is presumably because almost all the KOD DNA polymerase molecules were available to react with PCNA in the presence of the RFC complex. This suggests that the three kinds of proteins are working cooperatively. The electrophoresis patterns of the synthesized DNA are shown in FIG. 30.

As seen from FIG. 30, compared with the reaction using only KOD DNA polymerase, the DNA elongation rate was increased in the copresence of PCNA and RFC. The amount of synthesized DNA was more than twice as much in the copresence of both PCNA and RFC.

Example 3-12

Effect of KOD-PCNA Protein on PCR

The effect produced by the addition of KOD-PCNA protein on PCR amplification of a 3.6 kb DNA in a human μ-globin cluster was investigated. The PCR buffer supplied with KOD-Plus (TOYOBO CO.,LTD), 0.2 mM dNTPs and 0.3 μM of a pair of primers of SEQ ID Nos:60 and 61 were used. 1 U KOD DNA polymerase was used as a heat-resistant DNA polymerase, and genomic DNA derived from human cell line K562 was used as a template. This reaction mixture was subjected to PCR using GeneAmp2400 (PE Applied Biosystems) to investigate the difference in the PCR results caused by the presence or absence of PCNA. The PCR conditions were as follows: 1 preliminary reaction of 94° C. for 2 minutes; and then 35 cycles of 94° C. for 20 seconds, 60° C. for 30 seconds and 68° C. for 4 minutes. The electrophoresis patterns of the PCR products are shown in FIG. 31.

When no PCNA was added and 3 ng of the template DNA was used, slight amplification of the target DNA was observed within a smear. In contrast, amplification of the target DNA was more clearly observed by adding PCNA, despite the amount of the template being the same. When 30 fmol of PCNA was added to the reaction solution, amplification of the target DNA was observed with the addition of 1 ng of the template DNA. That is, PCR sensitivity was increased at least 3-fold by the addition of PCNA. The amount of PCNA at which the effect of the addition occurs is not limited to this concentration since it will vary depending on the kind of the enzyme used, target DNA, PCR buffer, etc.

Example 3-13

Effect of KOD-RFC Complex on PCR

The effect produced by the addition of the KOD-RFC complex was investigated with the same target DNA and reaction solution as in Example 3-12. The amount of RFC effective for PCR was investigate by using 1 ng of genomic DNA derived from human cell line K562 as a template.

The electrophoresis patterns of the PCR products are shown in FIG. 32. As seen from FIG. 32, amplification of the target DNA was not observed when no RFC was added, but it was observed when 750 fmol of RFC was added to the reaction solution. The amount of RFC at which the effect of the addition occurs is not limited to this concentration since it will vary depending on the kind of the enzyme used, target DNA, PCR buffer, etc.

Example 3-14

Effect of the Copresence of KOD-PCNA Protein and KOD-RFC Complex for PCR

The effect produced by the addition of KOD-PCNA protein and KOD-RFC complex was investigated with the same target DNA and reaction solution as in Example 3-12. 1 ng of genomic DNA derived from human cell line K562 was used as a template and their optimal ratios were investigated. The electrophoresis patterns of the PCR products are shown in FIG. 33. As seen from FIG. 33, when 10 fmol of PCNA alone was added to the reaction solution, amplification of the target DNA was barely observed together with a smear, but sufficient amplification was observed when 1.5 pmol of PFC was further added to this reaction solution.

The amount ratio of KOD-PCNA protein to the KOD-RFC complex at which the effect of the addition occurs is not limited to these concentration ratios since it will vary depending on the kind of the enzyme used, target DNA, PCR buffer, etc.

Example 3-15

Effect for the Copresence of KOD-PCNA Protein and the KOD-RFC Complex in PCR Using a Mixed-Type DNA Polymerase The effect produced by the combined use of KOD-PCNA protein and the KOD-RFC complex in PCR using a mixture of two kinds of DNA polymerases was investigated with the same target DNA and reaction solution as in Example 3-12 1 ng of genomic DNA derived from human cell line K562 was used as a template. KOD Dash DNA polymerase, which is a mixture of KOD DNA polymerase and KOD (exo-) DNA polymerase which has lost KOD 3'-5' exonuclease activity, was used as the mixed-type DNA polymerase.

The electrophoresis patterns of the PCR products are shown in FIG. 34. As seen from FIG. 34, when no PCNA or RFC was added, amplification of the target DNA was barely observed together with a smear. In contrast, amplification of the target DNA was made somewhat clearer by the addition of PCNA, and amplification of the target DNA was greatly clarified by the further addition of RFC. The amount ratio of KOD-PCNA protein to the KOD-RFC complex at which the effect of the addition occurs is not limited to these concentration ratios since it will vary depending on the kind of the enzyme used, target DNA, PCR buffer, etc.

INDUSTRIAL AVAILABILITY

By using the composition for enhancing synthesis of DNA of the invention, hitherto impossible target nucleic acid DNA syntheses become possible. In addition, not only simple DNA synthesis but also PCR success rate can be enhanced. By using the DNA polymerase-related factor of the invention, the DNA synthesis activity of a DNA polymerase can be enhanced. Therefore, these are suitable for use in DNA synthesis methods, DNA amplification methods, nucleotide sequencing methods, etc such as PCR.

BRIEF DESCRIPTION OF THE DRAWINGS

FIG. 21 shows a comparison between the RFCS amino acid sequences of Mth and KOD in Example 3-3.

SEQUENCE LISTING

Figure 1:
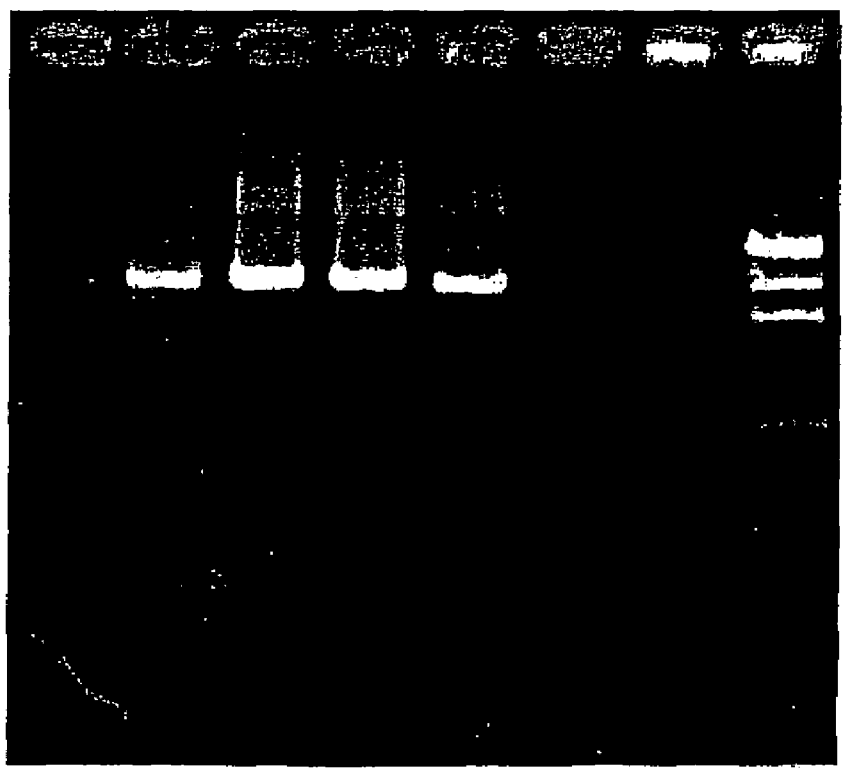
FIG. 1 shows the electrophoresis pattern of the PCR products obtained in Example 1-1.
Figure 2:
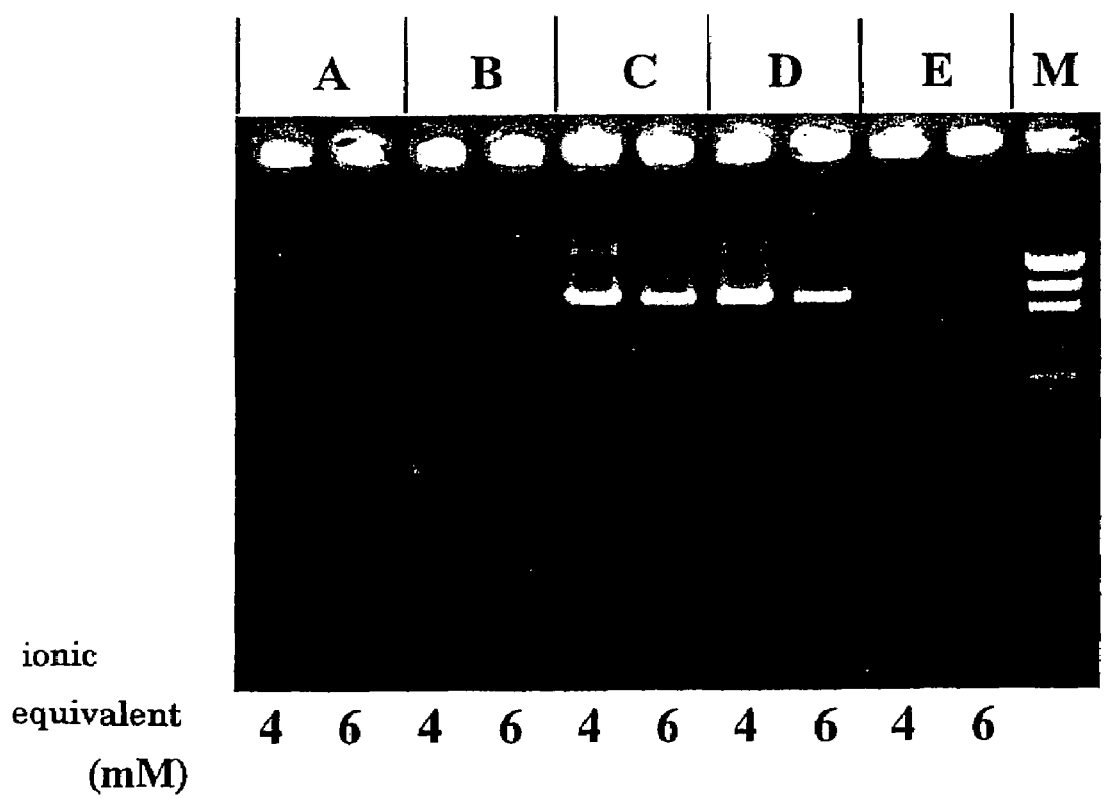
FIG. 2 shows the electrophoresis pattern of the PCR products obtained in Example 1-2.
Figure 3:
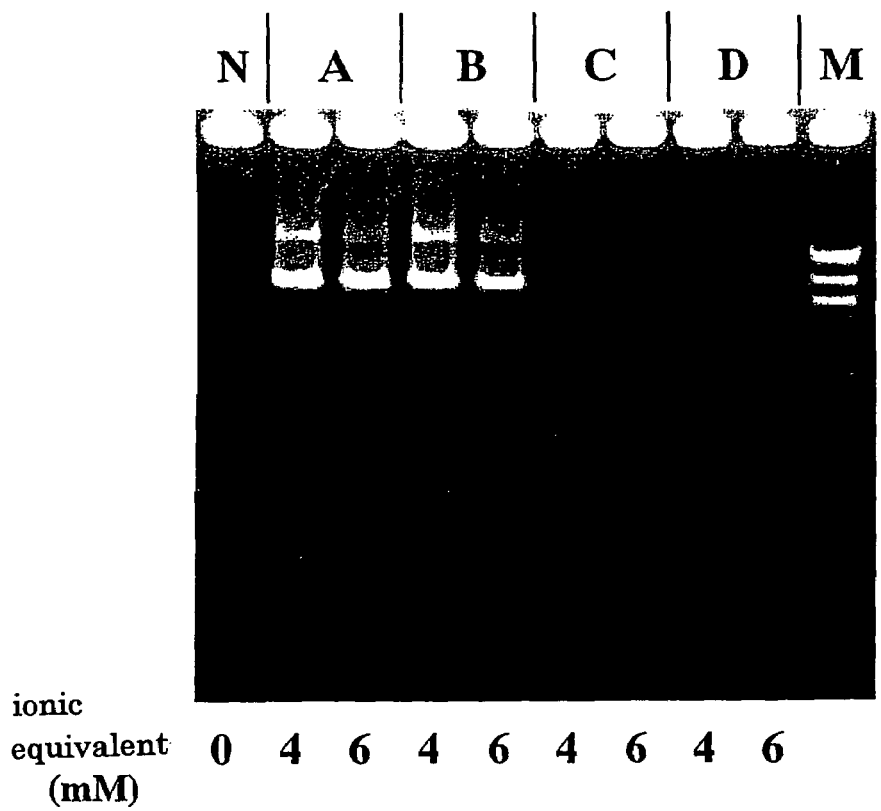
FIG. 3 shows the electrophoresis pattern of the PCR products obtained in Example 1-3.
Figure 4:
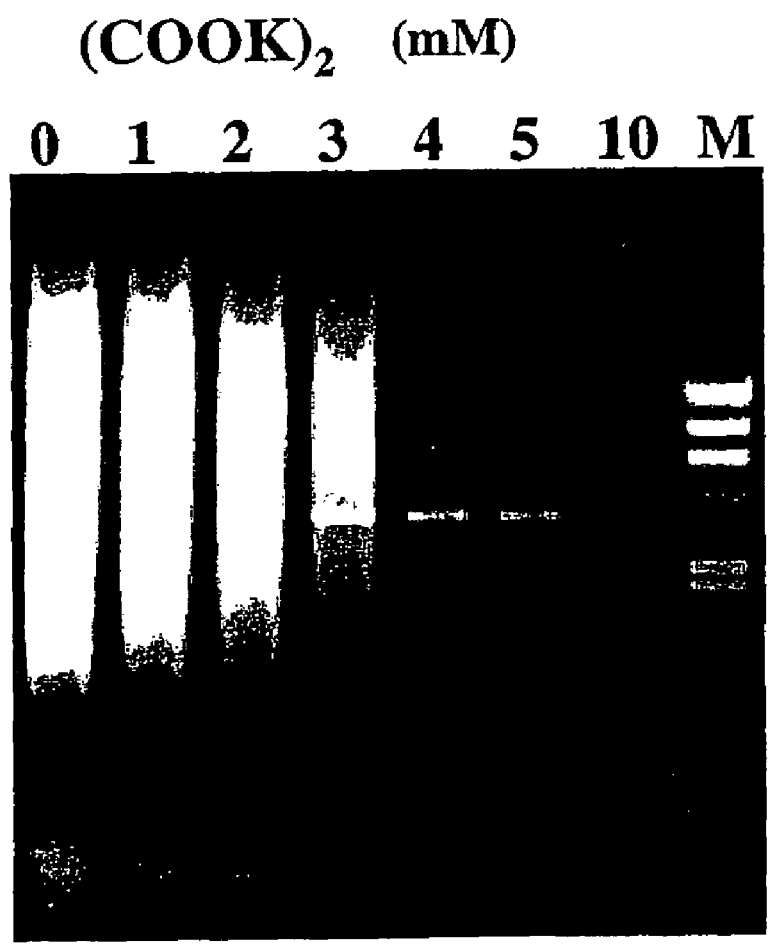
FIG. 4 shows the electrophoresis pattern of the PCR products obtained using a primer pair of SEQ ID NOs: 10 and 11 in Example 1-4.
Figure 5:
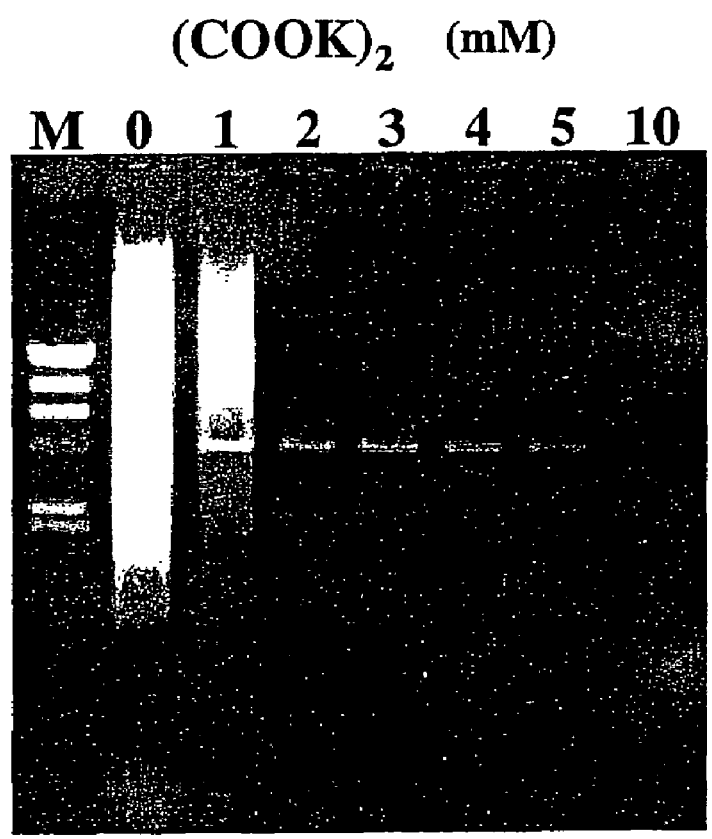
FIG. 5 shows the electrophoresis pattern of the PCR products obtained using a primer pair of SEQ ID NOs: 12 and 13 in Example 1-4.
Figure 6:
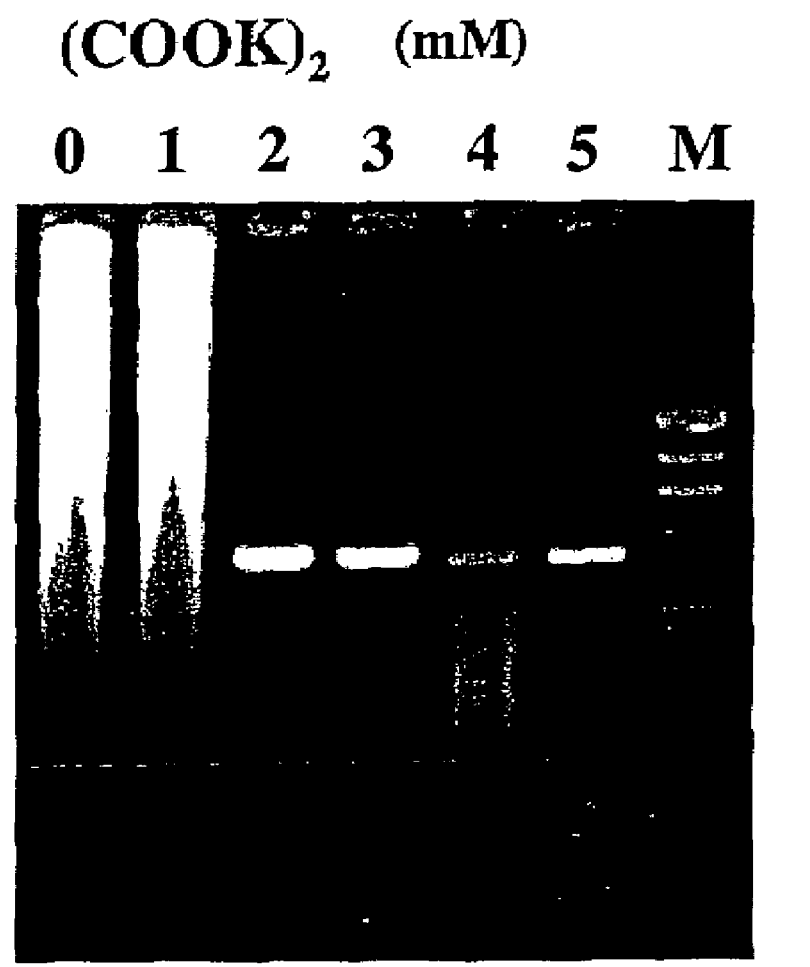
FIG. 6 shows the electrophoresis pattern of the PCR products obtained in Example 1-5.
Figure 7:
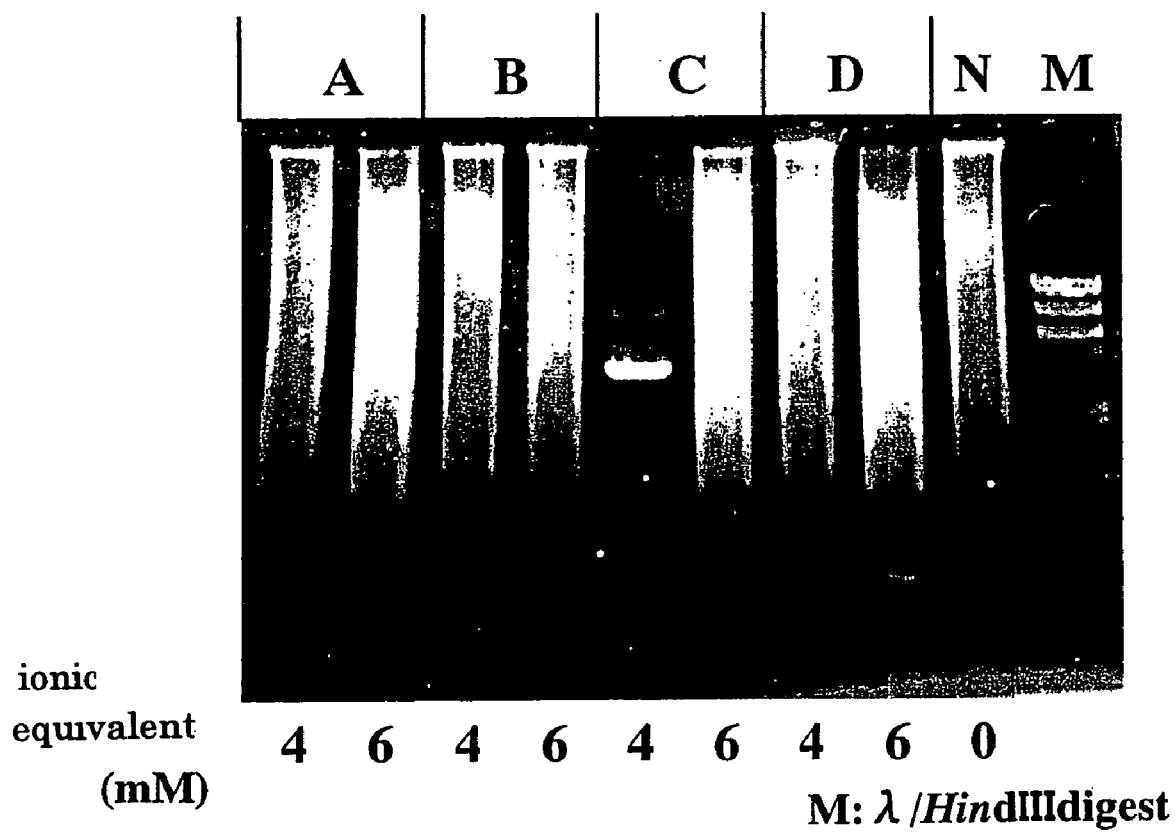
FIG. 7 shows the electrophoresis pattern of the PCR products obtained in Example 1-6.
Figure 8:
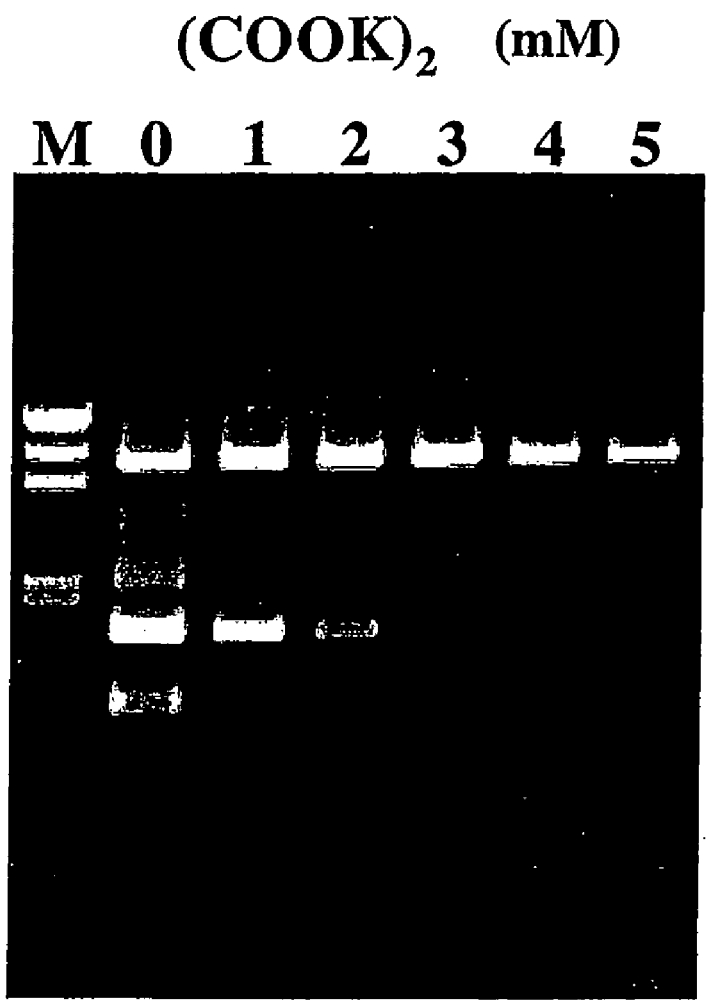
FIG. 8 shows the electrophoresis pattern of the PCR products obtained in Example 1-7.
Figure 9:
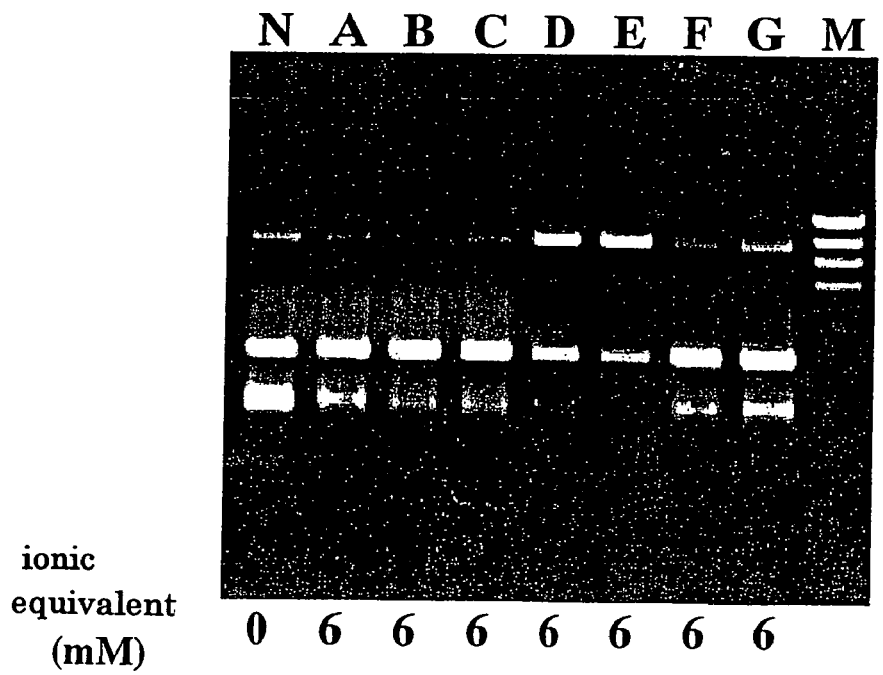
FIG. 9 shows the electrophoresis pattern of the PCR products obtained in Example 1-8.
Figure 10:
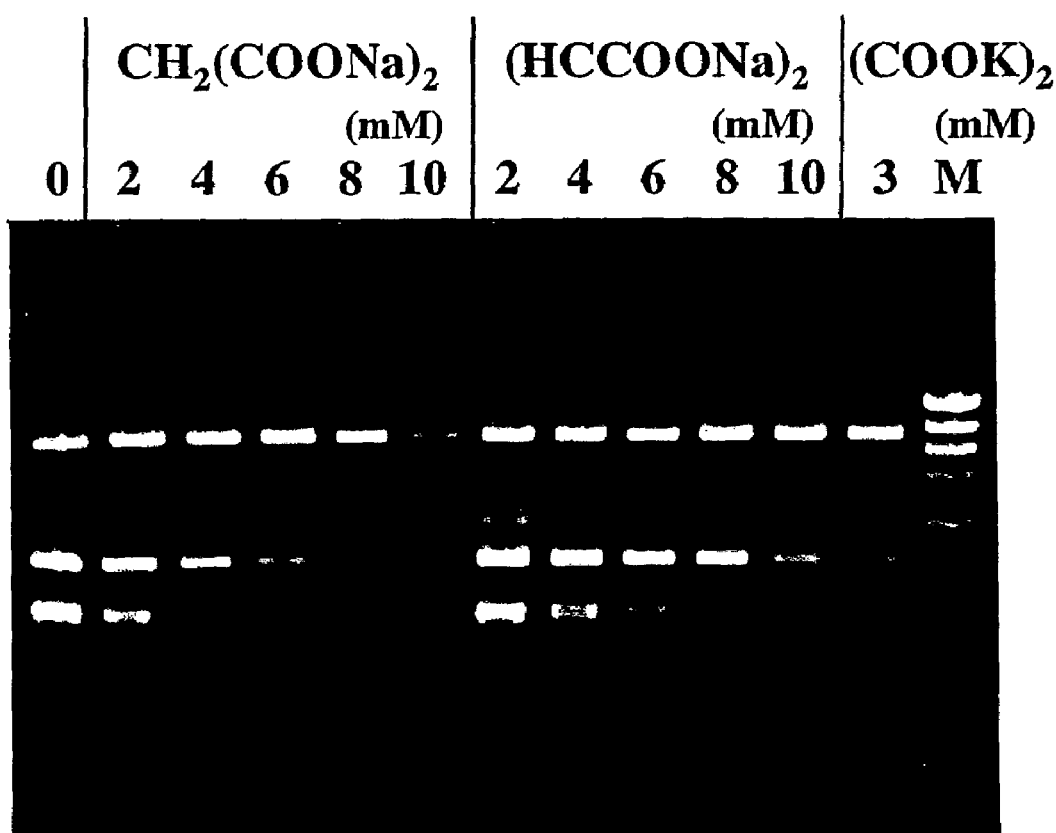
FIG. 10 shows the electrophoresis pattern of the PCR products obtained in Example 1-9.
Figure 11:
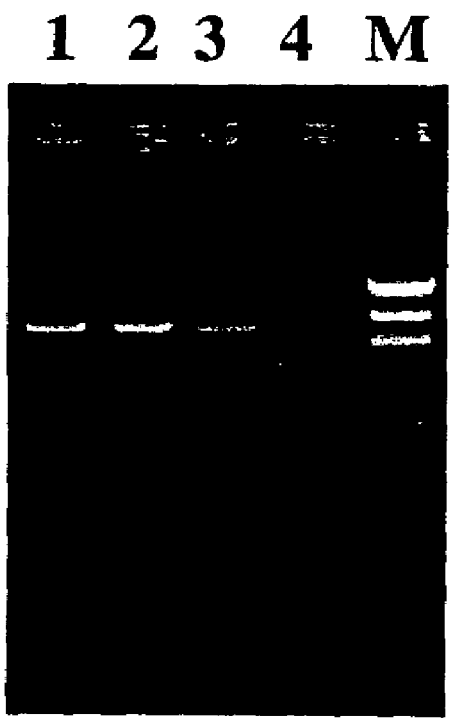
FIG. 11 shows the electrophoresis pattern of the PCR products obtained in Example 2-1.
Figure 12:
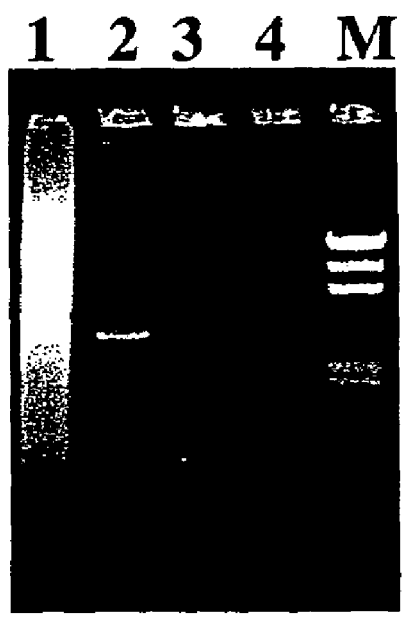
FIG. 12 shows the electrophoresis pattern of the PCR products obtained in Example 2-2.
Figure 13:
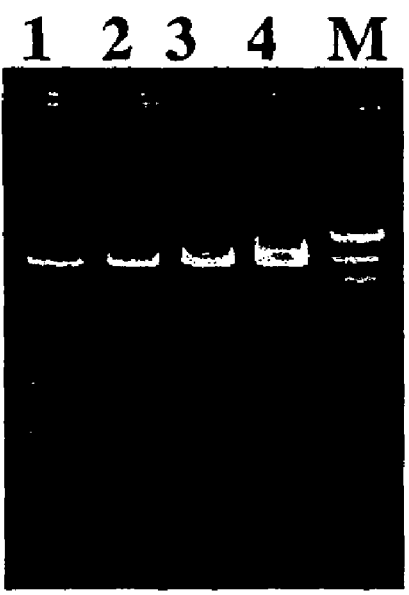
FIG. 13 shows the electrophoresis pattern of the PCR products obtained in Example 2-3.
Figure 14:
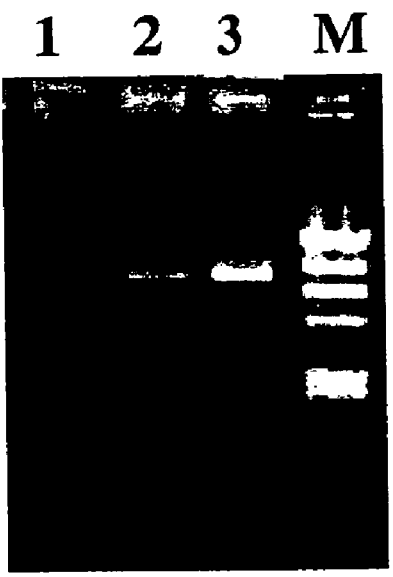
FIG. 14 shows the electrophoresis pattern of the PCR products obtained in Example 2-4.
Figure 15:
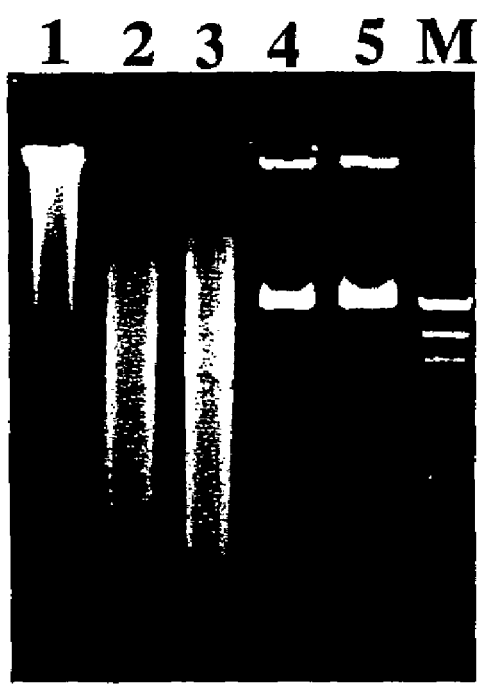
FIG. 15 shows the electrophoresis pattern of the PCR products obtained in Example 2-5.
Figure 16:
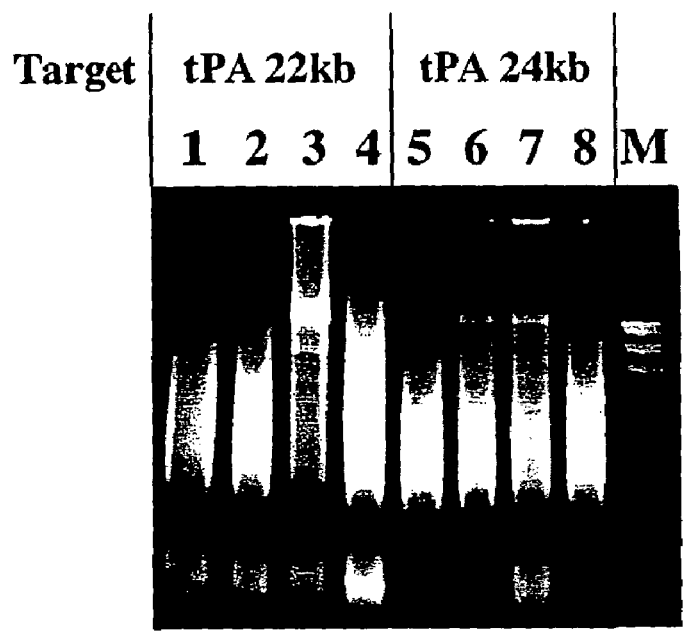
FIG. 16 shows the electrophoresis pattern of the PCR products obtained in Example 2-6.
Figure 17:
FIG. 17 shows the electrophoresis pattern of the PCR products obtained in Example 2-7.
Figure 18:
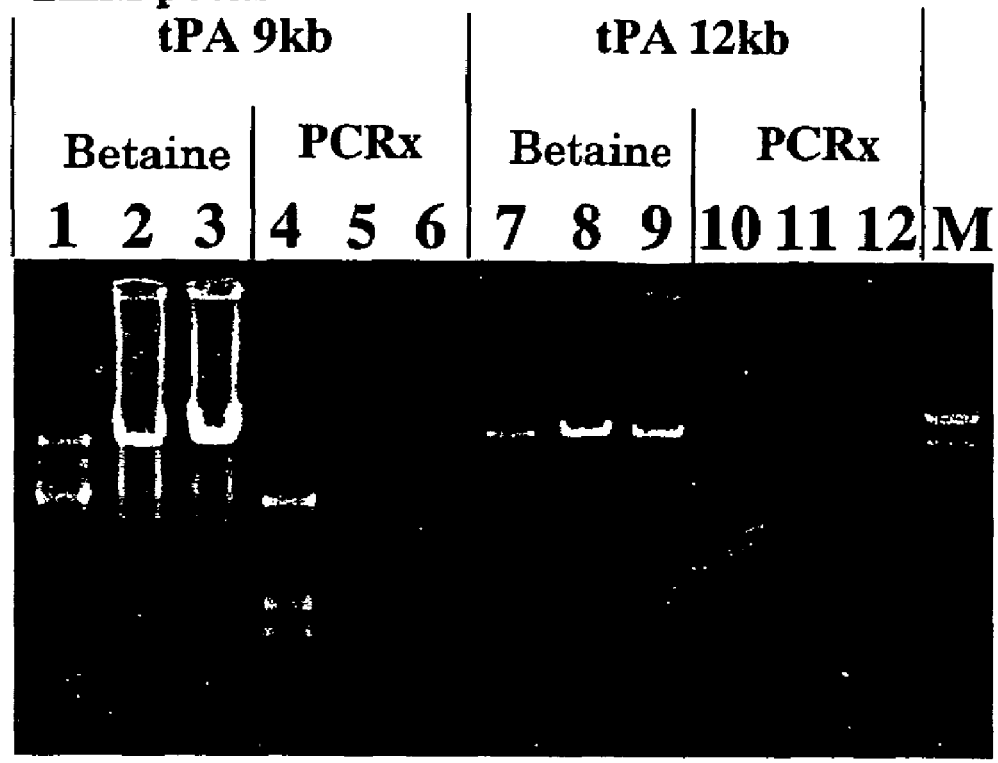
FIG. 18 shows the electrophoresis pattern of the PCR products obtained in Example 2-8.
Figure 19:
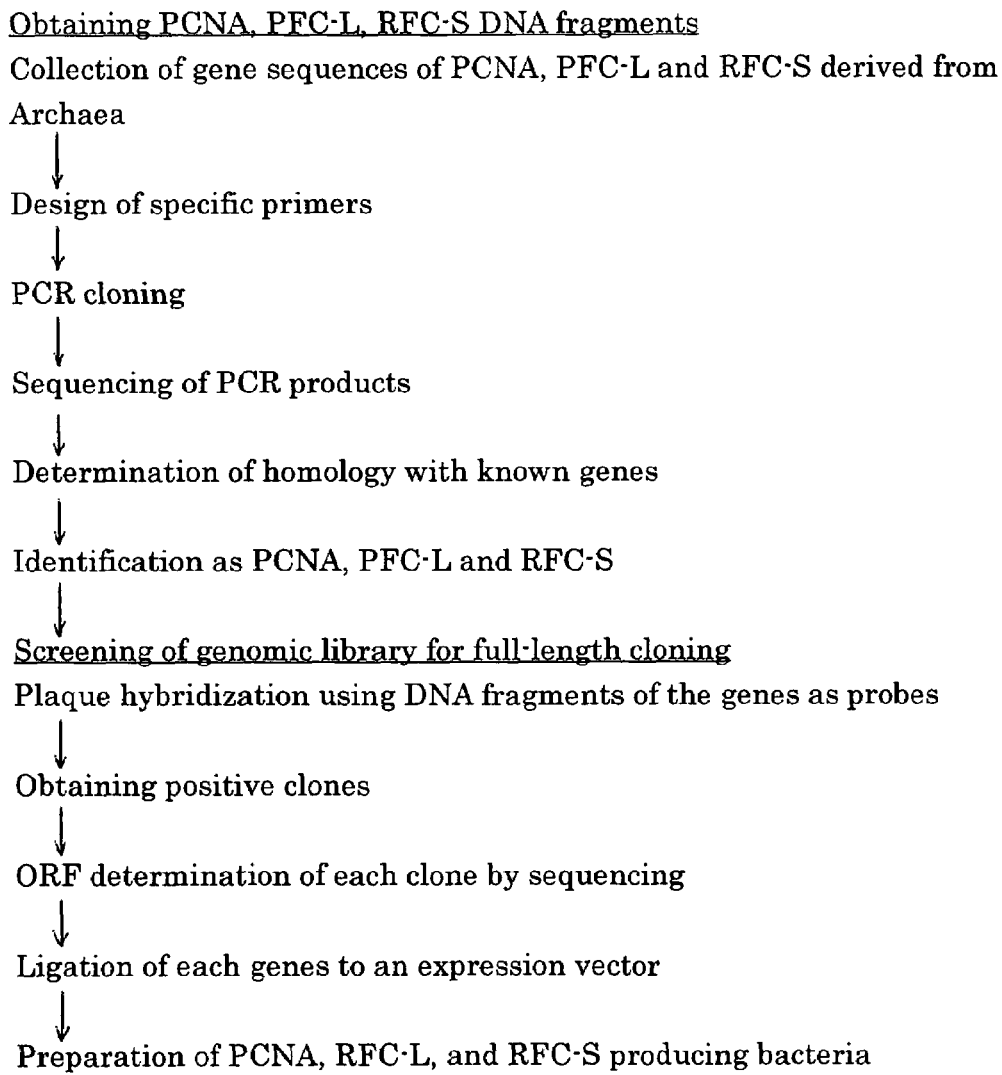
FIG. 19 shows the procedure for cloning the gene encoding the KOD1-derived DNA polymerase-related factor in Example 3-1.
Figure 20:
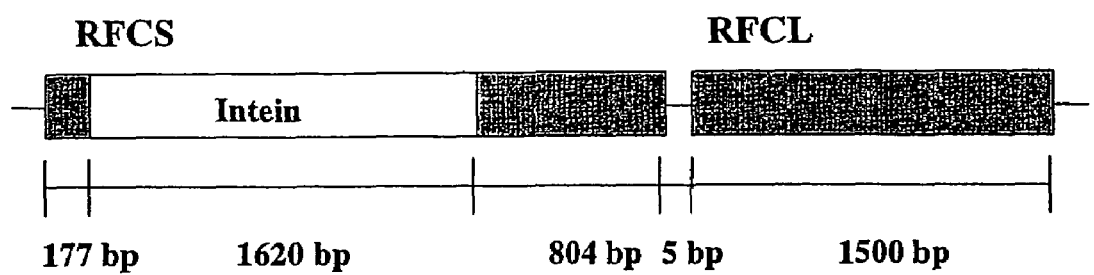
FIG. 20 shows the structure of the RFCS and RFCL genes used in Example 3-3.
Figure 22:
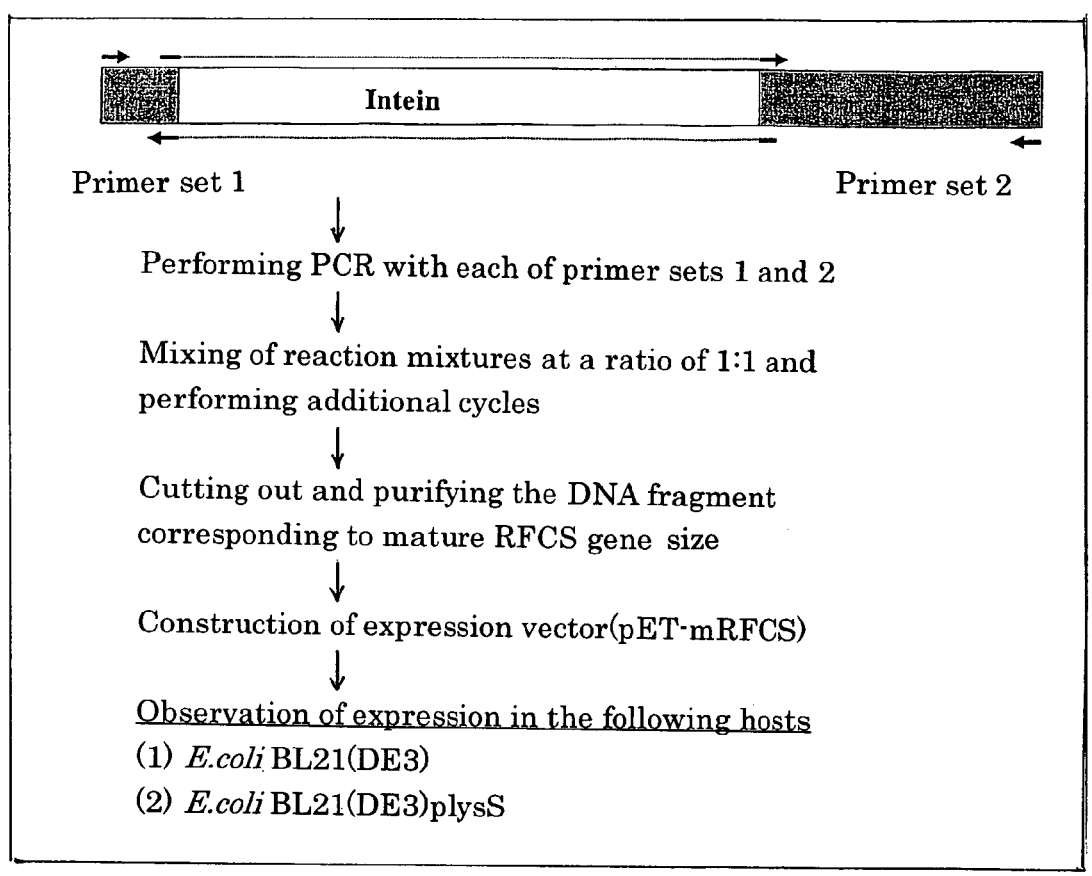
FIG. 22 shows the procedure for constructing the mature RFCS expression vector produced in Example 3-3.
Figure 23:
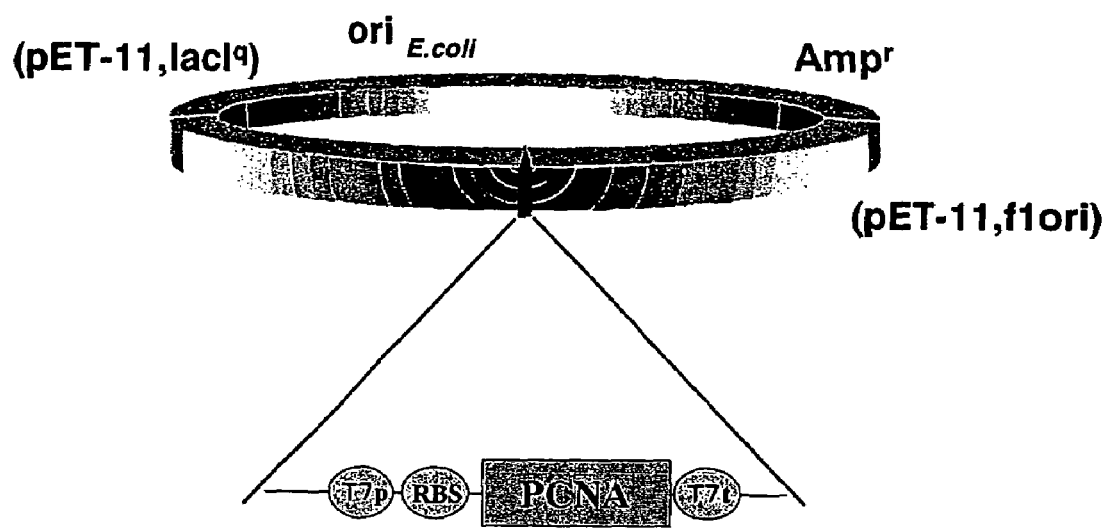
FIG. 23 shows the PCNA expression vector produced in Example 3-4.
Figure 24:
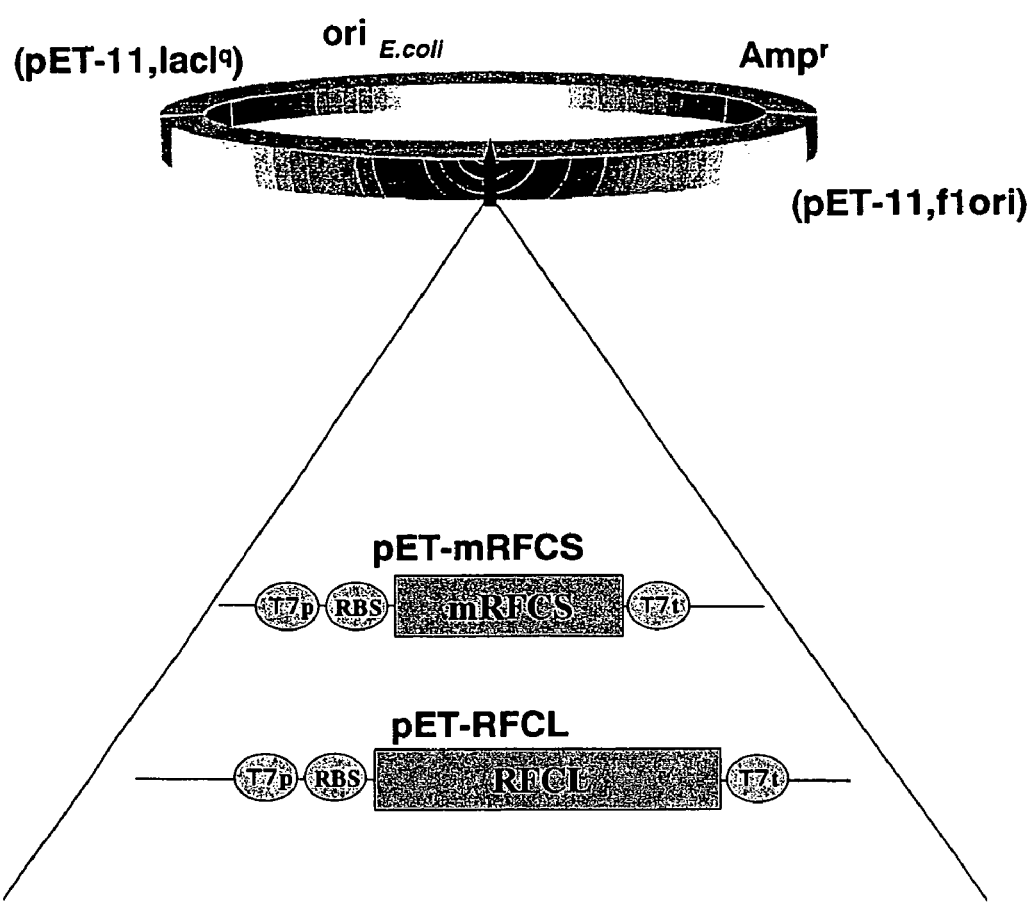
FIG. 24 shows the mRFCS and RFCL expression vectors produced in Example 3-4.
Figure 25:
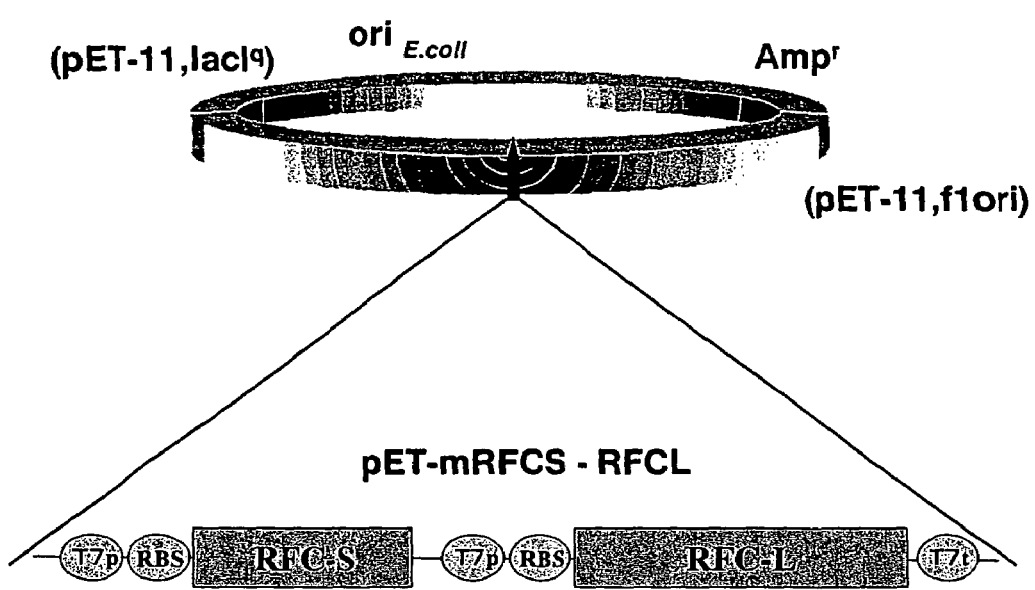
FIG. 25 shows the mRFCS-RFCL coexpression vector produced in Example 3-5.
Figure 26:
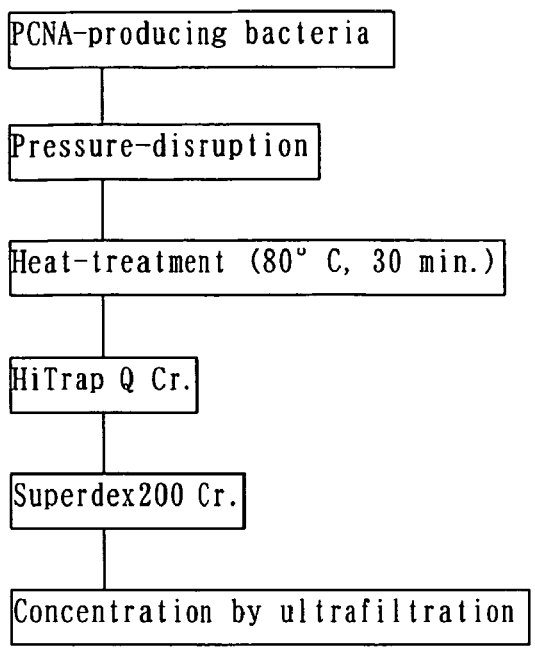
FIG. 26(A) shows the PCNA purification procedure performed in Example 3-6.
FIG. 26(B) shows the electrophoresis pattern showing the purity of the PCNA thus obtained.
Figure 26:
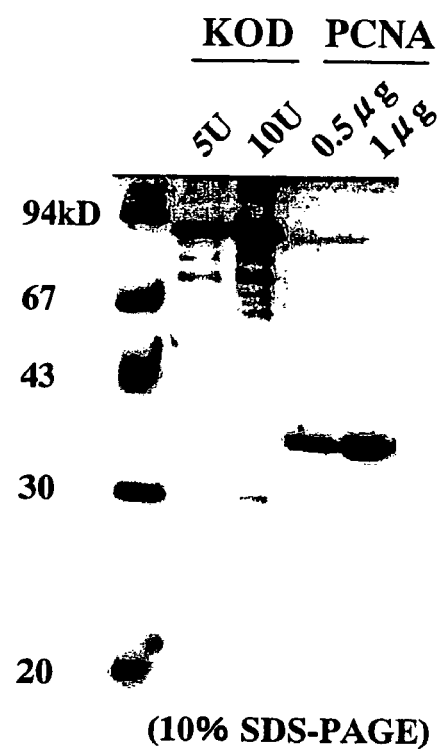
Figure 27:
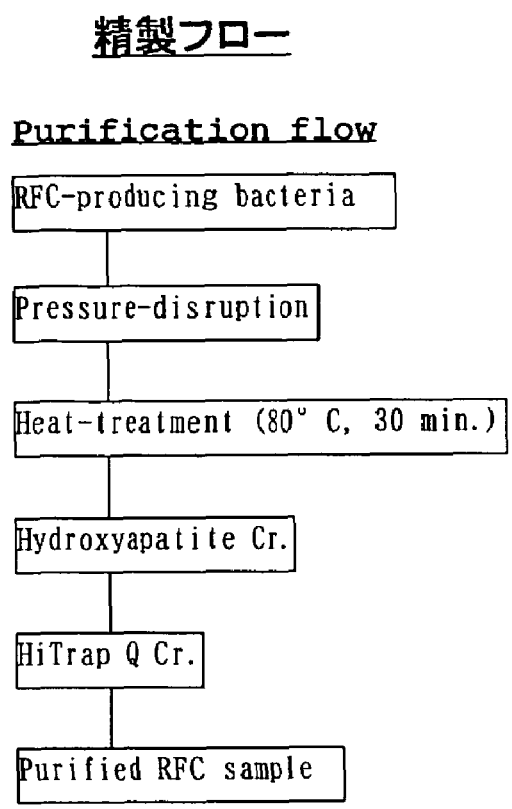
FIG. 27(A) shows the RFC purification procedure performed in Example 3-8.
FIG. 27(B) shows the electrophoresis pattern showing the purity of the RFC thus obtained.
Figure 27:
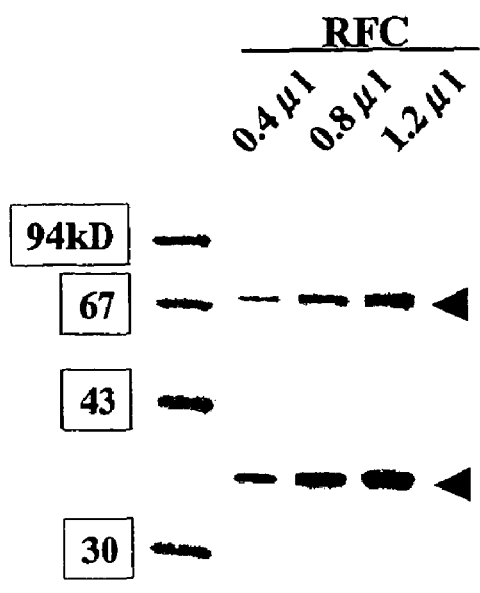
Figure 28:
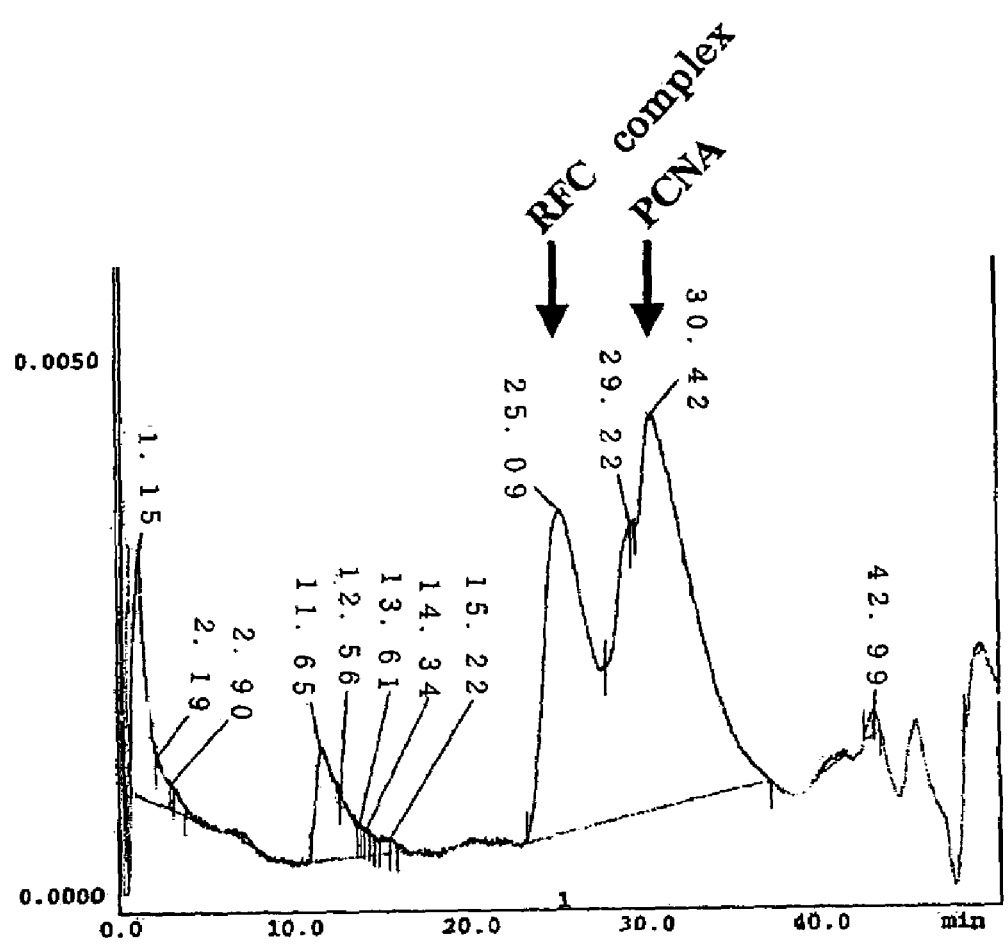
FIG. 28 shows the HPLC patterns of PCNA and RFC in Example 3-9.
Figure 29:
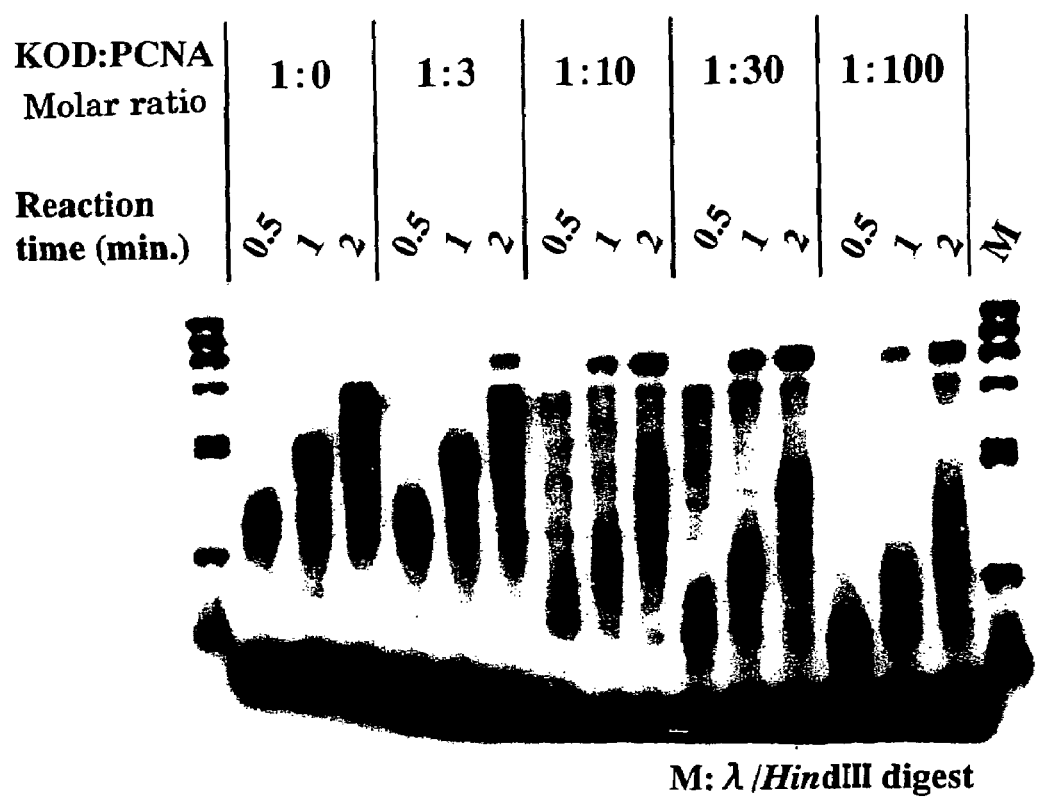
FIG. 29 shows the electrophoresis pattern of the DNAs obtained in Example 3-10.
Figure 30:
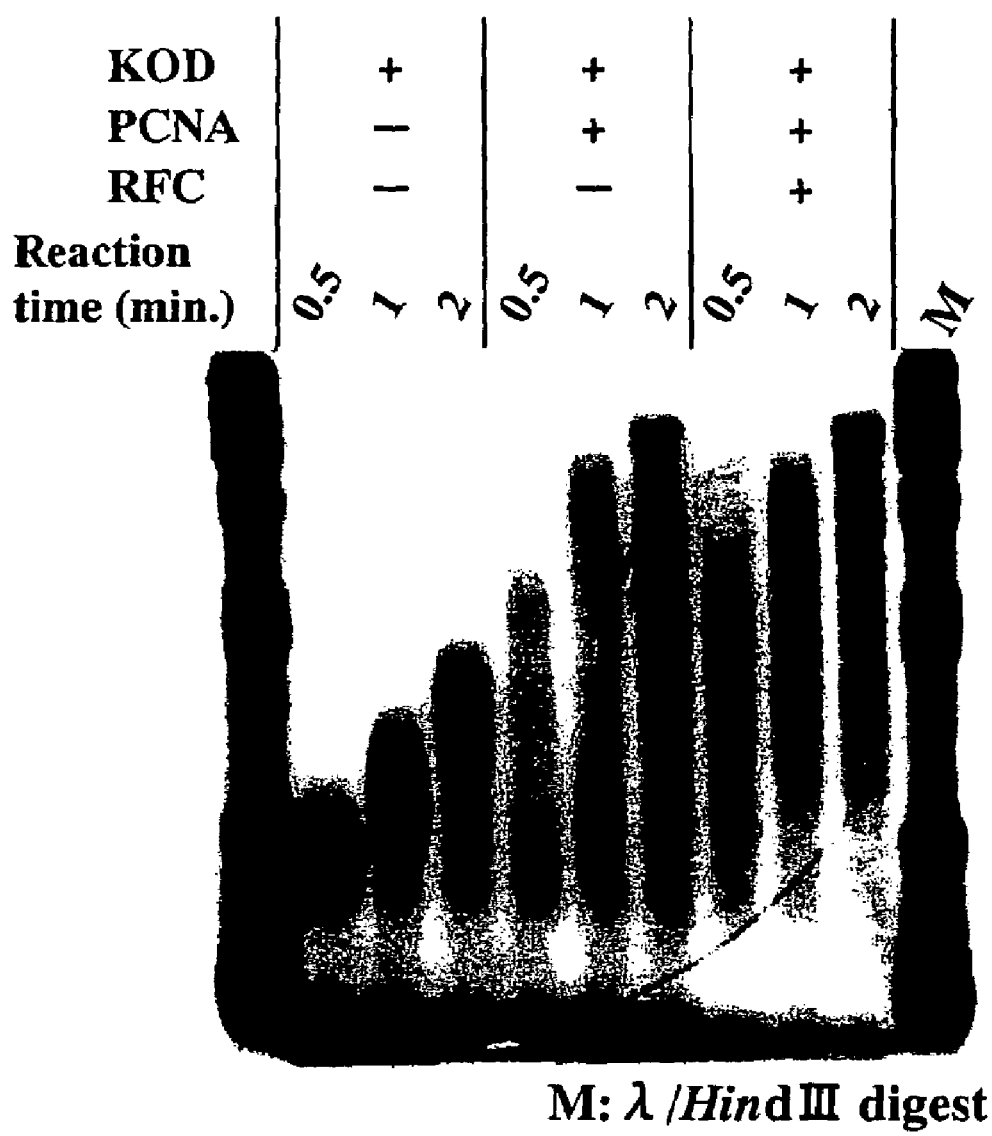
FIG. 30 shows the electrophoresis pattern of the DNAs obtained in Example 3-11.
Figure 31:
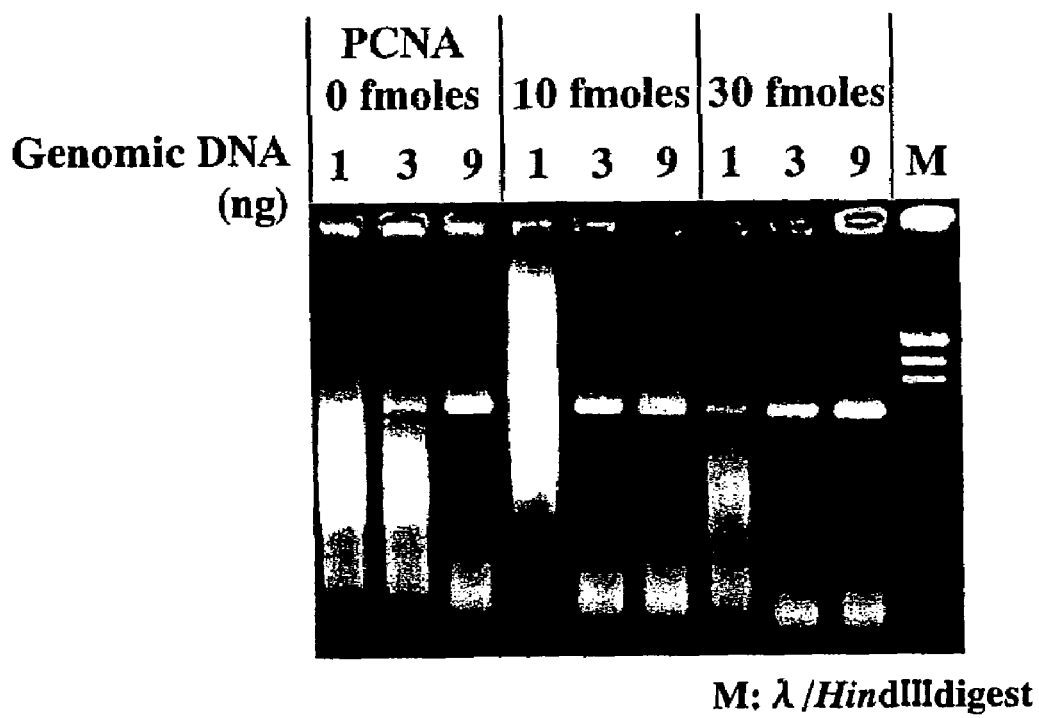
FIG. 31 shows the electrophoresis pattern of the PCR product obtained in Example 3-12.
Figure 32:
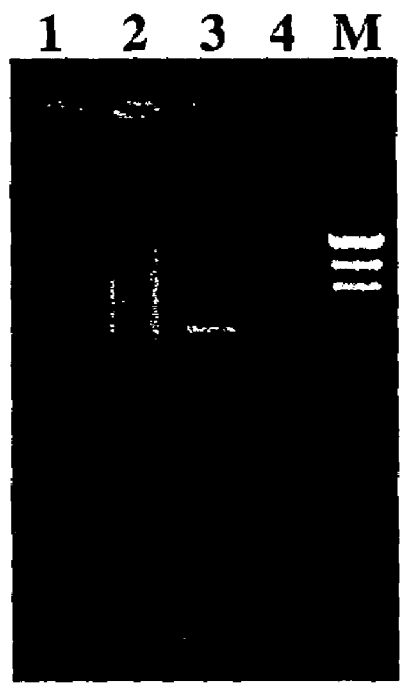
FIG. 32 shows the electrophoresis pattern of the PCR product obtained in Example 3-13.
Figure 33:
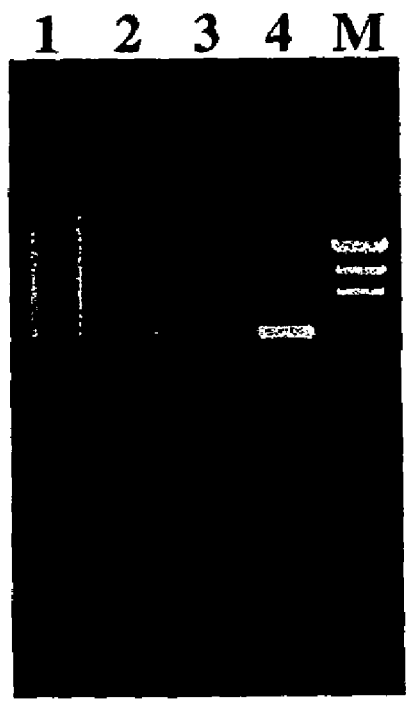
FIG. 33 shows the electrophoresis pattern of the PCR product obtained in Example 3-14.
Figure 34:
FIG. 34 shows the electrophoresis pattern of the PCR product obtained in Example 3-15.

```
<160> NUMBER OF SEQ ID NOS: 61

<210> SEQ ID NO 1
<211> LENGTH: 774
<212> TYPE: PRT
<213> ORGANISM: Thermococcus kodakaraensis KOD1
<220> FEATURE:
<223> OTHER INFORMATION: KOD DNA polymerase

<400> SEQUENCE: 1

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Glu Val Lys Lys Ile Thr Ala Glu Arg His Gly Thr Val Val Thr
    50                  55                  60

Val Lys Arg Val Glu Lys Val Gln Lys Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Ile Asp Ile Tyr Glu Tyr
            100                 105                 110

Asp Ile Pro Phe Ala Lys Arg Tyr Leu Ile Asp Lys Gly Leu Val Pro
        115                 120                 125

Met Glu Gly Asp Glu Glu Leu Lys Met Leu Ala Phe Asp Ile Glu Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Leu Gly Ile Asn Phe Ala Leu Gly Arg Asp Gly Ser Glu Pro Lys
225                 230                 235                 240
```

```
Ile Gln Arg Met Gly Asp Arg Phe Ala Val Glu Val Lys Gly Arg Ile
                245                 250                 255
His Phe Asp Leu Tyr Pro Val Ile Arg Arg Thr Ile Asn Leu Pro Thr
            260                 265                 270
Tyr Thr Leu Glu Ala Val Tyr Glu Ala Val Phe Gly Gln Pro Lys Glu
        275                 280                 285
Lys Val Tyr Ala Glu Glu Ile Thr Thr Ala Trp Glu Thr Gly Glu Asn
    290                 295                 300
Leu Glu Arg Val Ala Arg Tyr Ser Met Glu Asp Ala Lys Val Thr Tyr
305                 310                 315                 320
Glu Leu Gly Lys Glu Phe Leu Pro Met Glu Ala Gln Leu Ser Arg Leu
                325                 330                 335
Ile Gly Gln Ser Leu Trp Asp Val Ser Arg Ser Thr Gly Asn Leu
            340                 345                 350
Val Glu Trp Phe Leu Leu Arg Lys Ala Tyr Glu Arg Asn Glu Leu Ala
            355                 360                 365
Pro Asn Lys Pro Asp Glu Lys Glu Leu Ala Arg Arg Gln Ser Tyr
        370                 375                 380
Glu Gly Gly Tyr Val Lys Glu Pro Glu Arg Gly Leu Trp Glu Asn Ile
385                 390                 395                 400
Val Tyr Leu Asp Phe Arg Ser Leu Tyr Pro Ser Ile Ile Thr His
                405                 410                 415
Asn Val Ser Pro Asp Thr Leu Asn Arg Glu Gly Cys Lys Glu Tyr Asp
            420                 425                 430
Val Ala Pro Gln Val Gly His Arg Phe Cys Lys Asp Phe Pro Gly Phe
        435                 440                 445
Ile Pro Ser Leu Leu Gly Asp Leu Leu Glu Glu Arg Gln Lys Ile Lys
    450                 455                 460
Lys Lys Met Lys Ala Thr Ile Asp Pro Ile Glu Arg Lys Leu Leu Asp
465                 470                 475                 480
Tyr Arg Gln Arg Ala Ile Lys Ile Leu Ala Asn Ser Tyr Tyr Gly Tyr
                485                 490                 495
Tyr Gly Tyr Ala Arg Ala Arg Trp Tyr Cys Lys Glu Cys Ala Glu Ser
            500                 505                 510
Val Thr Ala Trp Gly Arg Glu Tyr Ile Thr Met Thr Ile Lys Glu Ile
        515                 520                 525
Glu Glu Lys Tyr Gly Phe Lys Val Ile Tyr Ser Asp Thr Asp Gly Phe
    530                 535                 540
Phe Ala Thr Ile Pro Gly Ala Asp Ala Glu Thr Val Lys Lys Lys Ala
545                 550                 555                 560
Met Glu Phe Leu Lys Tyr Ile Asn Ala Lys Leu Pro Gly Ala Leu Glu
                565                 570                 575
Leu Glu Tyr Glu Gly Phe Tyr Lys Arg Gly Phe Phe Val Thr Lys Lys
            580                 585                 590
Lys Tyr Ala Val Ile Asp Glu Glu Gly Lys Ile Thr Thr Arg Gly Leu
        595                 600                 605
Glu Ile Val Arg Arg Asp Trp Ser Glu Ile Ala Lys Glu Thr Gln Ala
    610                 615                 620
Arg Val Leu Glu Ala Leu Leu Lys Asp Gly Asp Val Glu Lys Ala Val
625                 630                 635                 640
Arg Ile Val Lys Glu Val Thr Glu Lys Leu Ser Lys Tyr Glu Val Pro
                645                 650                 655
```

Pro Glu Lys Leu Val Ile His Glu Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Ser Ala Trp
        755                 760                 765

Leu Lys Pro Lys Gly Thr
    770

<210> SEQ ID NO 2
<211> LENGTH: 249
<212> TYPE: PRT
<213> ORGANISM: Thermococcus kodakaraensis KOD1
<220> FEATURE:
<223> OTHER INFORMATION: KOD-PCNA

<400> SEQUENCE: 2

Met Pro Phe Glu Val Val Phe Asp Gly Ala Lys Glu Phe Ala Asp Leu
1               5                   10                  15

Ile Ala Thr Ala Ser Asn Leu Ile Asp Glu Ala Ala Phe Lys Phe Thr
            20                  25                  30

Glu Glu Gly Ile Ser Met Arg Ala Met Asp Pro Ser Arg Val Val Leu
        35                  40                  45

Ile Asp Leu Asn Leu Pro Glu Ser Ile Phe Ser Lys Tyr Glu Val Glu
    50                  55                  60

Glu Pro Glu Thr Ile Gly Ile Asn Met Asp Gln Phe Lys Lys Ile Leu
65                  70                  75                  80

Lys Arg Gly Lys Ala Lys Asp Thr Leu Ile Leu Arg Lys Gly Asp Glu
                85                  90                  95

Asn Phe Leu Glu Ile Thr Phe Glu Gly Thr Ala Lys Arg Thr Phe Arg
            100                 105                 110

Leu Pro Leu Ile Asp Val Glu Glu Leu Glu Leu Glu Leu Pro Glu Leu
        115                 120                 125

Pro Phe Thr Ala Lys Val Val Leu Leu Gly Glu Val Leu Lys Glu Gly
    130                 135                 140

Ile Lys Asp Ala Ser Leu Val Ser Asp Ala Ile Lys Phe Ile Ala Lys
145                 150                 155                 160

Glu Asn Glu Phe Thr Met Lys Ala Glu Gly Glu Thr Asn Glu Val Glu
                165                 170                 175

Ile Arg Leu Thr Leu Glu Asp Glu Gly Leu Leu Asp Leu Glu Val Glu
            180                 185                 190

Glu Glu Thr Lys Ser Ala Tyr Gly Ile Ser Tyr Leu Ser Asp Met Val
        195                 200                 205

Lys Gly Ile Gly Lys Ala Asp Glu Val Ile Leu Arg Phe Gly Asn Glu
    210                 215                 220

Met Pro Leu Gln Met Glu Tyr Met Ile Arg Asp Glu Gly Arg Leu Thr
225                 230                 235                 240

```
<210> SEQ ID NO 3
<211> LENGTH: 750
<212> TYPE: DNA
<213> ORGANISM: Thermococcus kodakaraensis KOD1
<220> FEATURE:
<223> OTHER INFORMATION: KOD-PCNA

<400> SEQUENCE: 3
atgccgttcg aagttgtttt tgacggggcc aaggagtttg cagacctgat agcgaccgca      60
agcaacctca tcgacgaggc cgcctttaag ttcactgagg aaggcataag catgcgcgca     120
atggacccga gcagggtcgt tctcattgac ctcaacctgc ccgaaagcat cttctccaag     180
tacgaggtcg aagagcccga caatcggca tcaacatgg accagttcaa gaaaatcctc      240
aagcgcggca aggcgaaaga cacctcata ctcaggaagg cgacgagaa cttccttgag      300 ataacttttg agggaaccgc caagaggaca ttcaggctcc ctctgataga gtgtggaagag    360 cttgagctgg agcttcccga gctcccgttc acggctaagg tagtcctcct cggtgaggtt    420
ctcaaggagg gcataaagga cgcttccctc gtcagcgacg ccatcaagtt catagcaaag    480
gagaacgagt tcacaatgaa ggccgagggc gagaccaacg aggtcgagat aaggcttacc    540
cttgaggacg agggccttct cgaccttgaa gtcgaggaag agaccaagag tgcctacggc    600
ataagctacc tcagcgacat ggtcaagggc atcggaagg ccgacgaagt tatcctccgc      660
ttcggcaacg agatgccgct ccagatggag tacatgatca gagacgaggg cagactgacc    720
ttcctgctcg ctccgcgcgt tgaggagtga                                       750

<210> SEQ ID NO 4
<211> LENGTH: 326
<212> TYPE: PRT
<213> ORGANISM: Thermococcus kodakaraensis KOD1
<220> FEATURE:
<223> OTHER INFORMATION: KOD-RFCS

<400> SEQUENCE: 4

Met Ser Glu Glu Val Lys Glu Val Lys Ile Leu Glu Lys Pro Trp Val
1               5                   10                  15

Glu Lys Tyr Arg Pro Gln Arg Leu Glu Asp Ile Val Gly Gln Asp His
            20                  25                  30

Ile Val Lys Arg Leu Lys His Tyr Val Lys Thr Gly Ser Met Pro His
        35                  40                  45

Leu Leu Phe Ala Gly Pro Pro Gly Val Gly Lys Thr Thr Ala Ala Leu
    50                  55                  60

Ala Leu Ala Arg Glu Leu Phe Gly Glu Asn Trp Arg His Asn Phe Leu
65                  70                  75                  80

Glu Leu Asn Ala Ser Asp Glu Arg Gly Ile Asn Val Ile Arg Glu Lys
                85                  90                  95

Val Lys Glu Phe Ala Arg Thr Lys Pro Ile Gly Gly Ala Ser Phe Lys
            100                 105                 110

Ile Ile Phe Leu Asp Glu Ala Asp Ala Leu Thr Gln Asp Ala Gln Gln
        115                 120                 125

Ala Leu Arg Arg Thr Met Glu Met Phe Ser Asn Asn Val Arg Phe Ile
    130                 135                 140

Leu Ser Cys Asn Tyr Ser Ser Lys Ile Ile Glu Pro Ile Gln Ser Arg
145                 150                 155                 160
```

Phe Leu Leu Ala Pro Arg Val Glu Glu
            245

```
Cys Ala Ile Phe Arg Phe Arg Pro Leu Arg Asp Glu Asp Ile Ala Lys
                165                 170                 175
Arg Ile Arg Tyr Ile Ala Glu Asn Glu Gly Leu Glu Leu Thr Glu Glu
            180                 185                 190
Gly Leu Gln Ala Ile Leu Tyr Val Ala Glu Gly Asp Leu Arg Arg Ala
        195                 200                 205
Ile Asn Val Leu Gln Ala Ala Ala Leu Asp Thr Lys Ile Thr Asp
210                 215                 220
Glu Asn Val Phe Leu Val Ala Ser Arg Ala Arg Pro Glu Asp Val Arg
225                 230                 235                 240
Glu Met Met Thr Leu Ala Leu Glu Gly Asn Phe Leu Lys Ala Arg Glu
                245                 250                 255
Lys Leu Arg Asp Ile Leu Leu Arg Gln Gly Leu Ser Gly Glu Asp Val
            260                 265                 270
Leu Ile Gln Met His Lys Glu Val Phe Asn Leu Pro Ile Pro Glu Asp
        275                 280                 285
Lys Lys Val Ala Leu Ala Asp Lys Ile Gly Glu Tyr Asn Phe Arg Leu
    290                 295                 300
Val Glu Gly Ala Asn Glu Met Ile Gln Leu Glu Ala Leu Leu Ala Gln
305                 310                 315                 320
Phe Thr Ile Met Gly Lys
                325

<210> SEQ ID NO 5
<211> LENGTH: 981
<212> TYPE: DNA
<213> ORGANISM: Thermococcus kodakaraensis KOD1
<220> FEATURE:
<223> OTHER INFORMATION: KOD-RFCS

<400> SEQUENCE: 5
atgtccgagg aagtgaagga agttaaaatt ctcgaaaagc cgtgggtcga agtacaga      60
ccccagaggc tcgaggacat agtaggtcag gatcacatag tcaagaggct gaagcactac   120
gttaaaaccg ctcgatgcc gcaccttcta ttcgcagggc cacccggcgt cgggaagaca   180
accgctgcac tggctttagc tagagaactc ttcggtgaga actggaggca caacttccta   240
gagctgaacg cgagcgatga gaggggtata aacgtcatcc gtgaaaaggt aaaggagttc   300
gcgaggacga agccgatagg cggtgcgagc tttaagataa tcttccttga tgaggcagat   360
gccctcacac aggacgctca gcaggccctc agaaggacga tggagatgtt ctcgaacaac   420
gtccgcttta tcctgagctg taactactcc tcaaagatca tcgaacccat acagtcgagg   480
tgtgccatct ccgcttcag accgctccgc gatgaggaca tagcgaagcg catcaggtac   540
atagccgaaa atgagggtct cgagctcacc gaggaaggcc tgcaggcgat actctacgtc   600
gctgagggcg atctcaggag ggcaatcaac gtccttcagg cggcagcagc cctcgacacg   660
aagataaccg acgagaacgt cttcctcgtg ccagcaggg cgaggcctga agacgtacgt   720
gaaatgatga cccttgctct ggaaggcaac ttcctgaagg ccagagagaa gctgagggat   780
atcctgttaa ggcagggcct cagcggtgaa gatgtcctca tccagatgca caaggaggtc   840
ttcaacctcc cgattccga ggacaagaag gtggccctgg cggacaagat aggagagtac   900
cttccgcc tggttgaagg ggctaacgag atgatacagc tcgaggcact ccttgcccag   960
cacgatta tgggtaagtg a                                                981

<210> SEQ ID NO 6
```

<211> LENGTH: 499
<212> TYPE: PRT
<213> ORGANISM: Thermococcus kodakaraensis KOD1
<220> FEATURE:
<223> OTHER INFORMATION: KOD-RFCL

<400> SEQUENCE: 6

```
Met Thr Glu Val Pro Trp Val Glu Lys Tyr Arg Pro Arg Lys Leu Ser
  1               5                  10                  15

Glu Ile Val Asn Gln Glu Lys Ala Leu Glu Gln Val Arg Ala Trp Val
             20                  25                  30

Glu Ala Trp Leu His Gly Asn Pro Pro Lys Lys Ala Leu Leu Leu
         35                  40                  45

Ala Gly Pro Pro Gly Val Gly Lys Thr Thr Val Tyr Ala Leu Ala
     50                  55                  60

Asn Glu Tyr Gly Phe Glu Val Ile Glu Leu Asn Ala Ser Asp Glu Arg
 65                  70                  75                  80

Thr Tyr Glu Lys Ile Glu Arg Tyr Val Gln Ala Ala Tyr Thr Met Asp
                 85                  90                  95

Ile Leu Gly Lys Arg Arg Lys Leu Ile Phe Leu Asp Glu Ala Asp Asn
            100                 105                 110

Ile Glu Pro Ser Gly Ala Arg Glu Ile Ala Lys Leu Ile Asp Lys Ala
        115                 120                 125

Arg Asn Pro Ile Ile Met Ser Ala Asn His Tyr Trp Glu Val Pro Arg
    130                 135                 140

Glu Ile Arg Asn Lys Ala Gln Ile Val Glu Tyr Lys Arg Leu Thr Gln
145                 150                 155                 160

Arg Asp Ile Ile Lys Ala Leu Val Arg Ile Leu Lys Arg Glu Gly Leu
                165                 170                 175

Glu Val Pro Lys Glu Val Leu Tyr Glu Ile Ala Lys Arg Ala Asn Gly
            180                 185                 190

Asp Leu Arg Ala Ala Val Asn Asp Leu Gln Thr Val Thr Gly Gly
        195                 200                 205

Val Glu Asp Ala Val Glu Val Leu Ala Tyr Arg Asp Thr Glu Lys Ser
    210                 215                 220

Val Phe Gln Ala Leu Ala Gln Leu Phe Ala Thr Asp Asn Ala Lys Arg
225                 230                 235                 240

Ala Lys Leu Ala Val Leu Gly Val Asp Met Met Pro Asn Glu Leu Leu
                245                 250                 255

Gln Trp Ile Asp Glu Asn Val Pro Tyr Val Tyr Tyr Arg Pro Glu Asp
            260                 265                 270

Ile Ala Arg Ala Tyr Glu Ala Leu Ser Arg Ala Asp Ile Tyr Leu Gly
        275                 280                 285

Arg Ala Gln Arg Thr Gly Asn Tyr Gly Leu Trp Lys Tyr Ala Thr Asp
    290                 295                 300

Met Met Thr Ala Gly Val Ala Val Ala Gly Ile Lys Lys Lys Gly Phe
305                 310                 315                 320

Val Lys Ile Tyr Pro Pro Lys Thr Ile Lys Leu Leu Thr Glu Ser Lys
                325                 330                 335

Glu Glu Arg Ser Leu Arg Asp Ser Val Ile Lys Lys Ile Met Ser Glu
            340                 345                 350

Met His Met Ala Lys Leu Glu Ala Ile Glu Thr Leu Arg Tyr Leu Arg
        355                 360                 365

Val Ile Phe Glu Asn Asn Pro Asp Leu Ala Ala His Phe Val Val Phe
    370                 375                 380
```

-continued

| | | | | | | | | | | | |
|---|---|---|---|---|---|---|---|---|---|---|---|
|Leu|Asp|Leu|Ser|Glu|Lys|Glu|Val|Glu|Phe|Ile|Thr|Gly|Asp|Lys|Glu|
|385| | | |390| | | |395| | | |400| | | |

Lys Ala Lys Thr Ile Trp Ala Lys Ser Met Asn Ile Glu Lys Lys Leu
            405                 410                 415

Lys Lys Glu Gly Glu Leu Glu Ala Arg Ala Lys Glu Ala Glu Arg Arg
        420                 425                 430

Val Glu Ala Ala Glu Glu Glu Thr Met Glu Ala Gly Glu Pro Glu
            435                 440                 445

Glu Glu Leu Glu Glu Val Glu Glu Glu Leu Thr Glu Glu Glu Leu
        450                 455                 460

Glu Glu Ala Glu Glu Ile Glu Thr Val Gly Lys Glu Lys Pro
465                 470                 475                 480

Glu Lys Glu Lys Thr Lys Lys Gly Lys Gln Ala Thr Leu Phe Asp Phe
                485                 490                 495

Leu Lys Lys

<210> SEQ ID NO 7
<211> LENGTH: 1500
<212> TYPE: DNA
<213> ORGANISM: Thermococcus kodakaraensis KOD1
<220> FEATURE:
<223> OTHER INFORMATION: KOD-RFCL

<400> SEQUENCE: 7

```
atgacggaag tcccatgggt tgaaaaatac agacctagga agctcagcga gatagtaaac      60
caggagaaag cgttagagca ggttagggcg tgggtcgaag cctggctcca cggaaatccg     120
ccgaagaaga aggccctcct tctagcaggc ccccctggag tcggcaaaac gaccaccgtc     180
tatgccctgg ccaacgagta cggcttcgag gtcatcgagc tcaacgcaag cgacgagagg     240
acgtatgaaa agatagagcg ctacgttcaa gctgcataca ctatggatat tctcggaaag     300
aggaggaagc tgatattcct tgacgaggct gacaacatcg agccctctgg ggcgagggag     360
atagcgaagt catcgacaa ggccagaaac ccgataataa tgagcgccaa ccactactgg     420
gaggttccca gggagatacg caacaaagcc cagatagtcg agtacaagag gttgacgcag     480
agggacatca taaaggccct cgtgagaatc ctcaagcgtg agggactcga agttcccaag     540
gaggttctct acgagatagc gaagagggct aacggcgacc tgagggcagc tgtaaacgat     600
cttcagaccg ttgttaccgg tggagtcgag gatgccgttg aagtcctggc ttaccgcgac     660
actgagaaga gcgttttcca ggcgcttgcc cagctgttcg caacggacaa cgccaagagg     720
gcaaagttag ctgttcttgg agttgacatg atgcctaacg agcttctcca gtggatagac     780
gagaacgtcc cgtatgtcta ctacaggcct gaagacatag cgaggccta cgaggcgctc     840 agcagggctg acatataccct cggtagggca cagaggactg gaaactacgg cctctggaag     900
tacgcgaccg acatgatgac ggctgggggtg gcggtcgctg gcatcaagaa gaagggcttc     960
gttaagatct acccacctaa gacgataaag ctcctcaccg agagcaagga ggagcgttcg    1020
ctcagggact cagtaatcaa gaagataatg agcgagatgc acatggctaa gcttgaggcc    1080
atagagaccc tccgctacct tagagttatc ttcgagaaca accccgattt ggcggcccac    1140
tttgtcgttt tcctcgacct cagcgagaag gaagttgagt tcataactgg agacaaggag    1200
aaggcgaaga cgatatgggc aaagagcatg aacattgaga gaaactcaa aaagaaggc    1260 gagcttgagg cgagagcaaa ggaagccgaa gagagggtgg aagcggctga ggaagaggaa    1320
actatggaag ctggggaacc tgaagaagaa cttgaagaag tcgaggagga agagttaacc    1380
```

```
gaggaggagc ttgaggaagc ggaggaagag atagagaccg ttgggaagaa ggagaagccc      1440 agaaggaga aaaccaagaa gggcaagcag gcgacgctgt tcgacttcct caagaagtga       1500

<210> SEQ ID NO 8
<211> LENGTH: 20
<212> TYPE: DNA
<213> ORGANISM: Artificial sequence
<220> FEATURE:
<223> OTHER INFORMATION: Synthetic construct

<400> SEQUENCE: 8
agtgcttcgt gcccgatgac                                                    20

<210> SEQ ID NO 9
<211> LENGTH: 22
<212> TYPE: DNA
<213> ORGANISM: Artificial sequence
<220> FEATURE:
<223> OTHER INFORMATION: Synthetic construct

<400> SEQUENCE: 9
ccagtatcgg cagttgcgta ca                                                 22

<210> SEQ ID NO 10
<211> LENGTH: 22
<212> TYPE: DNA
<213> ORGANISM: Artificial sequence
<220> FEATURE:
<223> OTHER INFORMATION: Synthetic construct

<400> SEQUENCE: 10
ggtgttccct tgatgtagca ca                                                 22

<210> SEQ ID NO 11
<211> LENGTH: 26
<212> TYPE: DNA
<213> ORGANISM: Artificial sequence
<220> FEATURE:
<223> OTHER INFORMATION: Synthetic construct

<400> SEQUENCE: 11
acatgtattt gcatggaaaa caactc                                             26

<210> SEQ ID NO 12
<211> LENGTH: 19
<212> TYPE: DNA
<213> ORGANISM: Artificial sequence
<220> FEATURE:
<223> OTHER INFORMATION: Synthetic construct

<400> SEQUENCE: 12
acagccttca agatggagt                                                     19

<210> SEQ ID NO 13
<211> LENGTH: 20
<212> TYPE: DNA
<213> ORGANISM: Artificial sequence
<220> FEATURE:
<223> OTHER INFORMATION: Synthetic construct

<400> SEQUENCE: 13
ggaggttgga atgtggatag                                                    20

<210> SEQ ID NO 14
```

<211> LENGTH: 20
<212> TYPE: DNA
<213> ORGANISM: Artificial sequence
<220> FEATURE:
<223> OTHER INFORMATION: Synthetic construct

<400> SEQUENCE: 14
agtgcttcgt gcccgatgac                                                  20

<210> SEQ ID NO 15
<211> LENGTH: 22
<212> TYPE: DNA
<213> ORGANISM: Artificial sequence
<220> FEATURE:
<223> OTHER INFORMATION: Synthetic construct

<400> SEQUENCE: 15
ccagtatcgg cagttgcgta ca                                               22

<210> SEQ ID NO 16
<211> LENGTH: 22
<212> TYPE: DNA
<213> ORGANISM: Artificial sequence
<220> FEATURE:
<223> OTHER INFORMATION: Synthetic construct

<400> SEQUENCE: 16
ggtgttccct tgatgtagca ca                                               22

<210> SEQ ID NO 17
<211> LENGTH: 26
<212> TYPE: DNA
<213> ORGANISM: Artificial sequence
<220> FEATURE:
<223> OTHER INFORMATION: Synthetic construct

<400> SEQUENCE: 17
acatgtattt gcatggaaaa caactc                                           26

<210> SEQ ID NO 18
<211> LENGTH: 25
<212> TYPE: DNA
<213> ORGANISM: Artificial sequence
<220> FEATURE:
<223> OTHER INFORMATION: Synthetic construct

<400> SEQUENCE: 18
tggaagtgtg gatattgtcc agtgc                                            25

<210> SEQ ID NO 19
<211> LENGTH: 27
<212> TYPE: DNA
<213> ORGANISM: Artificial sequence
<220> FEATURE:
<223> OTHER INFORMATION: Synthetic construct

<400> SEQUENCE: 19
cagggcggtt tgcttctcag caataga                                          27

<210> SEQ ID NO 20
<211> LENGTH: 33
<212> TYPE: DNA
<213> ORGANISM: Artificial sequence
<220> FEATURE:
<223> OTHER INFORMATION: Synthetic construct

<400> SEQUENCE: 20
agtgccctgt cctccagata ccactgagcc tct                33

<210> SEQ ID NO 21
<211> LENGTH: 35
<212> TYPE: DNA
<213> ORGANISM: Artificial sequence
<220> FEATURE:
<223> OTHER INFORMATION: Synthetic construct

<400> SEQUENCE: 21
gcagcctaag ggtgggaaaa tagaccaata ggcag              35

<210> SEQ ID NO 22
<211> LENGTH: 34
<212> TYPE: DNA
<213> ORGANISM: Artificial sequence
<220> FEATURE:
<223> OTHER INFORMATION: Synthetic construct

<400> SEQUENCE: 22
ccttcactgt ctgcctaact ccttcgtgtg ttcc               34

<210> SEQ ID NO 23
<211> LENGTH: 31
<212> TYPE: DNA
<213> ORGANISM: Artificial sequence
<220> FEATURE:
<223> OTHER INFORMATION: Synthetic construct

<400> SEQUENCE: 23
gatgcgaaac tgaggctggc tgtactgtct c                  31

<210> SEQ ID NO 24
<211> LENGTH: 31
<212> TYPE: DNA
<213> ORGANISM: Artificial sequence
<220> FEATURE:
<223> OTHER INFORMATION: Synthetic construct

<400> SEQUENCE: 24
tgtctccagc acacagcatg ttgtcggtga c                  31

<210> SEQ ID NO 25
<211> LENGTH: 34
<212> TYPE: DNA
<213> ORGANISM: Artificial sequence
<220> FEATURE:
<223> OTHER INFORMATION: Synthetic construct

<400> SEQUENCE: 25
ccttctagag tcaactctag atgtggactt agag               34

<210> SEQ ID NO 26
<211> LENGTH: 34
<212> TYPE: DNA
<213> ORGANISM: Artificial sequence
<220> FEATURE:
<223> OTHER INFORMATION: Synthetic construct

<400> SEQUENCE: 26
actgtgcttc ctgacccatg gcagaagcgc cttc               34

<210> SEQ ID NO 27
<211> LENGTH: 34
<212> TYPE: DNA

```
<213> ORGANISM: Artificial sequence
<220> FEATURE:
<223> OTHER INFORMATION: Synthetic construct

<400> SEQUENCE: 27 gcagggtgc tgcagaactc tgagctgtac ttcc                                    34

<210> SEQ ID NO 28
<211> LENGTH: 35
<212> TYPE: DNA
<213> ORGANISM: Artificial sequence
<220> FEATURE:
<223> OTHER INFORMATION: Synthetic construct

<400> SEQUENCE: 28
tgcacctgct ctgtgattat gactatccca cagtc                                  35

<210> SEQ ID NO 29
<211> LENGTH: 35
<212> TYPE: DNA
<213> ORGANISM: Artificial sequence
<220> FEATURE:
<223> OTHER INFORMATION: Synthetic construct

<400> SEQUENCE: 29
acatgattag caaaagggcc tagcttggac tcaga                                  35

<210> SEQ ID NO 30
<211> LENGTH: 34
<212> TYPE: DNA
<213> ORGANISM: Artificial sequence
<220> FEATURE:
<223> OTHER INFORMATION: Synthetic construct

<400> SEQUENCE: 30
ggaagtacag ctcagagttc tgcagcaccc ctgc                                   34

<210> SEQ ID NO 31
<211> LENGTH: 31
<212> TYPE: DNA
<213> ORGANISM: Artificial sequence
<220> FEATURE:
<223> OTHER INFORMATION: Synthetic construct

<400> SEQUENCE: 31
caaagtcatg cggccatcgt tcagacacac c                                      31

<210> SEQ ID NO 32
<211> LENGTH: 34
<212> TYPE: DNA
<213> ORGANISM: Artificial sequence
<220> FEATURE:
<223> OTHER INFORMATION: Synthetic construct

<400> SEQUENCE: 32
cggaattcat gmgsgcyatg gayccvagya grgt                                   34

<210> SEQ ID NO 33
<211> LENGTH: 31
<212> TYPE: DNA
<213> ORGANISM: Artificial sequence
<220> FEATURE:
<223> OTHER INFORMATION: Synthetic construct

<400> SEQUENCE: 33
gctctagata stccatytgs aksggcatyt c                                      31
```

<210> SEQ ID NO 34
<211> LENGTH: 23
<212> TYPE: DNA
<213> ORGANISM: Artificial sequence
<220> FEATURE:
<223> OTHER INFORMATION: Synthetic construct

<400> SEQUENCE: 34
gagctcaacg csagygatga gag                                            23

<210> SEQ ID NO 35
<211> LENGTH: 23
<212> TYPE: DNA
<213> ORGANISM: Artificial sequence
<220> FEATURE:
<223> OTHER INFORMATION: Synthetic construct

<400> SEQUENCE: 35
tcyctbgcct ccatgaastt acc                                            23

<210> SEQ ID NO 36
<211> LENGTH: 31
<212> TYPE: DNA
<213> ORGANISM: Artificial sequence
<220> FEATURE:
<223> OTHER INFORMATION: Synthetic construct

<400> SEQUENCE: 36
cggaattcga gctcaacgcs agygatgaga g                                   31

<210> SEQ ID NO 37
<211> LENGTH: 32
<212> TYPE: DNA
<213> ORGANISM: Artificial sequence
<220> FEATURE:
<223> OTHER INFORMATION: Synthetic construct

<400> SEQUENCE: 37
gctctagact skagcytact catgtgcatc tc                                  32

<210> SEQ ID NO 38
<211> LENGTH: 581
<212> TYPE: DNA
<213> ORGANISM: Thermococcus kodakaraensis KOD1
<220> FEATURE:
<223> OTHER INFORMATION: KOD-PCNA fragment

<400> SEQUENCE: 38
atgcgggcta tggatccgag tagggtcgtt ctcattgacc tcaacctgcc cgaaagcatc     60
ttctccaagt acgaggtcga agagcccgag acaatcggca tcaacatgga ccagttcaag    120
aaaatcctca gcgcggcaa ggcgaaagac accctcatac tcaggaaggg cgacgagaac    180
ttccttgaga taacttttga gggaaccgcc aagaggacat caggctcccc tctgatagat    240
gtggaagagc ttgagctgga gcttcccgag ctcccgttca cggctaaggt agtcctcctc    300
ggtgaggttc tcaaggaggg cataaaggac gcttccctcg tcagcgacgc catcaagttc    360
atagcaaagg agaacgagtt cacaatgaag gccgagggcg agaccaacga ggtcgagata    420
aggcttaccc ttgaggacga gggccttctc gaccttgaag tcgaggaaga gaccaagagt    480
gcctacggca taagctacct cagcgacatg gtcaagggca tcgggaaggc cgacgaagtt    540
atcctccgct tcggcaacga aatgcccctc caaatggagt a                       581

<210> SEQ ID NO 39
<211> LENGTH: 526
<212> TYPE: DNA
<213> ORGANISM: Artificial sequence
<220> FEATURE:
<223> OTHER INFORMATION: KOD-RFCS fragment

<400> SEQUENCE: 39

```
gagctcaacg cagagatgag agggtataa acgtcatccg tgaaaaggta aaggagttcg      60
cgaggacgaa gccgataggc ggtgcgagct ttaagataat cttccttgat gaggcagatg     120
ccctcacaca ggacgctcag caggccctca gaaggacgat ggagatgttc tcgaacaacg     180
tccgctttat cctgagctgt aactactcct caaagatcat cgaacccata cagtcgaggt     240
gtgccatctt ccgcttcaga ccgctccgcg atgaggacta gcgaagcgc atcaggtaca      300 tagccgaaaa tgagggtctc gagctcaccg aggaaggcct gcaggcgata ctctacgtcg     360
ctgagggcga tctcaggagg gcaatcaacg tccttcaggc ggcagcagcc ctcgacacga     420
agataaccga cgagaacgtc ttcctcgtgg ccagcagggc gaggcctgaa gacgtacgtg     480
aaatgatgac ccttgctctg gaaggtaact tcatggaggc caggga                   526
```

<210> SEQ ID NO 40
<211> LENGTH: 860
<212> TYPE: DNA
<213> ORGANISM: Artificial sequence
<220> FEATURE:
<223> OTHER INFORMATION: KOD-RFCL fragment

<400> SEQUENCE: 40

```
gagctcaacg cagagatgag aggacgtatg aaaagataga gcgctacgtt caagctgcat     60
acactatgga tattctcgga aagaggagga agctgatatt ccttgacgag gctgacaaca    120
tcgagccctc tggggcgagg gagatagcga agctcatcga caaggccaga aacccgataa    180
taatgagcgc caaccactac tgggaggttc ccagggagat acgcaacaaa gcccagatag    240
tcgagtacaa gaggttgacg cagagggaca tcataaaggc cctcgtgaga atcctcaagc    300
gtgagggact cgaagttccc aaggaggttc tctacgagat agcgaagagg gctaacggcg    360
acctgagggc agctgtaaac gatcttcaga ccgttgttac cggtggagtc gaggatgccg    420
ttgaagtcct ggcttaccgc gacactgaga agagcgtttt ccaggcgctt gcccagctgt    480
tcgcaacgga caacgccaag agggcaaagt tagctgttct tggagttgac atgatgccta    540
acgagcttct ccagtggata gacgagaacg tcccgtatgt ctactacagg cctgaagaca    600
tagcgagggc ctacgaggcg ctcagcaggg ctgacatata cctcggtagg gcacagagga    660
ctggaaacta cggcctctgg aagtacgcga ccgacatgat gacggctggg gtggcggtcg    720
ctggcatcaa gaagaagggc ttcgttaaga tctacccacc taagacgata aagctcctca    780
ccgagagcaa ggaggagcgt tcgctcaggg actcagtaat caagaagata atgagcgaga    840
tgcacatgag taagctccag                                              860
```

<210> SEQ ID NO 41
<211> LENGTH: 24
<212> TYPE: DNA
<213> ORGANISM: Artificial sequence
<220> FEATURE:
<223> OTHER INFORMATION: Synthetic construct

<400> SEQUENCE: 41

```
actgcgcaac tcgtgaaagg tagg                                          24
```

<210> SEQ ID NO 42
<211> LENGTH: 24
<212> TYPE: DNA
<213> ORGANISM: Artificial sequence
<220> FEATURE:
<223> OTHER INFORMATION: Synthetic construct

<400> SEQUENCE: 42
tgccgagaat aacgagtgga tctg 24

<210> SEQ ID NO 43
<211> LENGTH: 24
<212> TYPE: DNA
<213> ORGANISM: Artificial sequence
<220> FEATURE:
<223> OTHER INFORMATION: Synthetic construct

<400> SEQUENCE: 43
gacatggtca agggcatcgg gaag 24

<210> SEQ ID NO 44
<211> LENGTH: 24
<212> TYPE: DNA
<213> ORGANISM: Artificial sequence
<220> FEATURE:
<223> OTHER INFORMATION: Synthetic construct

<400> SEQUENCE: 44
cgcttgagga ttttcttgaa ctgg 24

<210> SEQ ID NO 45
<211> LENGTH: 24
<212> TYPE: DNA
<213> ORGANISM: Artificial sequence
<220> FEATURE:
<223> OTHER INFORMATION: Synthetic construct

<400> SEQUENCE: 45
cgcttgagga ttttcttgaa ctgg 24

<210> SEQ ID NO 46
<211> LENGTH: 24
<212> TYPE: DNA
<213> ORGANISM: Artificial sequence
<220> FEATURE:
<223> OTHER INFORMATION: Synthetic construct

<400> SEQUENCE: 46
tctgcctcat caaggaagat tatc 24

<210> SEQ ID NO 47
<211> LENGTH: 24
<212> TYPE: DNA
<213> ORGANISM: Artificial sequence
<220> FEATURE:
<223> OTHER INFORMATION: Synthetic construct

<400> SEQUENCE: 47
ttcgttaaga tctacccacc taag 24

<210> SEQ ID NO 48
<211> LENGTH: 24
<212> TYPE: DNA
<213> ORGANISM: Artificial sequence
<220> FEATURE:

<223> OTHER INFORMATION: Synthetic construct

<400> SEQUENCE: 48
ttgtcagcct cgtcaaggaa tatc                                                              24

<210> SEQ ID NO 49
<211> LENGTH: 32
<212> TYPE: DNA
<213> ORGANISM: Artificial sequence
<220> FEATURE:
<223> OTHER INFORMATION: Synthetic construct

<400> SEQUENCE: 49
ggaattccat atgtccgagg aagtgaagga ag                                                     32

<210> SEQ ID NO 50
<211> LENGTH: 29
<212> TYPE: DNA
<213> ORGANISM: Artificial sequence
<220> FEATURE:
<223> OTHER INFORMATION: Synthetic construct

<400> SEQUENCE: 50
cagcggttgt cttcccgacg ccgggtggc                                                         29

<210> SEQ ID NO 51
<211> LENGTH: 32
<212> TYPE: DNA
<213> ORGANISM: Artificial sequence
<220> FEATURE:
<223> OTHER INFORMATION: Synthetic construct

<400> SEQUENCE: 51
cgtcgggaag acaaccgctg cactggcttt ag                                                     32

<210> SEQ ID NO 52
<211> LENGTH: 30
<212> TYPE: DNA
<213> ORGANISM: Artificial sequence
<220> FEATURE:
<223> OTHER INFORMATION: Synthetic construct

<400> SEQUENCE: 52
gctctagatc acttacccat aatcgtgaac                                                        30

<210> SEQ ID NO 53
<211> LENGTH: 30
<212> TYPE: DNA
<213> ORGANISM: Artificial sequence
<220> FEATURE:
<223> OTHER INFORMATION: Synthetic construct

<400> SEQUENCE: 53
ggaattccat atgccgttcg aagttgtttt                                                        30

<210> SEQ ID NO 54
<211> LENGTH: 30
<212> TYPE: DNA
<213> ORGANISM: Artificial sequence
<220> FEATURE:
<223> OTHER INFORMATION: Synthetic construct

<400> SEQUENCE: 54
gctctagatc actcctcaac gcgcggagcg                                                        30

<210> SEQ ID NO 55
<211> LENGTH: 32
<212> TYPE: DNA
<213> ORGANISM: Artificial sequence
<220> FEATURE:
<223> OTHER INFORMATION: Synthetic construct

<400> SEQUENCE: 55
ggaattccat atgacggaag tcccatgggt tg                32

<210> SEQ ID NO 56
<211> LENGTH: 32
<212> TYPE: DNA
<213> ORGANISM: Artificial sequence
<220> FEATURE:
<223> OTHER INFORMATION: Synthetic construct

<400> SEQUENCE: 56
gctctagatc acttcttgag gaagtcgaac ag                32

<210> SEQ ID NO 57
<211> LENGTH: 19
<212> TYPE: DNA
<213> ORGANISM: Artificial sequence
<220> FEATURE:
<223> OTHER INFORMATION: Synthetic construct

<400> SEQUENCE: 57
taatacgact cactatagg                                19

<210> SEQ ID NO 58
<211> LENGTH: 30
<212> TYPE: DNA
<213> ORGANISM: Artificial sequence
<220> FEATURE:
<223> OTHER INFORMATION: Synthetic construct

<400> SEQUENCE: 58
gactagtcac ttcttgagga agtcgaacag                    30

<210> SEQ ID NO 59
<211> LENGTH: 24
<212> TYPE: DNA
<213> ORGANISM: Artificial sequence
<220> FEATURE:
<223> OTHER INFORMATION: Synthetic construct

<400> SEQUENCE: 59
cgccagggtt ttcccagtca cgac                          24

<210> SEQ ID NO 60
<211> LENGTH: 22
<212> TYPE: DNA
<213> ORGANISM: Artificial sequence
<220> FEATURE:
<223> OTHER INFORMATION: Synthetic construct

<400> SEQUENCE: 60
ggtgttccct tgatgtagca ca                            22

<210> SEQ ID NO 61
<211> LENGTH: 26
<212> TYPE: DNA
<213> ORGANISM: Artificial sequence
<220> FEATURE:
<223> OTHER INFORMATION: Synthetic construct

```
<400> SEQUENCE: 61
acatgtattt   gcatggaaaa   caactc                                                          26
```

The invention claimed is:

1. A method for enhancing synthesis of DNA comprising
(a) providing a mixture comprising a template nucleic acid and components for enzymatic DNA synthesis of the template nucleic acid, wherein the components comprise an enzyme with DNA polymerase activity,
(b) adding to the mixture at least one carboxylate ion-supplying substance that is effective in promoting DNA synthesis in enzymatic DNA synthesis reactions, wherein the carboxylate ion-supplying substance is selected from the group consisting of oxalic acid, malonic acid, esters of oxalic acid, esters of malonic acid, salts of malonic acid, and esters of maleic acid, and
(c) maintaining the mixture to provide DNA synthesis of the template nucleic acid.

2. The method of claim 1, wherein the carboxylate ion-supplying substance is oxalic acid or malonic acid.

3. The method of claim 1, wherein the carboxylate ion-supplying substance is a malonic acid salt.

4. The method of claim 1, wherein the carboxylate ion-supplying substance is an oxalic acid ester, a malonic acid ester or a maleic acid ester.

5. The method of claim 1, wherein the method further comprises adding to the mixture at least one compound selected from the group consisting of dimethylsulfoxide and compounds represented by the following formula

$$R^2—CH_2—NR^1_xH_y \quad (1)$$

wherein $R^1$ is an alkyl group having 1 to 3 carbon atoms, $R^2$ is a substituent selected from the group consisting of the following (a) and (b):
(a) =O (oxygen) and (b) radicals represented by the formula

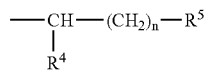

$$—CH—(CH_2)_n—R^5$$
$$\quad |$$
$$\quad R^4$$

wherein $R^4$ is methyl or hydrogen and forms a pyrrolidine ring when combined with $R^1$, $R^5$ is —$CO_2H$ or —$SO_3H$, and n is an integer from 0 to 2,
x is an integer from 1 to 3 and
y is an integer from 0 to 2, provided that x plus y equals 3.

6. The method of claim 5, wherein the compound of formula (1) is trimethylglycine.

7. The method of claim 5, wherein the mixture contains the compound of formula (1) in an amount of 0.5 to 2M and/or dimethylsulfoxide in an amount of 0.1 to 15 wt. %.

8. A composition for synthesizing DNA comprising at least one carboxylate ion-supplying substance that is effective in promoting DNA synthesis in enzymatic DNA synthesis reactions and an enzyme having DNA polymerase activity, wherein the carboxylate ion-supplying substance is selected from the group consisting of oxalic acid, malonic acid, esters of oxalic acid, esters of malonic acid, salts of malonic acid, and esters of maleic acid.

9. The composition of claim 8, wherein the enzyme having DNA polymerase activity is a DNA-directed DNA polymerase.

10. The composition of claim 9, wherein the DNA-directed DNA polymerase is selected from the group consisting of Taq polymerase, Tth polymerase, Tli polymerase, Pfu polymerase, Pfutubo polymerase, Pyrobest polymerase, Pwo polymerase, KOD polymerase, Bst polymerase, Sac polymerase, Sso polymerase, Poc polymerase, Pab polymerase, Mth polymerase, Pho polymerase, ES4 polymerase, VENT polymerase, DEEPVENT polymerase, EX-Taq polymerase, LA-Taq polymerase, Expand polymerases, Platinum Taq polymerases, Hi-Fi polymerase, Tbr polymerase, Tfl polymerase, Tru polymerase, Tac polymerase, Tne polymerase, Tma polymerase, Tih polymerase, Tfi polymerase, and variants, modified products and derivatives thereof.

11. The composition of claim 9, wherein the DNA-directed DNA polymerase is a thermostable DNA-directed DNA polymerase which synthesizes DNA at a rate of at least 30 bases/second and has 3'-5' exonuclease activity.

12. The composition of claim 9, wherein the DNA-directed DNA polymerase is a thermostable DNA-directed DNA polymerase which synthesizes DNA at a rate of at least 30 bases/second and which exhibits an error rate of 4% or less when performing PCR using pMol 21 as a template.

13. The composition of claim 8, wherein the enzyme having DNA polymerase activity is a reverse transcriptase.

14. The composition of claim 13, wherein the reverse transcriptase is an enzyme selected from the group consisting of AMV-RT polymerase, M-MLV-RT polymerase, HIV-RT polymerase, EIAV-RT polymerase, RAV2-RT polymerase, C. hydrogenoformans DNA polymerase, SuperScript I, SuperScript II, and variants, modified products and derivatives thereof.

15. The composition of claim 13, wherein the reverse transcriptase is an enzyme with substantially reduced RnaseH activity.

16. The composition of claim 8, wherein the composition further comprises at least one member selected from the group consisting of nucleotides, nucleotide derivatives, buffers, salts, template nucleic acids and primers.

17. The composition of claim 16, wherein the nucleotides are deoxyphosphonucleotides and nucleotide derivatives are deoxyphosphonucleotide derivatives.

18. The composition of claim 17, wherein the deoxyphosphonucleotides and derivatives thereof are selected from the group consisting of dATP, dCTP, dGTP, dTTP, dITP, dUTP, α-thio-dNTPs, biotin-dUTP, fluorescein-dUTP and digoxigenin-dUTP.

19. A method for synthesizing DNA comprising the steps of:
(a) mixing a template nucleic acid with the composition of claim 8, a nucleotide and/or a nucleotide derivative, and primers to form a mixture; and
(b) incubating the mixture under such conditions that DNA is synthesized at a rate of at least 30 bases/second and, when performing PCR using pMol 21 as a template, the error rate is 4% or less to prepare a first nucleic acid molecule complementary to the entire or part of the template nucleic acid.

20. The method of claim 19 further comprising the step of (c) incubating a mixture containing the first nucleic acid molecule under such conditions that DNA is synthesized at a rate of at least 30 bases/second and, when performing PCR using pMol 21 as a template, the error rate is 4% or less to prepare a second nucleic acid molecule complementary to the entire or part of the first nucleic acid molecule.

21. The method of claim 19 using hot start PCR.

22. A DNA amplification method comprising the steps of:
(a) mixing a template nucleic acid with the composition of claim 8, nucleotide and/or nucleotide derivatives and primers to form a mixture; and
(b) incubating the mixture under such conditions that DNA is synthesized at a rate of at least 30 bases/second and, when performing PCR using pMol 21 as a template, the error rate is 4% or less to amplify a nucleic acid molecule complementary to the entire or part of the template nucleic acid.

23. The method of claim 22 further comprising the step of (c) incubating a mixture containing the first nucleic acid molecule under such conditions that DNA is synthesized at a rate of at least 30 bases/second and, when performing PCR using pMol 21 as a template, the error rate is 4% or less to prepare a second nucleic acid molecule complementary to the entire or part of the first nucleic acid.

24. The method of claim 22 using hot start PCR.

25. A method for nucleotide sequencing comprising the steps of:
(a) mixing a target nucleic acid with the composition of claim 8, nucleotide and/or nucleotide derivatives, primers and a release factor to form a mixture;
(b) incubating the mixture under such conditions that DNA is synthesized at a rate of at least 30 bases/second and, when performing PCR using pMol 21 as a template, the error rate is 4% or less to amplify a nucleic acid molecule complementary to the entire or part of the target nucleic acid; and
(c) separating the amplified nucleic acid molecule to determine the entire or partial nucleotide sequence.

26. The method of claim 25 further comprising, between steps (b) and (e) (or between steps (b) and (d) when the process further comprises step (d)), the step of (c) incubating a mixture containing a first nucleic acid molecule under such conditions that DNA is synthesized at a rate of at least 30 bases/second and, when performing PCR using pMol 21 as a template, the error rate is 4% or less to prepare a second nucleic acid molecule complementary to the entire or part of the first nucleic acid molecule.

27. The method of claim 25 using hot start PCR.

28. A kit for synthesizing DNA comprising a DNA polymerase and a thermostable DNA polymerase-related factor derived from a hyperthermophilic archaeon, *Thermococcus kodakaraensis*, which promotes the DNA synthesis activity of a DNA polymerase, wherein the thermo stable DNA polymerase-related factor is selected from the group consisting of:
(a) a protein comprising the amino acid sequence of SEQ ID NO: 6; and
(b) a protein comprising an amino acid sequence encoded by the nucleotide sequence of SEQ ID NO: 7.

29. A method for synthesizing DNA comprising
(a) providing a mixture comprising a template nucleic acid, at least one carboxylate ion-supplying substance that is effective in promoting DNA synthesis in enzymatic DNA synthesis reactions, and an enzyme having DNA polymerase activity, wherein the carboxylate ion-supplying substance is selected from the group consisting of oxalic acid, malonic acid, esters of oxalic acid, esters of malonic acid, salts of malonic acid, and esters of maleic acid, and
(b) maintaining the mixture to provide DNA synthesis of the template nucleic acid.

30. The method of claim 29, wherein the enzyme having DNA polymerase activity is a DNA-directed DNA polymerase.

31. The method of claim 30, wherein the DNA-directed DNA polymerase is selected from the group consisting of Taq polymerase, Tth polymerase, Tli polymerase, Pfu polymerase, Pfutubo polymerase, Pyrobest polymerase, Pwo polymerase, KOD polymerase, Bst polymerase, Sac polymerase, Sso polymerase, Poc polymerase, Pab polymerase, Mth polymerase, Pho polymerase, ES4 polymerase, VENT polymerase, DEEPVENT polymerase, EX-Taq polymerase, LA-Taq polymerase, Expand polymerases, Platinum Taq polymerases, Hi-Fi polymerase, Tbr polymerase, Tfl polymerase, Tru polymerase, Tac polymerase, Tne polymerase, Tma polymerase, Tih polymerase, Tfi polymerase, and variants, modified products and derivatives thereof.

32. The method of claim 30, wherein the DNA-directed DNA polymerase is a thermostable DNA-directed DNA polymerase which synthesizes DNA at a rate of at least 30 bases/second and has 3'-5' exonuclease activity.

33. The method of claim 30, wherein the DNA-directed DNA polymerase is a thermostable DNA-directed DNA polymerase which synthesizes DNA at a rate of at least 30 bases/second and which exhibits an error rate of 4% or less when performing PCR using mMOl 21 as a template.

34. The method of claim 29, wherein the enzyme having DNA polymerase activity is a reverse transcriptase.

35. The method of claim 34, wherein the reverse transcriptase is an enzyme selected from the group consisting of AMV-RT polymerase, M-MLV-RT polymerase, HIV-RT polymerase, EIAV-RT polymerase, RAV2-RT polymerase, C. hydrogenoformans DNA polymerase, SuperScript I, SuperScript II, and variants, modified products and derivatives thereof.

36. The method of claim 34, wherein the reverse transcriptase is an enzyme with substantially, reduced RnaseH activity.

37. The method of claim 29, further comprising adding at least one member selected from the group consisting of nucleotides, nucleotide derivatives, buffers, salts, template nucleic acids and primers.

38. The method of claim 37, wherein the nucleotides are deoxyphosphonucleotides and nucleotide derivatives are deoxyphosphonucleotide derivatives.

39. The method of claim 38, wherein the deoxyphosphonucleotides and derivatives thereof are selected from the group consisting of dATP, dCTP, dGTP, dTTP, dITP, dUTP, α-thio-dNTPs, biotin-dUTP, fluorescein-dUTP and digoxigenin-dUTP.

40. The composition of claim 8, wherein the carboxylate ion-supplying substance is selected from the group consisting of malonic acid, esters of malonic acid, and salts of malonic acid.

41. The composition of claim 40, wherein the carboxylate-ion-supplying substance is selected from the group consisting of zinc oxalate, ammonium oxalate, potassium oxalate, calcium oxalate, diethyl oxylate, N,N'-disuccinimidyl oxalate, dimethyl oxalate, tin oxalate, cerium oxalate, iron oxalate, copper oxalate, sodium oxalate, nickel oxalate, bis oxalate, 2,4-dinitrophenyl oxalate, 2,4,6-trichlorophenyl oxalate, manganese oxalate, methyl oxalate, lanthanum oxalate, lithium oxalate, isoproplylidene malonate, ethyl malonate, diethyl malonate, dibenzyl malonate, dimethyl malonate, thallium malonate, and disodium malonate.

42. The composition of claim 8, wherein the composition further comprises at least one compound selected from the group consisting of dimethylsulfoxide and compounds represented by the following formula $$R^2\text{—}CH_2\text{—}NR^1{}_xH_y \tag{1}$$

wherein $R^1$ is an alkyl group having 1 to 3 carbon atoms, $R^2$ is a substituent selected from the group consisting of the following (a) and (b):

(a) =O (oxygen) and (b) radicals represented by the formula

wherein $R^4$ methyl or hydrogen and forms a pyrrolidine ring when combined with $R^1$, $R^5$ is —$CO_2H$ or —$SO_3H$, and n is an integer from 0 to 2, x is an integer from 1 to 3 and y is an integer from 0 to 2, provided that x plus y equals 3.

* * * * *